United States Patent
Cua et al.

(10) Patent No.: US 12,037,393 B2
(45) Date of Patent: Jul. 16, 2024

(54) PI16 ANTIBODIES

(71) Applicant: Merck Sharp & Dohme LLC, Rahway, NJ (US)

(72) Inventors: Daniel Cua, Boulder Creek, CA (US); Holly Cherwinski, Boulder Creek, CA (US); Adele Wang, San Mateo, CA (US); Yi Chen, San Jose, CA (US); Barbara Joyce-Shaikh, San Jose, CA (US)

(73) Assignee: Merck Sharpe & Dohme LLC, Rahway, NJ (US)

( * ) Notice: Subject to any disclaimer, the term of this patent is extended or adjusted under 35 U.S.C. 154(b) by 0 days.

(21) Appl. No.: 17/663,558

(22) Filed: May 16, 2022

(65) Prior Publication Data

US 2022/0363756 A1 Nov. 17, 2022

Related U.S. Application Data

(63) Continuation of application No. 16/342,582, filed as application No. PCT/US2017/060154 on Nov. 6, 2017, now Pat. No. 11,370,839.

(60) Provisional application No. 62/420,173, filed on Nov. 10, 2016.

(51) Int. Cl.
*C07K 16/28* (2006.01)
*A61K 39/00* (2006.01)
*A61P 35/00* (2006.01)
*G01N 33/542* (2006.01)

(52) U.S. Cl.
CPC .......... *C07K 16/2803* (2013.01); *A61P 35/00* (2018.01); *G01N 33/542* (2013.01); *A61K 2039/505* (2013.01); *C07K 2317/32* (2013.01); *C07K 2317/76* (2013.01)

(58) Field of Classification Search
None
See application file for complete search history.

(56) References Cited

U.S. PATENT DOCUMENTS

| 5,958,708 A | 9/1999 | Hardman et al. |
| 2011/0200615 A1 | 8/2011 | Marks et al. |
| 2015/0110714 A1 | 4/2015 | Suciu Foca et al. |
| 2015/0139986 A1 | 5/2015 | Ponath et al. |
| 2021/0349096 A1 | 11/2021 | Zhang et al. |

FOREIGN PATENT DOCUMENTS

| WO | 2003093474 A1 | 11/2003 | |
| WO | WO2005068503 A2 | 7/2005 | |
| WO | WO2007014991 A1 | 2/2007 | |
| WO | 2008117049 A1 | 10/2008 | |
| WO | WO2008145338 A2 | 12/2008 | |
| WO | WO-2011127543 A1 * | 10/2011 | ............. C07K 16/28 |
| WO | WO2013063110 A1 | 5/2013 | |
| WO | WO2015116753 A1 | 8/2015 | |
| WO | WO2016073629 A1 | 5/2016 | |
| WO | 2016156588 A1 | 10/2016 | |
| WO | 2017015227 A1 | 1/2017 | |
| WO | 2018148494 A1 | 8/2018 | |

OTHER PUBLICATIONS

Cella et al., A Novel Inhibitory Receptor (ILT3) Expressed on Monocytes, Macrophages, and Dendritic Cells Involved in Antigen Processing, J. Exp. Med., 1997, Issue 10, pp. 1743-1751, 185.
Columbia University in the City of New York, Recombinant ILT3 protein for the treatment of cancer, Columbia Technology Ventures, 2015, 1-2, N/A.
Kang, Xunlei et al., Inhibitory leukocyte immunoglobulin-like receptors: Immune checkpoint proteins and tumor sustaining factors, Cell Cycle, 2015, 25-40, 15(1).
Laure Jason-Muller, et al., Overview of Biacore Systems and Their Applications, Current Protocols in Protein Science, 2006, 14 pages, 19.13.
Xu, Zheng et al., ILT3.Fc-CD166 Interaction Induces Inactivation of p70 S6 Kinase and Inhibits Tumor Cell Growth, The Journal of Immunology, 2017, 1207-1219, 200.
Zhang, Xiaojing; et al., Forster resonance energy transfer (FRET)-based biosensors for biological applications, Elsevier, Biosensors and Bioelectronics, 2019, 13 pages, 138.
U.S. Appl. No. 16/342,582, filed Apr. 17, 2019.

* cited by examiner

*Primary Examiner* — Amy E Juedes
(74) *Attorney, Agent, or Firm* — Su Kyung Suh; Anna L. Cocuzzo

(57) ABSTRACT

The present invention provides antibodies and antigen-binding fragments thereof that bind PI16 and block binding of ILT3 to PI16.

13 Claims, 13 Drawing Sheets

Specification includes a Sequence Listing.

Validation of ILT3 Retrogenix test ligands

PI16
PODXL2
CLDN3
PI16
VSIG1
NIPA1
FcgR2B

*Human Embryonic Kidney cells (HEK293T)

| Sample number | Gene | Correct accession | % Query | % Id |
|---|---|---|---|---|
| 1 | MAG | NM_002361.3 | 96 | 99 |
| 2 | PODXL2 | NM_015720.3 | 96 | 99 |
| 3 | CLDN3 | BC16056.1 | 96 | 100 |
| 4 | NIPA1 | NM_144599.4 | 93 | 98 |
| 5 | PI16 | BC022399.1 | 96 | 100 |
| 6 | VSIG1 | NM182067.4 | 97 | 99 |
| 7 | FCGR2B | BC031992.1 | 97 | 100 |

PI16

---------------------------------------------------------------------------- Section 1
                    (1)    1        10        20        30        40        50        65
PI16_Q6UXB8_1      (1)    MHGSCSFLMLLLPLLLLLVATTGPVGALTDEEKRLMVELHNLYRAQVSPTASDMLHMRWDEELAA
PI16_Q6UXB8_2      (1)    MHGSCSFLMLLLPLLLLLVATTGPVGALTDEEKRLMVELHNLYRAQVSPTASDMLHMRWDEELAA
PI16_Retrogenix    (1)    MHGSCSFLMLLLPLLLLLVATTGPVGALTDEEKRLMVELHNLYRAQVSPTASDMLHMRWDEELAA ---------------------------------------------------------------------------- Section 2
                    (66)   66       80        90        100       110       120       130
PI16_Q6UXB8_1      (66)   FAKAYARQCVWGHNKERGRRGENLFAITDEGMDVPLAMEEWHHEREHYNLSAATCSPGQMCGHYT
PI16_Q6UXB8_2      (66)   FAKAYARQCVWGHNKERGRRGENLFAITDEGMDVPLAMEEWHHEREHYNLSAATCSPGQMCGHYT
PI16_Retrogenix    (66)   FAKAYARQCVWGHNKERGRRGENLFAITDEGMDVPLAMEEWHHEREHYNLSAATCSPGQMCGHYT ---------------------------------------------------------------------------- Section 3
                    (131)  131      140       150       160       170       180       195
PI16_Q6UXB8_1      (131)  QVVWAKTERIGCGSHFCEKLQGVEETNIELLVCNYEPPGNVKGKRPYQEGTPCSQCPSGYHCKNS
PI16_Q6UXB8_2      (131)  QVVWAKTERIGCGSHFCEKLQGVEETNIELLVCNYEPPGNVKGKRPYQEGTPCSQCPSGYHCKNS
PI16_Retrogenix    (131)  QVVWAKTERIGCGSHFCEKLQGVEETNIELLVCNYEPPGNVKGKRPYQEGTPCSQCPSGYHCKNS ---------------------------------------------------------------------------- Section 4
                    (196)  196      210       220       230       240       250       260
PI16_Q6UXB8_1      (196)  LCEPIGSPEDAQDLPYLVYEAPSFRATEASDSRKMGTPSSLATGIPAFLVTEVSGSLATKALPAV
PI16_Q6UXB8_2      (196)  LCEPIGSPEDAQDLPYLVYEAPSFRATEASDSRKMG-----------------------------
PI16_Retrogenix    (196)  LCEPIGSPEDAQDLPYLVYEAPSFRATEASDSRKMGTPSSLATGIPAFLVTEVSGSLATKALPAV ---------------------------------------------------------------------------- Section 5
                    (261)  261      270       280       290       300       310       325
PI16_Q6UXB8_1      (261)  ETQAPTSLATKDPPSMATEAPPCVTTEVPSILAAHSLPSLDEEPVTFPKSTHVPIPKSADKVTDK
PI16_Q6UXB8_2      (232)  -----------------------------------------------------------------
PI16_Retrogenix    (261)  ETQAPTSLATKDPPSMATEAPPCVTTEVPSILAAHSLPSLDEEPVTFPKSTHVPIPKSADKVTDK ---------------------------------------------------------------------------- Section 6
                    (326)  326      340       350       360       370       380       390
PI16_Q6UXB8_1      (326)  TKVPSRSPENSLDPKMSLTGARELLPHAQEEAEAEAELPPSSEVLASVEPAQDKPGELQATLDHT
PI16_Q6UXB8_2      (232)  -----------------------------------------------------------------
PI16_Retrogenix    (326)  TKVPSRSPENSLDPKMSLTGARELLPHAQEEAEAEAELPPSSEVLASVEPAQDKPGELQATLDHT ---------------------------------------------------------------------------- Section 7
                    (391)  391      400       410       420       430       440       455
PI16_Q6UXB8_1      (391)  GHTSSKSLPNFPNTSATANATGGRALALQSSLPGAEGPDKPSVVSGLNSGPGHVWGPLLGLLLLP
PI16_Q6UXB8_2      (232)  ---------------------------------------AEGPDKPSVVSGLNSGPGHVWGPLLGLLLLP
PI16_Retrogenix    (391)  GHTSSKSLPKFPQYLCHR-----------------------------------------------

---------------------------------------------------------------------------- Section 8
                    (456)  456  463
PI16_Q6UXB8_1      (456)  PLVLAGIF
PI16_Q6UXB8_2      (263)  PLVLAGIF
PI16_Retrogenix    (409)  --------

FIG.4

PI16 ANTIBODIES

CROSS REFERENCE TO RELATED APPLICATIONS

This application is a continuation of U.S. National Phase application filed on Apr. 17, 2019, which was filed under 35 U.S.C. 371 from International Application No. PCT/US2017/060154 filed on Nov. 6, 2017, which in turn claims benefit of U.S. Provisional Application No. 62/42,173 filed Nov. 10, 2016, the contents of each of which is hereby incorporated by reference in its entirety.

REFERENCE TO SEQUENCE LISTING SUBMITTED ELECTRONICALLY

The instant application contains a Sequence Listing which has been submitted electronically in ASCII format and is hereby incorporated by reference in its entirety. The ASCII copy, created on May 9, 2022, is named 24386USCON-SEQLIST.txt and is 77,824 bytes in size.

BACKGROUND OF THE INVENTION

(1) Field of the Invention

The present invention relates to ILT3 and an ILT3 ligand as well as antibodies that bind thereto and methods related thereto. In a specific embodiment the ILT3 ligand is peptidase inhibitor 16 (PI16).

(2) Description of Related Art

Peptidase inhibitor 16 (PI16) is also known as CRISP-9 (cysteine-rich secretory protein 9) or Prostrate Secretory Protein Binding Protein (PSPBP; binds prostate secretory protein 94 (PSP94)). PI16 belongs to cysteine-rich secretory proteins, antigen 5, and pathogenesis-related 1 proteins (CAP) family. Members of this family includes human glioma pathogenesis-related 1 (GLIPR1), Golgi associated pathogenesis related-1 protein (GAPR1), and mannose receptor like and R3H domain containing proteins. PI16 is often found secreted, may have endocrine or paracrine function, or involvement in ECM regulation and branching morphogenesis. The CAP superfamily is suggested to have roles in reproduction, cancer, and immune defense (Gibbs et al., Endocr Rev 29:865-897 (2008)).

ILT3 (Immunoglobulin-like transcript 3), also known as CD85k or LIR-5, is an approximately 60 kDa transmembrane glycoprotein that negatively regulates immune cell activation. Mature human ILT3 has a 238 amino acid extracellular domain with two Ig-like domains, a 21 amino acid transmembrane segment, and a 168 amino acid cytoplasmic domain with 3 immunoreceptor tyrosine-based inhibitory motifs (ITIM). Alternative splicing of human ILT3 generates an isoform that lacks the first ITIM and a secreted isoform that circulates in the serum of cancer patients. ILT3 is expressed on dendritic cells (DCs), monocytes, macrophages, and vascular endothelial cells (ECs). Ligation of ILT3 triggers ITIM-mediated inhibition of cell-activating signaling, leading to enhanced immune tolerance and reduced allogeneic graft rejection. Soluble ILT3 induces the differentiation of CD8+ T suppressor cells (Ts) that can inhibit the effector functions of CD4+ Th cells and CD8+ CTL. In turn, CD8+ Ts cells induce ILT3 up-regulation and a tolerogenic phenotype in monocytes, DCs, and ECs.

Recently, Intl. Pub. No. WO2017015227 reported that CD166, also known as lymphocyte cell adhesion molecule (ALCAM), was a ligand for ILT3 and provides methods for treating cancer comprising in some embodiments an antibody against CD166 or ALCAM.

SUMMARY OF THE INVENTION

The inventors have identified PI16 as a ligand for ILT3 and provides herein antibodies that bind ILT3 in a complex with PI16. Thus, the present invention provides an antibody or antigen-binding fragment that binds to a complex between ILT3 and the ILT3 ligand PI16, which in particular embodiments, does not bind to ILT3 or ILT3 ligand when not in said complex. The present invention also provides a multispecific (e.g., bispecific) antibody or antigen-binding fragment thereof that specifically binds to ILT3 and ILT3 ligand PI16. The present invention further provides a composition comprising an antibody or antigen-binding fragment thereof that specifically binds to ILT3 and an antibody or antigen-binding fragment thereof that specifically binds to ILT3 ligand PI16.

The present invention provides an antibody or antigen-binding fragment that specifically binds to an complex between ILT3 and ILT3 ligand (e.g., PI16) but does not bind to ILT3 or ILT3 ligand which are not in said complex. In an embodiment of the invention, the antibody or antigen-binding fragment thereof comprises a heavy chain variable region comprising: CDR1 comprising the amino acid sequence of SEQ ID NO:10; CDR2 comprising the amino acid sequence of SEQ ID NO:11; CDR3 comprising the amino acid sequence of SEQ ID NO:12; and a light chain variable region comprising: CDR1 comprising the amino acid sequence of SEQ ID NO:13; CDR2 comprising the amino acid sequence of SEQ ID NO:14; CDR3 comprising the amino acid sequence of SEQ ID NO:15; or a heavy chain variable region comprising: CDR1 comprising the amino acid sequence of SEQ ID NO:18; CDR2 comprising the amino acid sequence of SEQ ID NO:19; CDR3 comprising the amino acid sequence of SEQ ID NO:20; and a light chain variable region comprising: CDR1 comprising the amino acid sequence of SEQ ID NO 21; CDR2 comprising the amino acid sequence of SEQ ID NO:22; CDR3 comprising the amino acid sequence of SEQ ID NO:23; or a heavy chain variable region comprising: CDR1 comprising the amino acid sequence of SEQ ID NO:26; CDR2 comprising the amino acid sequence of SEQ ID NO:27; CDR3 comprising the amino acid sequence of SEQ ID NO:28; and a light chain variable region comprising: CDR1 comprising the amino acid sequence of SEQ ID NO:29; CDR2 comprising the amino acid sequence of SEQ ID NO:30; CDR3 comprising the amino acid sequence of SEQ ID NO:31; or a heavy chain variable region comprising: CDR1 comprising the amino acid sequence of SEQ ID NO:34; CDR2 comprising the amino acid sequence of SEQ ID NO:35; CDR3 comprising the amino acid sequence of SEQ ID NO:36; and a light chain variable region comprising: CDR1 comprising the amino acid sequence of SEQ ID NO:37; CDR2 comprising the amino acid sequence of SEQ ID NO:38; CDR3 comprising the amino acid sequence of SEQ ID NO:39. For example, in an embodiment of the invention, the antibody or antigen-binding fragment comprises a heavy chain variable region comprising the amino acid sequence set forth in SEQ ID NO:8; and a light chain variable region comprising the amino acid sequence set forth in SEQ ID NO:9; or a heavy chain variable region comprising the amino acid sequence set forth in SEQ ID NO:16; and a light chain variable region comprising the amino acid sequence set forth in SEQ ID NO:17; or a heavy chain variable region comprising the amino acid sequence set forth in SEQ ID NO:24; and a light chain variable region comprising the amino acid sequence set forth in SEQ ID NO:25; or a heavy chain variable region comprising the amino acid sequence set forth in SEQ ID NO:32; and a light chain variable region comprising the amino acid sequence set forth in SEQ ID NO:33. For example, the present invention provides an antibody or antigen-binding fragment thereof that competes with DX435, DX439 and DX440 or with DX446 for binding to ILT3. The present invention further provides a multispecific (e.g., bispecific) antibody or antigen-binding fragment thereof that specifically binds to ILT3 and ILT3 ligand. Also provided is a composition comprising an antibody or antigen-binding fragment thereof that specifically binds to ILT3 and an antibody or antigen-binding fragment thereof that specifically binds to ILT3 ligand.

The present invention further provides a complex between ILT3 and ILT3 ligand (e.g., PI16), e.g., wherein the ILT3 or ILT3 ligand or both is on the surface of a cell (PI16 on a T-cell and/or ILT3 on a dendritic cell (DC), monocyte, macrophage, or vascular endothelial cell (EC)), detectably labeled (e.g., with a FRET acceptor or FRET donor), bound to a metal surface (e.g., gold or silver), bound to an antibody or antigen-binding fragment, or bound to an insoluble substrate.

The present invention also provides a method for forming a complex between ILT3 and ILT3 ligand (e.g., PI16) comprising contacting the ILT3 and ILT3 ligand under conditions favorable to complex formation; as well as the complex that is the product of this method.

In addition, the present invention provides a method for cross-linking two cells (e.g., a T-cell with a dendritic cell, monocyte, macrophage or vascular endothelial cell) comprising contacting one cell that expresses ILT3 on the cell surface and another cell that expresses ILT3 ligand (e.g., PI16) on the cell surface with a multispecific (e.g., bispecific) antibody or antigen-binding fragment thereof that specifically binds to said ILT3 and said ILT3 ligand.

A method for determining whether ILT3 and an ILT3 ligand (e.g., PI16) bind together is also part of the present invention. The method comprises contacting ILT3 ligand with ILT3 and determining whether the ILT3 ligand and the ILT3 form a complex; wherein, if a complex between the ILT3 ligand and the ILT3 is detected, then the ILT3 ligand and the ILT3 are determined to bind. In an embodiment of the invention, the ILT3 is detectably labeled and wherein the complex is detected by detecting the label bound to the ILT3 ligand; or wherein ILT3 ligand is detectably labeled and wherein the complex is detected by detecting the label bound to the ILT3. In an embodiment of the invention, the ILT3 is labeled with a FRET (fluorescence resonance energy transfer) acceptor and ILT3 ligand is labeled with a FRET donor; or ILT3 is labeled with a FRET donor and ILT3 ligand is labeled with a FRET acceptor; and wherein the complex is determined to form if FRET between the acceptor and donor is detected. In an embodiment of the invention, the ILT3, which is bound to a gold or silver metal surface which is on the surface of a glass slide, in contacted with ILT3 ligand and the metal is illuminated, through the glass, with polarized light wherein, if a change in the refractive index of medium in close vicinity to the metal surface illuminated with the light is detected, then the complex is determined to form; or ILT3 ligand, that is bound to a gold or silver metal surface which is on the surface of a glass slide, in contacted with ILT3 and the metal is illuminated, through the glass, with polarized light wherein, if a change in the refractive index of medium in close vicinity to the metal surface illuminated with the light is detected, then the complex is determined to form.

The present invention also provides a method for determining whether ILT3 and an ILT3 ligand (e.g., PI16) bind together comprising contacting ILT3 ligand that is expressed on the surface of a macrophage cell with ILT3 that is fused to a cytosolic domain of CD3 zeta and is expressed on the surface of a T-cell (e.g., Jurkat cell) that comprises an NFAT promoter operably linked to a reporter gene (e.g., luciferase) wherein binding is determined if reporter gene expression in the T-cell is detected.

The present invention further provides a method for determining whether a substance (e.g., an antibody) agonizes or antagonizes binding between ILT3 and ILT3 ligand (e.g., PI16) comprising contacting ILT3 ligand with ILT3 in the presence of the substance and determining whether the ILT3 ligand and the ILT3 form a complex; wherein the substance is determined to agonize said binding if more of the complex is determined in the presence of the substance than in the absence of the substance and wherein the substance is determined to antagonize said binding if less of the complex is determined in the presence of the substance than in the absence of the substance.

BRIEF DESCRIPTION OF THE DRAWINGS

FIG. 4. Three isoforms of PI16 include a long form with CPI (glycophosphatidylinositol) C-terminal anchor sequence (pI16_Q6UXB8_1; SEQ ID NO:2), a short form, which is a splice variant with deletion of 232 to 424 amino acids but retaining the CPI C-terminal anchor sequence (PI16_Q6UXB8_2; SEQ ID NO:3), and finally, a nearly full length form of 408 amino acids and lacking the CPI C-terminal anchor sequence (PI16_Retrogenix; SEQ ID NO:4).

Figure 1:
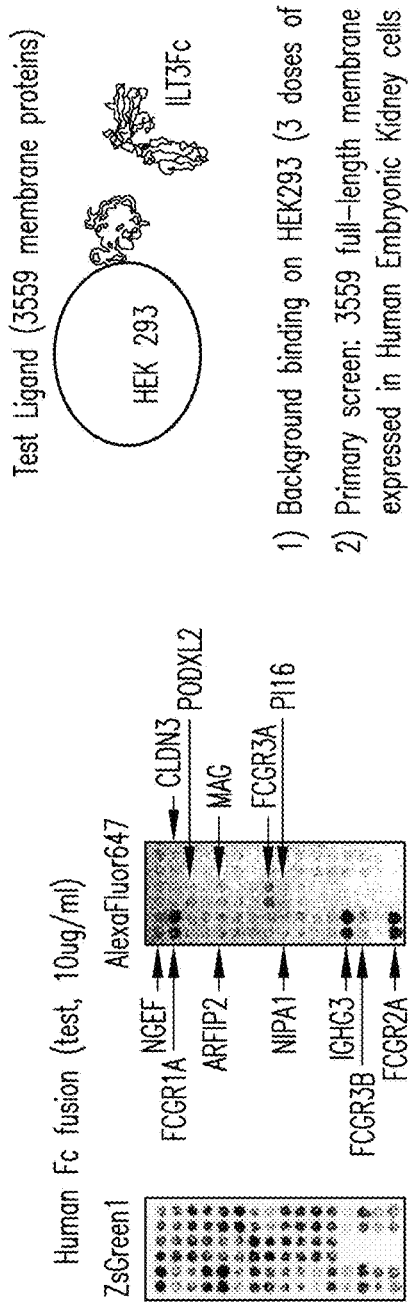
FIG. 1. Cell microarray technology was used to identify specific binding partners for ILT3Fc-fusion protein. 10 µg/ml of ILT3Fc-fusion, labelled "Human Fc fusion (test, 10 um/gl) in FIG. 1, was used for the binding screen against 3559 human plasma membrane proteins, each individually expressed in human HEK293 cells. The primary hit was re-expressed and re-tested with ILT3Fc-fusion, labelled ILT3Fc in FIG. 1, and controls. The confirmation screen yielded six potential hits, including NIPA1 (non-imprinted in Prader-Willi/Angelman syndrome 1), PODXL2 (Podocalyxin-Like 2), MAG (Myelin Associated Glycoprotein), VSIG1 (V-set and immunoglobulin domain containing 1) (not shown), PI16 (Peptidase inhibitor 16), and CLDN3 (Claudin3).

✴=activated dendridic cells (DC); Δ=PI16; ⋏=antibody.

DETAILED DESCRIPTION OF THE INVENTION

The present invention provides PI16, a heretofore an unknown ligand for ILT3. Knowledge of the identity of the ligand for ILT3 is useful as a means for identifying modulators of ILT3 and ILT3 ligand. Such modulators may be used, for example, for therapies for treating diseases such as cancer.

"Isolated" antibodies or antigen-binding fragments thereof, polypeptides, polynucleotides and vectors, are at least partially free of other biological molecules from the cells or cell culture from which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

TABLE 1

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |

TABLE 1-continued

Exemplary Conservative Amino Acid Substitutions

| Original residue | Conservative substitution |
|---|---|
| Thr (T) | Ser |
| Trp (W) | Tyr; Phe |
| Tyr (Y) | Trp; Phe |
| Val (V) | Ile; Leu |

The following references relate to BLAST algorithms often used for sequence analysis: BLAST ALGORITHMS: Altschul et al. (2005) FEBS J. 272(20): 5101-5109; Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

In an embodiment of the invention, the BLAST parameters used when determining the degree of similarity or identity between two sequences are: expect threshold: 10; word size: 3; max matches in a query range: 0; BLOSUM 62 matrix; gap costs: existence 11, extension 1; conditional compositional score matrix adjustment.

Sequence identity refers to the degree to which the amino acids of two polypeptides are the same at equivalent positions when the two sequences are optimally aligned. Sequence similarity includes identical residues and nonidentical, biochemically related amino acids. Biochemically related amino acids that share similar properties and may be interchangeable are discussed in Table 1.

As used herein "specifically binds" refers, with respect to an antigen or molecule such as human ILT3, to the preferential association of an antibody or other ligand, in whole or part, with human ILT3 and not to other molecules, particularly molecules found in human blood or serum. Antibodies typically bind specifically to their cognate antigen with high affinity, reflected by a dissociation constant (KD) of $10^{-7}$ to $10^{-11}$ M or less. Any KD greater than about $10^{-6}$ M is generally considered to indicate nonspecific binding. As used herein, an antibody that "binds specifically" to an antigen refers to an antibody that binds to the antigen and substantially identical antigens with high affinity, which means having a KD of $10^{-7}$ M or less, in particular embodiments a KD of $10^{-8}$ M or less, or $5 \times 10^{-9}$ M or less, or between $10^{-8}$ M and $10^{-11}$ M or less, but does not bind with high affinity to unrelated antigens.

PI16 and ILTs

ILT3 (Immunoglobulin-like transcript 3) is also known by the names LILRB4, CD85K, LIR-5, and leukocyte immunoglobulin like receptor B4. Human ILT3 precursor protein comprises the amino acid sequence set forth in SEQ ID NO:1. In the mature form of the human ILT3 molecule, the amino acid sequence lacks the 21 amino acid N-terminal signal (leader) sequence (SEQ ID NO:41). The extracellular domain of the human ILT3 comprises amino acids 22-259 of SEQ ID NO:1.

Human PI16 is also known as Peptidase inhibitor 16, CRISP-9 or PSPBP. In an embodiment of the invention, human PI16 exists in three isoforms: long (full length) isoform, short isoform, and a secreted isoform. The long isoform precursor amino acid sequence is shown in SEQ ID NO:2 and the amino acid sequence of the mature form lacking the 27 amino acid signal sequence is shown in SEQ ID NO:42. The short isoform precursor amino acid sequence is shown in SEQ ID NO:3 and the amino acid sequence of the mature form lacking the 27 amino acid signal sequence is shown in SEQ ID NO:43. The short isoform lacks amino acids 232 through 424. The secreted isoform precursor amino acid sequence is shown in SEQ ID NO:4 and the amino acid sequence of the mature form lacking the 27 amino acid signal sequence is shown in SEQ ID NO:44. The secreted isoform lacks the C-terminal glycophosphatidylinositol (GPI) anchor sequence.

Human ILT11 (also known as LILRA5) precursor comprises the amino acid sequence shown in SEQ ID NO:6 and SEQ ID:45 shows the mature form lacking the 41 amino acid signal sequence.

Human ILT8 (also known as LILRA6) comprises the amino acid sequence shown in SEQ ID NO:7 and SEQ ID:46 shows the mature form lacking the 21 amino acid signal sequence.

The present invention includes a complex between ILT3 and ILT3 ligand (e.g., PI16), for example, in the presence of an antibody or antigen-binding fragment thereof that binds to the ILT3/PI16 complex, or ILT3 or PI16 or both. In an embodiment of the invention, an antibody or fragment binds the ILT3/ILT3 ligand complex but not to ILT3 or ILT3 ligand alone.

ILT3 or an ILT3 ligand includes variants as well as fragments (e.g., truncations) thereof which comprise sequence identity/similarity to ILT3 or ILT3 ligand and which are capable for forming a complex. A "variant" of a polypeptide (e.g., ILT3 or ILT3 ligand (e.g., PI16)) comprises an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence such as SEQ ID NO:1, 2, 3 or 4 that is set forth herein; when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment). In an embodiment of the invention, the ILT3 or ILT3 ligand variant comprises 1, 2, 3, 4, 5, 6, 7, 8, 9 or 10 substitutions, e.g., conservative substitutions, for example, relative to that of SEQ ID NO:1, 2, 3 or 4. As used herein, the term ILT3 ligand excludes CD166.

Antibodies and Antigen-Binding Fragments Thereof

The present invention provides antibodies and antigen-binding fragments thereof that bind to ILT3 (e.g., human ILT3) or an ILT3 ligand (e.g., PI16 (e.g., human PI16)) or both or to a complex between ILT3 and ILT3 ligand (e.g., PI16). Such antibodies or fragments, in an embodiment of the invention, antagonize or agonize the binding between ILT3 and ILT3 ligand (e.g., PI16).

The present invention includes multispecific antibodies and antigen-binding fragments thereof that bind to both ILT3 and ILT3 ligand (e.g., PI16). Multispecific (e.g., bispecific) antibodies that bind to both ILT3 ligand (e.g., PI16) on a macrophage and ILT3 on a T-cell, and, for example, enhance the association between the macrophage and T-cell are also within the scope of the present invention, as is such a cell/multispecific antibody complex.

In an embodiment of the invention, an antibody or antigen-binding fragment thereof of the present invention specifically binds to ILT3, but also binds to ILT3, ILT8 and/or ILT11 and/or, in an embodiment of the invention, does not bind specifically to ILT4. In an embodiment of the invention, such an antibody or antigen-binding fragment, which specifically binds to ILT3, ILT8 and/or ILT11, but not to ILT4 is DX446, DX435, DX439 or DX440. In an embodiment of the invention, the antibody is a variant of DX446, DX435, DX439 or DX440 having a heavy chain CDR1, CDR2 and/or CDR3 that comprises the amino acid sequence set forth in Table 2 or an amino acid having at least about 90% (e.g., 91, 92, 93, 94, 95, 096, 97, 98, 99%) amino acid sequence identity or similarity thereto or having 1, 2, 3, 4, 5, 6, 7, 8, 9 or 10 conservative amino acid substitutions relative to the corresponding amino acid sequence set forth in Table 2. In an embodiment of the invention, the antibody is a variant of DX446, DX435, DX439 or DX440 having a light chain CDR1, CDR2 and/or CDR3 that comprises the amino acid sequence set forth in Table 2 or an amino acid having at least about 90% (e.g., 91, 92, 93, 94, 95, 096, 97, 98, 99%) amino acid sequence identity or similarity thereto or having 1, 2, 3, 4, 5, 6, 7, 8, 9 or 10 conservative amino acid substitutions relative to the corresponding amino acid sequence set forth in Table 2. In an embodiment of the invention, the antibody is a variant of DX446, DX435, DX439 or DX440 having a light chain variable region that comprises the amino acid sequence set forth in Table 2 or an amino acid having at least about 90% (e.g., 91, 92, 93, 94, 95, 096, 97, 98, 99%) amino acid sequence identity or similarity thereto or having 1, 2, 3, 4, 5, 6, 7, 8, 9 or 10 conservative amino acid substitutions relative to the corresponding amino acid sequence set forth in Table 2. In an embodiment of the invention, the antibody is a variant of DX446, DX435, DX439 or DX440 having a heavy chain variable region that comprises the amino acid sequence set forth in Table 2 or an amino acid having at least about 90% (e.g., 91, 92, 93, 94, 95, 096, 97, 98, 99%) amino acid sequence identity or similarity thereto or having 1, 2, 3, 4, 5, 6, 7, 8, 9 or 10 conservative amino acid substitutions relative to the corresponding amino acid sequence set forth in Table 2.

An "anti-ILT3/ILT3 ligand" (e.g., "anti-ILT3/PI16") antibody or antigen-binding fragment binds to both ILT3 and ILT3 ligand and, optionally, to another epitope. The term includes multispecific (e.g., bispecific) antibodies and antigen-binding fragments.

Antagonism of binding between ILT3 ligand (e.g., PI16) and ILT3 refers to reduction of such binding, e.g., as measured by any assay such as an in vitro cell binding assay between two cells expressing ILT3 and ILT3 ligand (e.g., PI16). Also, agonism of binding between ILT3 ligand (e.g., PI16) and ILT3 refers to the increase of such binding, e.g., as measured by any assay such as an in vitro cell binding assay between two cells expressing ILT3 and ILT3 ligand (e.g., PI16). Antagonism or agonism of binding can be determined using any of the methods for determining such binding that are discussed herein.

A multivalent antibody or antigen-binding fragment is an antibody or fragment comprising two or more antigen binding sites. A bivalent antibody or antigen-binding fragment includes, for example, a full antibody which has two antigen-binding arms. The present invention includes multivalent, e.g., bivalent antibodies and antigen-binding fragments thereof.

A multispecific antibody or antigen-binding fragment thereof binds to more than one epitope, e.g., 2, 3 or 4. For example, a bispecific antibody is an example of a multispecific antibody. The present invention includes such multispecific antibodies and fragments that bind to ILT3 and ILT3 ligand (e.g., PI16) and, optionally, to another epitope.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989).

The present invention includes monoclonal anti-ILT3, anti-ILT3 ligand (e.g., anti-PI16) and anti-ILT3/ILT3 ligand (e.g., anti-ILT3/PI16) antibodies and antigen-binding fragments thereof including multispecific antibodies and fragments as well as monoclonal compositions comprising a plurality of isolated monoclonal antibodies and antigen-binding fragments thereof. The term "monoclonal antibody", as used herein, refers to a population of substantially homogeneous antibodies, i.e., the antibody molecules comprising the population are identical in amino acid sequence except for possible naturally occurring mutations that may be present in minor amounts. A "plurality" of such monoclonal antibodies and fragments in a composition refers to a concentration of identical (i.e., as discussed above, in amino acid sequence except for possible naturally occurring mutations that may be present in minor amounts) antibodies and fragments which is above that which would normally occur in nature, e.g., in the blood of a host organism such as a mouse or a human. In contrast, conventional (polyclonal) antibody preparations typically include a multitude of different antibodies having different amino acid sequences in their variable domains, particularly their CDRs, that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624-628 (1991) and Marks et al., J. Mol. Biol. 222: 581-597 (1991), for example. See also Presta, J. Allergy Clin. Immunol., 116:731 (2005).

The present invention includes anti-ILT3, anti-ILT3 ligand (e.g., anti-PI16) and anti-ILT3/ILT3 ligand (e.g., anti-ILT3/PI16) chimeric antibodies (e.g., human constant domain/mouse variable domain) and methods of use thereof. As used herein, a "chimeric antibody" is an antibody having the variable domain from a first antibody and the constant domain from a second antibody, where the first and second antibodies are from different species. (U.S. Pat. No. 4,816,567; and Morrison et al., Proc. Natl. Acad. Sci. USA 81: 6851-6855 (1984)). Typically, the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g., mouse) antibody.

The present invention includes anti-ILT3, anti-ILT3 ligand (e.g., anti-PI16) and anti-ILT3/ILT3 ligand (e.g., anti-ILT3/PI16) humanized antibodies and antigen-binding fragments thereof (e.g., mouse antibodies that have been humanized) and methods of use thereof. As used herein, the term "humanized antibody" refers to forms of antibodies that contain sequences from both human and non-human (e.g., mouse or rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

The present invention includes anti-ILT3, anti-ILT3 ligand (e.g., anti-PI16) and anti-ILT3/ILT3 ligand (e.g., anti-ILT3/PI16) recombinant antibodies and antigen-binding fragments thereof and methods of use thereof. There are several methods by which to produce recombinant antibodies which are known in the art. One example of a method for recombinant production of antibodies is disclosed in U.S. Pat. No. 4,816,567.

The present invention includes anti-ILT3, anti-ILT3 ligand (e.g., anti-PI16) and anti-ILT3/ILT3 ligand (e.g., anti-ILT3/PI16) fully human antibodies and antigen-binding fragments thereof and methods of use thereof. The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only. In an embodiment of the invention, an fully human anti-ILT3, anti-PI16 and anti-ILT3/PI16 antibody or antigen-binding fragment thereof is the product of isolation from a transgenic animal, e.g., a mouse (e.g., a HUMAB mouse, see e.g., U.S. Pat. Nos. 5,545,806; 5,569, 825; 5,625,126; 5,633,425; 5,661,016; 5,770,429; 5,789, 650; 5,814,318; 5,874,299 and 5,877,397; and Harding, et al., (1995) Ann. NY Acad. Sci. 764:536 546; or a XENO-MOUSE, see e.g., Green et al., 1999, J. Immunol. Methods 231:11-23), which has been genetically modified to have fully human immunoglobulin genes; or the product of isolation from a phage or virus which expresses the immunoglobulin chains.

The present invention includes anti-ILT3, anti-ILT3 ligand (e.g., anti-PI16) and anti-ILT3/ILT3 ligand (e.g., anti-ILT3/PI16) antigen-binding fragments and methods of use thereof. As used herein, unless otherwise indicated, "antibody fragment" or "antigen-binding fragment" refers to antigen-binding fragments of antibodies, i.e. antibody fragments that retain the ability to bind specifically to the antigen bound by the full-length antibody, e.g. fragments that retain one or more CDR regions. Examples of antigen-binding fragments include, but are not limited to, Fab, Fab', F(ab')2, and Fv fragments; diabodies; single-chain antibody molecules, e.g., sc-Fv and multispecific antibodies formed from antibody fragments.

The present invention includes anti-ILT3, anti-ILT3 ligand (e.g., anti-PI16) and anti-ILT3/ILT3 ligand (e.g., anti-ILT3/PI16) Fab fragments and methods of use thereof. A "Fab fragment" is comprised of one light chain and the $C_H1$ and variable regions of one heavy chain. The heavy chain of a Fab molecule cannot form a disulfide bond with another heavy chain molecule. An "Fab fragment" can be the product of papain cleavage of an antibody.

The present invention includes anti-ILT3, anti-PI16 and multispecific anti-ILT3/PI16 antibodies and antigen-binding fragments thereof which comprise an Fc region and methods of use thereof. An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

The present invention includes anti-ILT3, anti-ILT3 ligand (e.g., anti-PI16) and anti-ILT3/ILT3 ligand (e.g., anti-ILT3/PI16) Fab' fragments and methods of use thereof. A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

The present invention includes anti-ILT3, anti-ILT3 ligand (e.g., anti-PI16) and anti-ILT3/ILT3 ligand (e.g., anti-ILT3/PI16) F(ab')$_2$ fragments and methods of use thereof. A "F(ab')$_2$ fragment" contains two light chains and two heavy chains containing a portion of the constant region between the $C_{H1}$ and $C_{H2}$ domains, such that an interchain disulfide bond is formed between the two heavy chains. A F(ab')$_2$ fragment thus is composed of two Fab' fragments that are held together by a disulfide bond between the two heavy chains. An "F(ab')$_2$ fragment" can be the product of pepsin cleavage of an antibody.

The present invention includes anti-ILT3, anti-ILT3 ligand (e.g., anti-PI16) and anti-ILT3/ILT3 ligand (e.g., anti-ILT3/PI16) scFv fragments and methods of use thereof. The "Fv region" comprises the variable regions from both the heavy and light chains, but lacks the constant regions.

The present invention includes anti-ILT3, anti-ILT3 ligand (e.g., anti-PI16) and anti-ILT3/ILT3 ligand (e.g., anti-ILT3/PI16) scFv fragments and methods of use thereof. The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen-binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO88/01649 and U.S. Pat. Nos. 4,946,778 and 5,260,203.

Eukaryotic and prokaryotic host cells, including mammalian cells as hosts for expression of the anti-ILT3, anti-ILT3 ligand (e.g., anti-PI16) and anti-ILT3/ILT3 ligand (e.g., anti-ILT3/PI16) antibodies and antigen-binding fragments thereof and immunoglobulin chains thereof (e.g., heavy chain and/or light chain) disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens, Pichia sp., any Saccharomyces sp., Hansenula polymorpha, any Kluyveromyces sp., Candida albicans, any Aspergillus sp., Trichoderma reesei, Chrysosporium lucknowense, any Fusarium sp., Yarrowia lipolytica,* and *Neurospora crassa*. Host cells including anti-ILT3, anti-ILT3 ligand and anti-ILT3/ILT3 ligand antibodies and antigen-binding fragments are part of the present invention.

Further, expression of antibodies and antigen-binding fragments thereof and immunoglobulin chains of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. Thus, in an embodiment of the invention, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell.

The present invention includes methods for purifying an anti-ILT3, anti-ILT3 ligand (e.g., anti-PI16) and anti-ILT3/ILT3 ligand (e.g., anti-ILT3/PI16) antibody or antigen-binding fragment thereof of the present invention comprising introducing a sample (e.g., culture medium, cell lysate or cell lysate fraction, e.g., a soluble fraction of the lysate) comprising the antibody or fragment to a purification medium (e.g., cation-exchange medium, anion-exchange medium, hydrophobic exchange medium, affinity purification medium (e.g., protein-A). In an embodiment of the invention, the medium is in a column to which the sample is applied. In an embodiment of the invention, the purification method is conducted following recombinant expression of the antibody or fragment in a host cell, e.g., wherein the host cell is first lysed and, optionally, the lysate is purified of insoluble materials prior to purification on a medium; or wherein the antibody or fragment is secreted into the culture medium by the host cell and the medium or a fraction thereof is applied to the purification medium.

Figure 7:
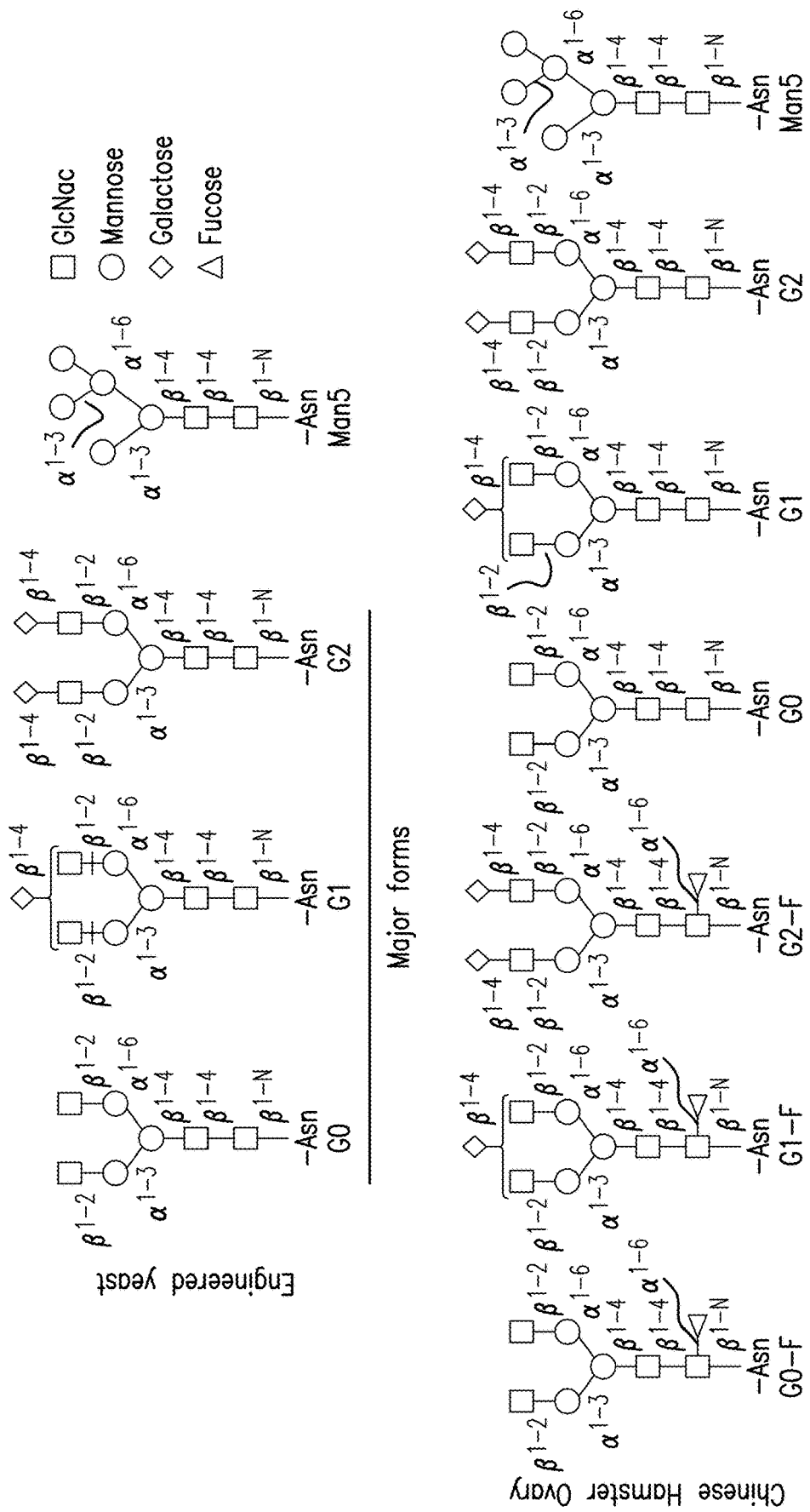
FIG. 7. Major N-linked glycans produced in glycoengineered *Pichia pastoris* host cells and in Chinese hamster ovary cells (CHO).

The present invention includes anti-ILT3, anti-ILT3 ligand (e.g., anti-PI16) and anti-ILT3/ILT3 ligand (e.g., anti-ILT3/PI16) antibodies or antigen-binding fragments comprising N-linked glycans that are typically added to immunoglobulins produced in Chinese hamster ovary cells (CHO N-linked glycans) or to engineered yeast cells (engineered yeast N-linked glycans), such as, for example, *Pichia pastoris*. See FIG. 7. For example, in an embodiment of the invention, the antibody or antigen-binding fragment comprises one or more of the "engineered yeast N-linked glycans" or "CHO N-linked glycans" that are set forth in FIG. 8 (e.g., G0 and/or G0-F and/or G1 and/or G1-F and/or and/or G2-F and/or Man5). In an embodiment of the invention, the antibody or antigen-binding fragment comprises the engineered yeast N-linked glycans, i.e., G0 and/or G1 and/or G2, optionally, further including Man5. In an embodiment of the invention, the antibody or antigen-binding fragment comprise the CHO N-linked glycans, i.e., G0-F, G1-F and G2-F, optionally, further including G0 and/or G1 and/or G2 and/or Man5. In an embodiment of the invention, about 80% to about 95% (e.g., about 80-90%, about 85%, about 90% or about 95%) of all N-linked glycans on the antibody or antigen-binding fragment immunoglobulin chains are engineered yeast N-linked glycans or CHO N-linked glycans. See Nett et al. Yeast. 28(3): 237-252 (2011); Hamilton et al. Science. 313(5792): 1441-1443 (2006); Hamilton et al. Curr Opin Biotechnol. 18(5): 387-392 (2007). For example, in an embodiment of the invention, an engineered yeast cell is GFI5.0 or YGLY8316 or strains set forth in U.S. Pat. No. 7,795,002 or Zha et al. Methods Mol Biol. 988:31-43 (2013). See also international patent application publication no. WO2013/066765.

In one embodiment, the anti-ILT3, anti-ILT3 ligand (e.g., anti-PI16) and anti-ILT3/ILT3 ligand (e.g., anti-ILT3/PI16) antibodies or antigen-binding fragments comprises a heavy chain constant region, e.g. a human constant region, such as γ1, γ2, γ3, or γ4 human heavy chain constant region or a variant thereof. In another embodiment, the anti-ILT3, anti-PI16 or multispecific anti-ILT3/PI16 antibodies or antigen-binding fragments comprises a light chain constant region, e.g. a human light chain constant region, such as lambda or kappa human light chain region or variant thereof. In an embodiment of the invention, the Fc region of the antibody is γ4 with a Ser228Pro mutation (Schuurman, Jet. al., *Mol. Immunol.* 38: 1-8, 2001).

In particular embodiments, the present invention provides the above antibody or antigen binding fragment wherein the antibody comprises a human IgG1, IgG2, IgG3, or IgG4 heavy chain (HC) constant domain or variant thereof comprising 1, 2, 3, 4, 5, 6, 7, 8, 9, or 10 amino acid substitutions, additions, deletions, or combinations thereof compared to the amino acid sequence of the native IgG1, IgG2, IgG3, or IgG4 isotype.

In some embodiments, different constant domains may be fused to a $V_L$ and $V_H$ regions comprising the CDRs provided herein. In particular embodiments, the $V_L$ and $V_H$ regions comprising the CDRs provided herein may be fused to a human IgG1, IgG2, IgG3, or IgG4 heavy chain (HC) constant domain or variant thereof comprising 1, 2, 3, 4, 5, 6, 7, 8, 9, or 10 amino acid substitutions, additions, deletions, or combinations thereof compared to the amino acid sequence of the native or wild-type IgG1, IgG2, IgG3, or IgG4 isotype.

In particular embodiments the anti-ILT3 antibody (or antigen binding fragment) has an altered effector function and may comprise a heavy chain constant domain other than native (wild-type) human IgG1, for example a human IgG1 that has mutations that abrogate or minimize one or more effector functions, including ability to bind complement, human IgG4, or a hybrid human IgG1/human IgG4.

Although native human IgG1 antibodies provide for long half-life and for effector functions, such as complement activation and antibody-dependent cellular cytotoxicity, such activities may not be desirable for all uses of an antibody. Thus, in particular embodiments, it is desirable that the heavy chain constant domain or Fc have minimal or reduced effector function ("effector-less"). In those instances, the anti-ILT3 HC variable domain may be fused to a human IgG4 constant domain, which is generally known to be effector-less, or an IgG1 constant domain that has been mutated to be rendered effecter-less. These effector-less molecules have minimal or reduced binding to human FcγRIIIA, and FcγRIIA, and Fcγ. RI compared to the polypeptide comprising the wildtype IgG Fc region, wherein the affinity to each of human FcγRIIIA, and FcγRIIA, and FcγRI is reduced by 1.15-fold to 100-fold compared to the polypeptide comprising the wildtype IgG constant domain, and wherein the antibody-dependent cell-mediated cytotoxicity (ADCC) induced by said molecule is 0-20% of the ADCC induced by the polypeptide comprising the wild-type human IgG1 constant domain.

Therefore in particular embodiments, the present invention includes chimeric or humanized anti-ILT3 antibodies and antigen-binding fragments thereof that comprise a human IgG4 constant domain. In a further embodiment, the human IgG4 constant domain may be modified to differ from the native (wild-type) human IgG4 constant domain (Swiss-Prot Accession No. P01861.1) at a position corresponding to position 228 in the EU system and position 241 in the KABAT system in which the native serine at position 108 (Ser108) of the HC constant domain is replaced with proline (Pro), see for example SEQ ID NO:56. This modification prevents formation of a potential inter-chain disulfide bond between the cysteine at position 106 (Cys106) and the cysteine at position 109 (Cys109), which correspond to positions Cys226 and Cys229 in the EU system and positions Cys239 and Cys242 in the KABAT system, which may interfere with proper intra-chain disulfide bond formation. See Angal et al. Mol. Imunol. 30:105 (1993); see also (Schuurman et. al., Mol. Immunol. 38: 1-8, (2001); SEQ ID NOs:14 and 41). In particular embodiments, the human IgG4 constant domain may further include in addition to the S228P substitution an L235E substitution.

In another embodiment, the chimeric or humanized anti-ILT3 antibody may be fused to a modified human IgG1 constant domain, which has been modified to be effector-less. In one embodiment, the human IgG1 HC may include substitutions of human IgG2 HC residues at positions 233-236 and IgG4 HC residues at positions 327, 330, and 331 to greatly reduce ADCC and CDC (Armour et al., Eur J Immunol. 29(8):2613-24 (1999); Shields et al., J Biol Chem. 276(9):6591-604(2001)). In particular embodiments, the antibody comprises a human IgG1 heavy chain (HC) constant domain or variant thereof comprising 1, 2, 3, 4, 5, 6, 7, 8, 9, or 10 amino acid substitutions, additions, deletions, or combinations thereof compared to the amino acid sequence of the native IgG, which provides an antibody having reduced or minimal effector function. In particular aspects, the IgG1 has been modified to comprise or consist of an L234A, an L235A, and a D265S mutation to render the Fc effector-less (SEQ ID NO:57). Other mutations that may be used to render an IgG1 Fc effector-less may be found in U.S. Pat. No. 8,969,526.

In another embodiment, the human IgG1 HC is modified to lack N-glycosylation of the asparagine (Asn) residue at around position 297 of the HC. The consensus sequence for N-glycosylation is Asn-Xaa-Ser/Thr (wherein Xaa is any amino acid except Pro); in IgG1 the N-glycosylation consensus sequence is Asn-Ser-Thr. The modification may be achieved by replacing the codon for the Asn at position 297 in the nucleic acid molecule encoding the HC with a codon for another amino acid, for example Gln. Alternatively, the codon for Ser may be replaced with the codon for Pro or the codon for Thr may be replaced with any codon except the codon for Ser, e.g. N297A or N297D. Such modified IgG1 molecules have little or no detectable effector function. Alternatively, all three codons are modified.

In another embodiment, the human IgG1 constant domain is modified to include one or more amino acid substitutions selected from E233P, L234A, L235A, L235E, N297A, N297D, D265S, and P331S, wherein the residues are numbered according to the EU index of Kabat, and wherein said polypeptide exhibits a reduced affinity to the human FcγRIIIA and/or FcγRIIA and/or FcγRI compared to a polypeptide comprising the wildtype IgG constant domain region. In particular embodiments, the human IgG constant domain comprises substitutions of L234A, L235A, and D265S as illustrated by SEQ ID NO:57, for example. In particular embodiments, the human IgG1 constant domain comprises an amino acid substitution at position Pro329 and at least one further amino acid substitution E233P, L234A, L235A, L235E, N297A, N297D, D265S, and P331S. These and other substitutions are disclosed in WO9428027; WO2004099249; WO20121300831, U.S. Pat. Nos. 9,708,406; 8,969,526; 9,296,815; Sondermann et al. Nature 406, 267-273 (20 Jul. 2000)).

The present invention further provides a composition comprising any one of the aforementioned antibodies and a pharmaceutically acceptable carrier. In particular embodiments, the composition comprises a mixture of antibodies comprising a heavy chain having a C-terminal lysine and antibodies comprising a heavy chain lacking a C-terminal lysine. In particular embodiments, the composition comprises an antibody disclosed herein wherein the predominant antibody form comprises a heavy chain having a C-terminal lysine. In particular embodiments, the composition comprises an antibody disclosed herein wherein the predominant antibody form comprises a heavy chain lacking a C-terminal lysine. In particular embodiments, the composition comprises an antibody disclosed herein wherein about 100% of the antibodies in the composition comprise a heavy chain lacking a C-terminal lysine.

Assays

The present invention includes a method for forming a complex between ILT3 ligand (e.g., PI16) and ILT3 comprising contacting the ILT3 and ILT3 ligand (e.g., PI16) under conditions favorable to binding and complex formation. In an embodiment of the invention, the ILT3 is on the surface of a cell such as a macrophage. In an embodiment of the invention, the ILT3 ligand (e.g., PI16) is on the surface of a cell such as a T-cell. In an embodiment of the invention, the ILT3 and/or ILT3 ligand (e.g., PI16) is not on the surface of a cell, e.g., is soluble or tethered to an insoluble support (e.g., polycarbonate, polystyrene, polypropylene, polyethlene, glass, nitrocellulose, dextran, nylon, polyacrylamide or agarose). In an embodiment of the invention, the ILT3 is labeled with a FRET donor and the ILT3 ligand is labeled with FRET acceptor; or the ILT3 ligand is labeled with a FRET donor and the ILT3 is labeled with FRET acceptor. In an embodiment of the invention, the ILT3 or ILT3 ligand is bound to a metal surface (e.g., gold or silver metal) on an transparent surface (e.g., glass slide). In an embodiment of the invention, the ILT3 and/or ILT3 ligand in the complex is bound to one or more antibodies or antigen-binding fragments thereof (e.g., anti-ILT3, anti-ILT3 ligand or bispecific anti-ILT3/ILT3 ligand). Complexes comprising such ILT3 and ILT3 ligand are part of the present invention. In an embodiment of the invention, the complex is the product of a process of forming the complex as described herein.

The present invention also provides a method for determining whether ILT3 and ILT3 ligand (e.g., PI16) bind together, for example, under a given set of test conditions, e.g., in the presence of a test substance or at a given pH, salt concentration, temperature or buffer concentration. In an embodiment of the invention, the method comprises contacting said ILT3 ligand (e.g., PI16) with said ILT3 under the conditions to be tested and determining binding between the ILT3 ligand (e.g., PI16) and ILT3. If a complex between ILT3 ligand (e.g., PI16) and ILT3 is present, then the ILT3 ligand (e.g., PI16) and ILT3 are determined to bind under those conditions (e.g., in the presence of the test substance). In an embodiment of the invention, the ILT3 or ILT3 ligand (e.g., PI16) or both are on a cell surface, e.g., wherein ILT3 ligand (e.g., PI16) is on a T-cell surface and/or wherein ILT3 is on the macrophage cell surface. In an embodiment of the invention, the ILT3 or ILT3 ligand (e.g., PI16) or both are not on a cell surface, e.g., are soluble or are bound to a solid, insoluble substrate (e.g., polycarbonate, polystyrene, polypropylene, polyethlene, glass, nitrocellulose, dextran, nylon, polyacrylamide or agarose).

Methods for determining whether a substance agonizes or antagonizes such binding can also be performed by determining such binding in the presence of the substance; wherein the substance antagonizes the binding if less binding is observed in the presence of the substance than in the absence of the substance; and the substance agonizes the binding if more binding is observed in the presence of the substance than in the absence of the substance. Such substances can be tested for agonism or antagonism using any of the binding assay methods set forth herein.

The present invention can also be used to identify substances that reduce immune tolerance, reduce Ts (T suppressor cell) differentiation, reduce inhibition of CD4+Th activation, reduce inhibition of CD8+ cytotoxic T lymphocyte (CTL) activation. Substances that antagonize ILT3/ILT3 ligand complex formation may be determined to have one or more of these characteristics.

A "substance" to be tested in an assay set forth herein can be a small organic molecule, an antibody or an antigen-binding fragment of an antibody.

The present invention provides a method for determining whether ILT3 binds with ILT3 ligand (e.g., PI16) comprising contacting a cell, e.g., a HEK293 cell or a 3A9 cell, that expresses PI16 on the cell surface, with ILT3 fused to an Fc that is bound by an anti-Fc antibody (e.g., anti-human IgG Fcγ-specific antibody) which is detectably labeled, e.g., with phycoerythrin, and determining whether the cell is labeled with the detectable label. If the cell is determined to be labeled with the detectable label, then the ILT3 and ILT3 ligand (e.g., PI16) are determined to bind.

A detectable label can be any label whose presence in a composition can be determined. For example, a detectable label can be a polypeptide to which, for example, ILT3 or ILT3 ligand (e.g., PI16) is fused, e.g., a radiolabel (e.g., $^{3}H$, $^{35}S$, $^{32}P$, $^{14}C$ or $^{131}I$), epitope tag (e.g., a FLAG tag such as DYKDDDDK (SEQ ID NO:5)), Fc, glutathione-S-transferase (GST).

The present invention provides a method for determining whether ILT3 binds with ILT3 ligand (e.g., PI16) comprising contacting a cell that expresses ILT3 ligand (e.g., PI16) on the cell surface, e.g., a human embryonic kidney cell (HEK293T) cell, with a cell that expresses ILT3 on the cell surface, e.g., a T-cell such as a Jurkat cell, wherein the ILT3 on the cell surface is fused to a cytosolic CD3z (CD3zeta) domain and wherein that cell includes a reporter gene, e.g., luciferase or green fluorescent protein (GFP), linked to a CD3z-responsive promoter (such as an NFAT (nuclear factor of activated T-cells) promoter). Cross-linking to CD3z induces NFAT promoter expression and, in turn, reporter expression. If expression of the reporter gene is detected, then the ILT3 and ILT3 ligand (e.g., PI16) are determined to bind.

The present invention provides a method for determining whether ILT3 binds with ILT3 ligand (e.g., PI16) by use of fluorescence resonance energy transfer (FRET). FRET utilizes energy transferred between donor and acceptor molecules that are in close proximity. If a ligand labeled with a FRET acceptor is bound to a receptor labeled with a FRET donor, then the acceptor will fluoresce when excited. In general, when using FRET, there should be a distance smaller than 10 nm between the acceptor and donor, in addition to an overlapping absorption spectrum between acceptor and donor. The method comprises labeling ILT3 with the acceptor and ILT3 ligand (e.g., PI16) with the donor (or vice versa), incubating the labeled ILT3 and labeled ILT3 ligand (e.g., PI16) and determining if there is light emitted as a result of fluorescence resonance energy transfer between the acceptor and donor. In an embodiment of the invention the donor/acceptor pair used in the method is as follows:
fluorescein/tetramethylrhodamine; IAEDANS/fluorescein; EDANS/Dabcyl;
fluorescein/fluorescein; BODIPY FL/BODIPY FL; fluorescein/QSY 7; or fluorescein/QSY 9 dyes.

The present invention provides a method for determining whether ILT3 binds with ILT3 ligand (e.g., PI16) by use of surface plasmon resonance (SPR). SPR does not require labeling of the ILT3 or ILT3 ligand. The surface plasmon resonance device is an optical biosensor that measures binding events of biomolecules (e.g., ILT3 and PI16) at a metal surface by detecting changes in the local refractive index. SPR technology exploits surface plasmons (electromagnetic waves) that can be excited at certain metal interfaces, e.g., silver and gold. When incident light is coupled with the metal interface at angles greater than the critical angle, the reflected light exhibits a sharp attenuation (SPR minimum) in reflectivity owing to the resonant transfer of energy from the incident light to a surface plasmon. Binding of the biomolecules at the surface changes the local refractive index and results in a shift of the SPR minimum. By monitoring changes in the SPR signal, it is possible to measure binding activities at the surface in real time. For example, binding of ILT3 on the surface by ILT3 ligand (or vice versa) will create an SPR signal. For example, ILT3, that is bound to a gold or silver metal surface which is on the surface of a glass slide, is contacted with ILT3 ligand (e.g., PI16) and the metal is illuminated, through the glass, with polarized light wherein, and, if a change in the refractive index of medium in close vicinity to the metal surface illuminated with the light is detected, then the complex is determined to form; or ILT3 ligand, that is bound to a gold or silver metal surface which is on the surface of a glass slide, is contacted with ILT3 and the metal is illuminated, through the glass, with polarized light wherein, if a change in the refractive index of medium in close vicinity to the metal surface illuminated with the light is detected, then the complex is determined to form.

The present invention provides a method for determining whether ILT3 binds with ILT3 ligand (e.g., PI16) by use of immunoprecipitation (IP). The method comprises contacting ILT3 and ILT3 ligand (e.g., PI16), binding the ILT3 with an antibody or antigen-binding fragment thereof which is immobilized to a solid phase (e.g., an insoluble bead or matrix such as agarose or glass); removing the bound ILT3 from the solid phase and determining the presence of ILT3 ligand (e.g., PI16) wherein the ILT3 and ILT3 ligand (e.g., PI16) are determined to bind if the ILT3 ligand (e.g., PI16) is detected in the presence of the ILT3. In an embodiment of the invention, the method comprises contacting ILT3 and ILT3 ligand (e.g., PI16), binding the ILT3 ligand (e.g., PI16) with an antibody or antigen-binding fragment thereof which is immobilized to a solid phase (e.g., an insoluble bead or matrix such as agarose or glass); removing the bound ILT3 ligand (e.g., PI16) from the solid phase and determining the presence of ILT3 wherein the ILT3 and ILT3 ligand (e.g., PI16) are determined to bind if the ILT3 is detected in the presence of the ILT3 ligand (e.g., PI16).

Pharmaceutical Compositions and Administration

To prepare pharmaceutical or sterile compositions of the anti-ILT3, anti-ILT3 ligand (e.g., anti-PI16) and anti-ILT3/ILT3 ligand (e.g., anti-ILT3/PI16) antibodies (e.g., humanized antibodies such as antagonist humanized antibodies) and antigen-binding fragments thereof, the antibody or antigen-binding fragment thereof is admixed with a pharmaceutically acceptable carrier or excipient. See, e.g., Remington's Pharmaceutical Sciences and U.S. Pharmacopeia: National Formulary, Mack Publishing Company, Easton, Pa. (1984). Such compositions are part of the present invention.

The scope of the present invention includes dessicated, e.g., freeze-dried, compositions comprising an anti-ILT3, anti-ILT3 ligand (e.g., anti-PI16) and anti-ILT3/ILT3 ligand (e.g., anti-ILT3/PI16) antibody or antigen-binding fragment thereof or a pharmaceutical composition thereof that includes a pharmaceutically acceptable carrier but substantially lacks water.

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, NY).

Toxicity and therapeutic efficacy of the antibody or fragment compositions, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with an anti-ILT3, anti-ILT3 ligand (e.g., anti-PI16) and anti-ILT3/ILT3 ligand (e.g., anti-ILT3/PI16) (e.g., humanized antibody such as antagonist humanized antibodies) or antigen-binding fragment thereof disclosed herein is administered to the subject in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

The present invention provided methods for administering an anti-ILT3, anti-ILT3 ligand (e.g., anti-PI16) and anti-ILT3/ILT3 ligand (e.g., anti-ILT3/PI16) antibody or antigen-binding fragment thereof comprising introducing the antibody or fragment into the body of a subject. For example, the method comprises piercing the body of the subject with a needle of a syringe and injecting the antibody or fragment into the body of the subject, e.g., into the vein, artery, tumor, muscular tissue or subcutis of the subject.

The present invention provides a vessel (e.g., a plastic or glass vial, e.g., with a cap or a chromatography column, hollow bore needle or a syringe cylinder) comprising any of the antibodies or antigen-binding fragments, polypeptides or polynucleotides set forth herein or a pharmaceutical composition thereof comprising a pharmaceutically acceptable carrier.

The present invention also provides an injection device comprising any of the antibodies or antigen-binding fragments set forth herein or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., comprising the antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$) and optionally including glucose) introduced into the body of the patient through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Alternately, one may administer the anti-ILT3, anti-ILT3 ligand (e.g., anti-PI16) and anti-ILT3/ILT3 ligand (e.g., anti-ILT3/PI16) antibody (e.g., humanized antibody such as antagonist humanized antibodies) or antigen-binding fragment in a local rather than systemic manner, for example, via injection of the antibody or fragment directly into a tumor. Furthermore, one may administer the antibody or fragment in a targeted drug delivery system, for example, in a liposome coated with a tissue-specific antibody, targeting, for example, a tumor. The liposomes will be targeted to and taken up selectively by the afflicted tissue. Such methods and liposomes are part of the present invention.

"Treat" or "treating" means to administer anti-ILT3, anti-ILT3 ligand (e.g., anti-PI16) and anti-ILT3/ILT3 ligand (e.g., anti-ILT3/PI16) antibodies or antigen-binding fragments thereof of the present invention, to a subject having one or more symptoms of a disease for which the antibodies and antigen-binding fragments are effective, e.g., in the treatment of a subject having cancer or an infectious disease, or being suspected of having cancer or infectious disease, for which the agent has therapeutic activity. Typically, the antibody or fragment is administered in an "effective amount" or "effective dose" which will alleviate one or more symptoms (e.g., of cancer or infectious disease) in the treated subject or population, whether by inducing the regression or elimination of such symptoms or by inhibiting the progression of such symptom(s), e.g., cancer symptoms such as tumor growth or metastasis, by any clinically measurable degree. The effective amount of the antibody or fragment may vary according to factors such as the disease stage, age, and weight of the patient, and the ability of the drug to elicit a desired response in the subject.

Determination of the appropriate dose is made by the clinician, e.g., using parameters or factors known or suspected in the art to affect treatment. Generally, in determining the dose, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies are may be desirable. Guidance in selecting appropriate doses of anti-LAG3 antibodies or fragments is available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, NY; Bach (ed.) (1993) Monoclonal Antibodies and Peptide Therapy in Autoimmune Diseases, Marcel Dekker, New York, NY; Baert et al. (2003) New Engl. J. Med. 348:601-608; Milgrom et al. (1999) New Engl. J. Med. 341:1966-1973; Slamon et al. (2001) New Engl. J. Med. 344:783-792; Beniaminovitz et al. (2000) New Engl. J. Med. 342:613-619; Ghosh et al. (2003) New Engl. J. Med. 348: 24-32; Lipsky et al. (2000) New Engl. J. Med. 343:1594-1602).

Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

Further provided are methods for treating or preventing cancer in subjects, such as human subjects, in need of such treatment by administering an effective amount of the anti-ILT3, anti-ILT3 ligand (e.g., anti-PI16) and anti-ILT3/ILT3 ligand (e.g., anti-ILT3/PI16) antibodies or antigen-binding fragments thereof of the present invention which are disclosed herein which may be effective for such treatment or prevention. In an embodiment of the invention, such a subject suffers from and is treated for cancer, e.g., a solid tumor which includes, in addition to the tumor cells, tumor infiltrating lymphocytes (TILs), such as T-cells, expressing LAG3.

The present invention also provides methods for treating or preventing an infectious disease in a subject by administering an effective amount of anti-ILT3, anti-ILT3 ligand (e.g., anti-PI16) and anti-ILT3/ILT3 ligand (e.g., anti-ILT3/PI16) antibodies or antigen-binding fragments thereof disclosed herein to the subject which may be effective for such treatment or prevention. In an embodiment of the invention, the infectious disease is viral infection. In an embodiment of the invention, the infectious disease is bacterial infection. In an embodiment of the invention, the infectious disease is parasitic infection. In an embodiment of the invention, the infectious disease is fungal infection.

EXAMPLES

These examples are intended to exemplify the present invention are not a limitation thereof. Compositions and methods set forth in the Examples form part of the present invention.

Example 1

Discovery of ILT3 Ligand

Cell microarray technology was used to identify specific binding partners for an ILT3Fc-fusion protein. PI16 was discovered to be an ILT3 binding partner. See FIG. 1. Background binding tests showed dose-dependent levels of background binding of the test ligand to untransfected HEK293 cells. Based upon this, 10 µg/mL of the test protein was selected for the binding screen against 3559 human plasma membrane proteins, each individually expressed in human HEK293 cells. This revealed 42 primary hits, many of which were of weak or very weak intensity. Each primary hit was re-expressed and tested with the test ligand and controls. A positive control ligand: receptor interaction (CTLA4-hFc:CD86) was used to confirm the screening and detection conditions. The confirmation screen yield six potential hits, including NIPA1 (non-imprinted in Prader-Willi/Angelman syndrome 1), PODXL2 (Podocalyxin-Like 2), MAG (Myelin Associated Glycoprotein), VSIG1 (V-set and immunoglobulin domain containing 1), PI16 (Peptidase inhibitor 16), and CLDN3 (Claudin3).

Figure 2:
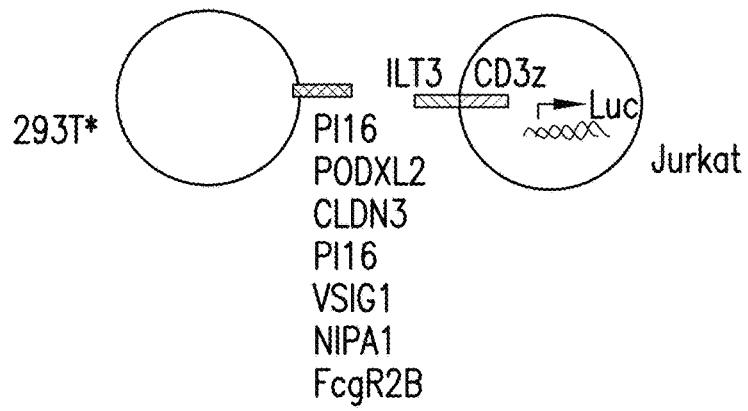
FIG. 2. The potential hits were validated by transient expression of cDNA vectors on 293T cells and co-culture with an ILT3 signaling reporter cell line. FcγR2B vector transfected cells served as a control. An ILT3 reporter cell line was constructed by fusing the extracellular domains of ILT3 with the intracellular signaling domain of CD3z chain. The reporter cells also contained an NFAT transcription factor-dependent luciferase gene. Upon ILT3-CD3z co-ligation, NFAT activation led to transcription and production of luciferase (not shown).
Figure 3:
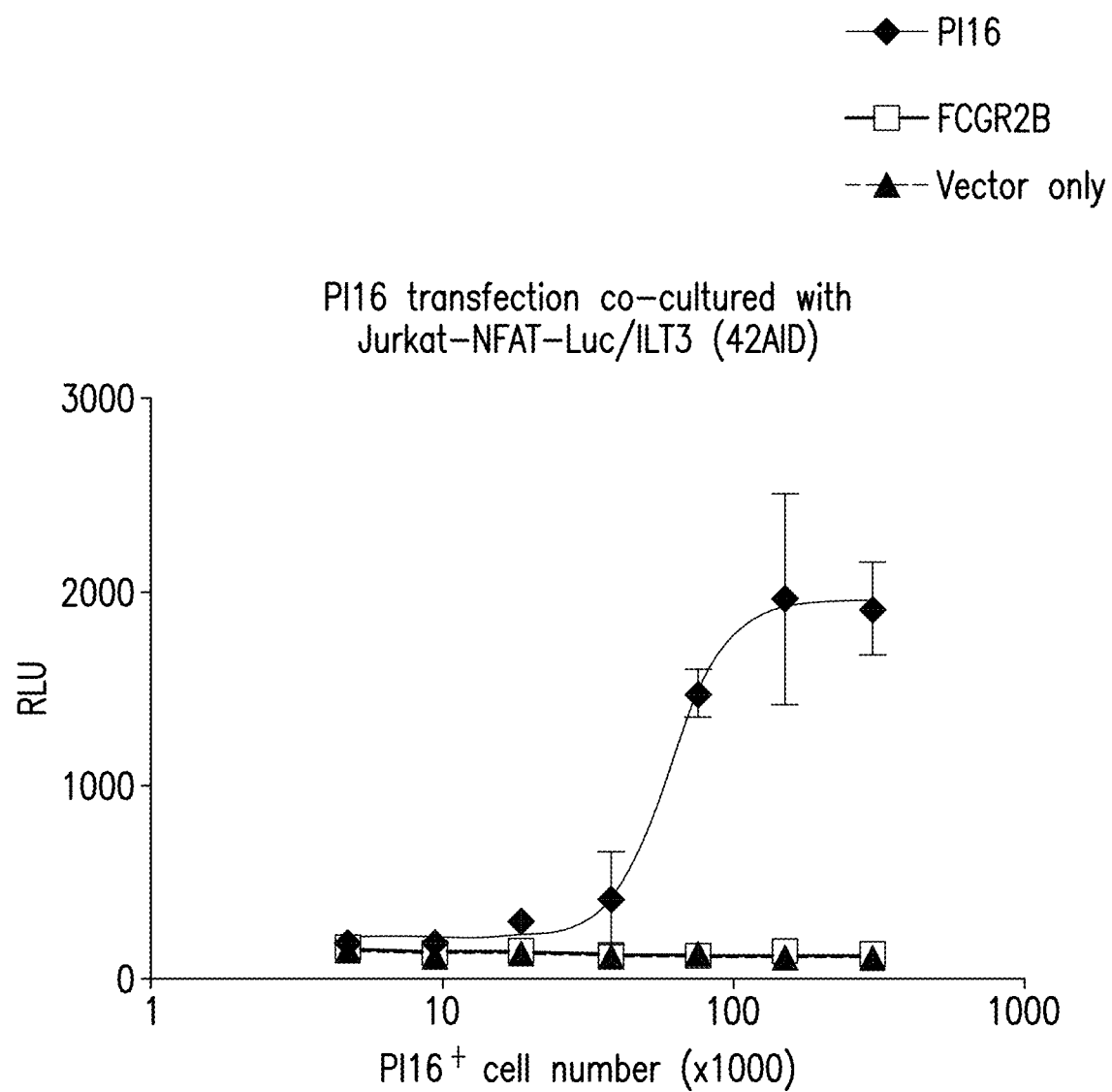
FIG. 3. cDNA vectors of the 6 potential hits were transiently expressed on HEK293T cells. Transfected cells (3e5: 2 fold titration) were co-cultured with ILT3-CD3z-luciferase reporter cells. PI16 expressed on the 293T cells activated ILT3 associated CD3z-NFAT-Luciferase activity (data shown; diamonds). None of the other expression vectors including FcγR2B control vector or vector-only control induced luciferase activity.

Hits were validated by transient expression of cDNA vectors on HEK293T (human embryonic kidney) cells and co-cultured with an ILT3 signaling reporter cell line. See FIG. 2. FcγR2B vector transfected cells served as a control. An ILT3 reporter cell line was constructed by linking the extracellular domains of ILT3 with the intracellular signaling domain of CD3z chain (ILT3-fusion protein). The reporter cells also contained an NFAT transcription factor-dependent luciferase gene sequence. Upon ILT3-CD3z co-ligation, NFAT signaling led to transcription and production of luciferase. It was shown that PI16 expressing cells promoted a 2 log increase in luciferase activity of ILT3 reporter cells suggesting that PI16 expressed on the 293T cells were able to "co-ligate" ILT3 and drive CD3z-NFAT-Luciferase activity. In contrast, none of the other expression vectors including FcγR2B vectors induced any luciferase activities. See FIG. 3.

PI16 is expressed by a subset of human memory Treg with enhanced migration to CCL17 and CCL20. It was shown by microarray analysis to be over-expressed by CD4-positive/CD25-positive Treg compared with CD4-positive/CD25-negative Th cells. However, while PI16 serves as a marker for a small subset of inflammatory tissue infiltrating Treg cells, there has been no known function for PI16 on lymphocytes. (Cell Immunol. 2012 January-February; 275(1-2): 12-8). As shown in FIG. 4, PI16 has 3 isoforms, including a long form with C-terminal GPI anchor sequence, a short splice variant with deletion of 232 to 424 amino acids but retaining the C-terminal anchor sequence (270 amino acids), and finally, a nearly full length form that lacks the C-terminal anchor sequence.

Figure 5:
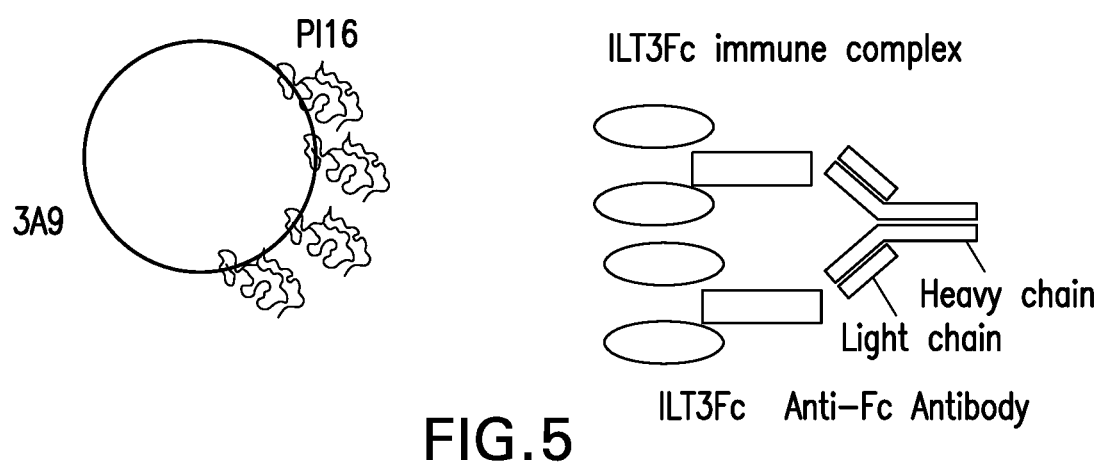
FIG. 5. A cartoon showing 3A9 cells that had been transfected with cDNA encoding PI16 expressing PI16 on the cell surface and ILT3Fc Immune Complex comprising ILT3Fc cross-linked to goat anti-human IgG Fc gamma specific antibody to form an ILT3Fc Immune Complex. The cells expressing PI16 are then reacted with the ILT3Fc Immune Complex and the bound ILT3Fc Immune Complex was detected with goat anti-mouse IgG, F(ab')₂ PE conjugated antibody. Mouse VISTA-Fc was used as an irrelevant control.
Figure 6:
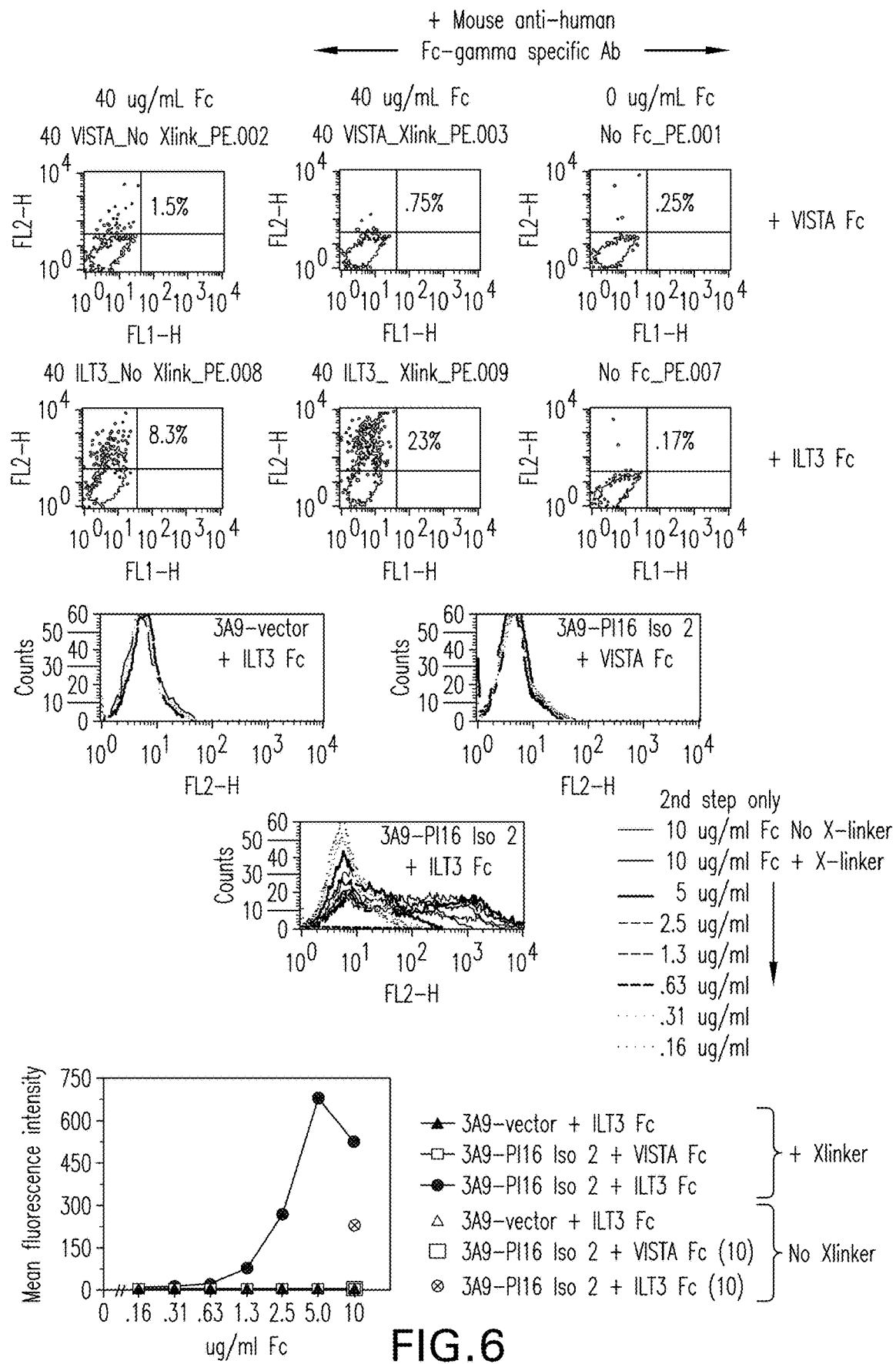
FIG. 6. Top panel shows ILT3Fc (but not mouse VISTA-Fc) binds PI16 transfectin (8.3%). When ILT3Fc was cross-linked with mouse anti-human Fc mAb, the staining increased to 23%. The mouse anti-human Fc did not bind the PI16 expressing cells in the absence of ILT3Fc (0.17%). Lower panels show ILT3Fc titration from 10 μg/mL to 0.16 μg/mL. PE-labelled Goat anti-human IgG Fc gamma-specific antibody was used as a second step stain. Mouse VISTA-Fc was an irrelevant control and the parental 3A9 cells transfected with control vector do not bind ILT3Fc.

To directly demonstrate the PI16 interaction with ILT3, PI16 was transfected into 3A9 cells and ILT3Fc alone or ILT3Fc crosslinked with a goat anti-human IgG Fc gamma specific antibody were used to stain the PI16 positive cells as illustrated in FIG. 5. ILT3Fc has the amino acid sequence set forth in SEQ ID NO:47, which shows the mature ILT3Fc protein. ILT3Fc alone stained PI16 transfectins (8.3%). ILT3Fc complex showed enhanced staining to PI16$^+$ cells (23%). ILT3Fc was titrated from 10 µg/mL to 0.16 µg/mL with 2.5 to 5 µg/mL yielding the best staining. Mouse VISTA-Fc was used as an irrelevant staining control and the parental 3A9 cells transfected with control vector do not bind ILT3Fc. The data clearly showed that ILT3Fc can directly bind PI16 expressed on cell surface. See FIG. 6.

Example 2

Production of Anti-ILT3 Antibodies

Antibodies that bind specifically to ILT3 were made and characterized.

Antibody isolation. Six- to eight-week-old female Balb/c mice (Taconic Biosci.) were immunized in the right hind leg footpad with 5 µg of ILT3 (amino acid #22-259, GenBank: ABM86208.1) human IgG1 fusion protein (CH2 and CH3 of hIgG1) in PBS mixed with Sigma Adjuvant System (Sigma cat #S6322-1VL) at a 1:1 ratio (v/v). The first 6 doses of human ILT3Fc protein were administered every 3 to 4 days. The last 4 doses were given once every week. Mice were sacrificed 3 days later and cells were isolated from draining inguinal lymph node.

Lymphocytes were fused by electrofusion to a mouse myeloma cell line, P3X (ATCC), based upon standard protocols. Cells were plated at approximately $2 \times 10^5$ cells/mL in a flat bottom microtiter plate, followed by a two week incubation in DMEM/F12 selective hybridoma medium containing 15% Fetal Bovine Serum, 1 ng/mL recombinant murine IL-6 (R&D), 1×Penicillin-Streptomycin-Glutamine (Life Technologies), 1 mM sodium pyruvate (Life Technologies), 1% OPI Media Supplement (Sigma) and 1× HAT (Sigma). After two weeks, cells were cultured in medium in which the HAT is replaced with HT (Sigma). The resulting hybridomas were then screened for the production of ILT3-specific antibodies.

Supernatants from individual wells were first screened by ELISA for anti-ILT3 monoclonal IgG antibodies. Nunc MaxiSorp flat-bottom 96-well plates (Thermo Scientific) were coated overnight at 4° C. with either 1 μg/mL human ILT3Fc or human IgG1 control. After washing with PBS+ 0.05% Tween 20 for 3 times, 50 μL of hybridoma supernatant was added to the wells. After 2 hours of incubation at 37° C., plates were washed and 50 μL of 1:4000 HRP-conjugated goat anti-mouse IgG antibody (Southern Biotech cat #1043-05) was added to the wells, followed by 2 hours of incubation at 37° C. 100 μL of TMB substrate (Pierce) were added to the wells after washing. Reaction was developed after 10 to 15 minutes and stopped by 100 μL of 0.16 M sulfuric acid (Life technologies). Plates were read at 450 nm absorbance. From the primary screening, 239 wells were selected for secondary screening based on absorbance reading greater than 0.7 for ILT3Fc (less than 50% positivity for corresponding IgG1 control).

Secondary screening was performed on human monocytes from PBMCs by flow cytometry. Human monocytes were reported to express a high level of ILT3 and the result was confirmed by staining the cells with commercially available ILT3 antibody (eBioscience, clone ZM4.1). Before staining, cells were pre-incubated with 0.2 μg of goat IgG to block human Fc receptors for 15 minutes at 4° C. Then 80 μL of the hybridoma supernatants was added to each well and incubated for 30 mins at 4° C. After washing the cells, PE-conjugated goat anti-mouse IgG was added to detect the presence of the ILT3 antibodies. Stained cells were analyzed by FACS LSR. Negative population was defined by adding PE-conjugated goat anti-mouse IgG to the cells without the hybridoma supernatants; there was no signal in the PE channel. Positive wells were expanded in preparation for cloning.

Expanded wells were screened again on human monocytes by flow cytometry as illustrated above. Cells from positive wells were diluted to 3 cells/mL and 100 μL aliquots were plated in each well for a total of five flat-bottom 96-well plates. After two weeks, supernatants were collected and screened by flow cytometry on THP-1 cells, a human monocyte cell line that has been reported to express high level of ILT3 and the result was confirmed by staining the cells with commercially available ILT3 antibody (eBioscience, clone ZM4.1).

Binding affinity. The Pall ForteBio Octet instrument uses disposable fiber-optic sensors that detect biomolecular interactions using a proprietary biolayer interferometry. It is a dip-and-read system where ligand-coated sensor tips are immersed in analyte-containing wells of a microplate. The Octet can be used to run epitope binning assays for the characterization of antibodies. One binning assay format is the tandem assay where the antigen is immobilized onto a biosensor and then presented to the two competing antibodies in consecutive steps. Binding to distinct non-overlapping epitopes is indicated if saturation with the first antibody (Ab1) does not block binding of the second antibody (Ab2). Antibodies are tested in a pair-wise combinatorial manner and those which compete for the same binding site are grouped into the same bin.

Instrument. Octet QK384

Anti-ILT3 antibody samples. Antibodies were provided as hybridoma supernatants with estimated antibody concentrations (determined by Octet quantitation methods).

Binding assay. Anti-ILT3 antibodies were first tested to ensure binding to human ILT3/human IgG. The running buffers for testing antibody supernatants were production medium and 1× Kinetics Buffer (diluted from 10× Kinetics Buffer, ForteBio Cat #18-5032), respectively. Anti-human Fc (AHC) biosensors (ForteBio Cat #18-5060) were pre-wet for 5 minutes in running buffer then dipped into same (60 s) to establish a baseline. Human ILT3/human IgG (40 nM, 600 s) was immobilized on the tips, then dipped into the anti-ILT3 antibody (167 nM, 600 s), and finally immersed back into running buffer to observe dissociation (300 s) of antibody from ligand.

Binning assay. Anti-ILT3 antibodies were binned by tandem assay. Anti-human Fc (AHC) biosensors (ForteBio Cat #18-5060) were pre-wet for 5 minutes in running buffer (refer to Binding Assay) then dipped into same (60 s) to establish a baseline. Human ILT3/human IgG (40 nM, 600 s) was immobilized on the tips and then dipped into the first antibody (167 nM, 300 or 600 s) followed by the second antibody (167 nM, 120 s).

Binning analysis. Binning results were analyzed using the epitope binning features available in ForteBio Octet Data Analysis software v8.0. Two-dimensional matrices are generated to analyze the pair-wise combinations for blocking status. In the matrices, the rows represent Ab1 and the columns represent competing Ab2. A cell represents an antibody pair and is color-coded by its blocking status where one color designates blocked pairs and another color designates non-blocking pairs. This aids to summarize antibodies into appropriate epitope bins.

Cross-competition assay to determine epitope similarity. To determine whether the anti-ILT3 antibodies recognized similar epitope, a two-step binding assay was performed. The biosensor with immobilized ILT3Fc picked up the first antibody and then was dipped into the various secondary antibodies. If the epitope of the second antibody was similar to the first antibody, then there was no additional signal. If the epitope of the second antibody was different than the first antibody, additional signal was recorded since the second antibody can still bind to the exposed epitope not bound by the first antibody. Overall, Octet data demonstrated that DX435, DX439 and DX440 fell into one bin while DX446 fell into another.

Example 3

Identification of Anti-ILT3 Antibodies that Block PI16 Binding and Function

The capacity of anti-ILT3 antibodies—identified in Example 2—to inhibit PI16 binding was tested. In general, there were 3 bins for the way anti-ILT3 antibodies interacted with PI16. Some of the antibodies did not affect ILT3 binding to PI16 (e.g., 11G3, 31G11, which have similar binding as isotype control mAbs). Some antibodies were partial blockers (e.g., Ab1 and Ab2, which have lower binding compared to isotype controls). Finally, there were three unique antibodies that completely blocked ILT3 binding to PI16 (Ab3-5).

Example 4

Treatment of Tumor-Bearing CD34 Humanized Mice with Anti-ILT3 Antibody

CD34 humanized mice (NSG mice, The Jackson Laboratory) were injected subcutaneously on the left flank with 1.5×10⁶ SKMEL5 tumor cells, a melanoma cell line obtained from ATCC. Intraperitoneal treatment of either isotype (mouse IgG1K) or test antibodies at 50 mpk (mg per kg) was given when tumor size reached 100-130 mm³. Second treatment dose was given 7 days after the initial dose. Each experimental group consisted of 4 animals. Tumor growth was recorded every 7 days. Once treatment started, tumor growth was recorded every 4 days. Mice were sacrificed 7 days after the second treatment dose.

Figure 8:
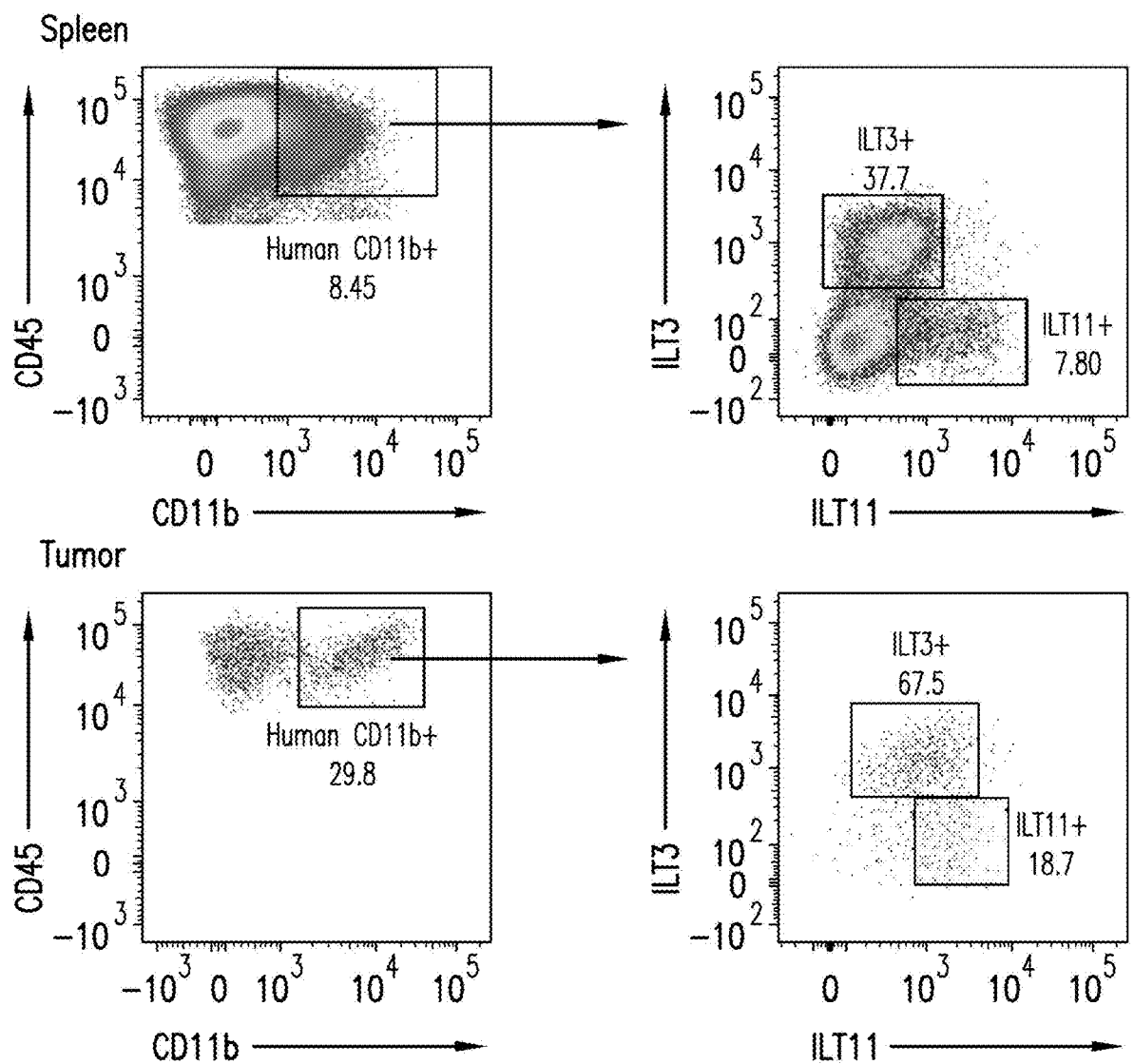
FIG. 8. CD34 humanized mice (NSG mice, The Jackson Laboratory) were injected subcutaneously on the left flank with 1.5×10⁶ SKMEL5 tumor cells, a melanoma line obtained from ATCC. A phenotypic profile of human CD11b+ myeloid cells in spleen and tumor from SK-MEL-5 tumor bearing mice. Proportions of CD11b+ myeloid cells expressing ILT3 and ILT11 were determined. Result showed that ILT3 and ILT11 were expressed on a different subset of CD11b+ myeloid cells.

A phenotypical profile of human CD11b+ myeloid cells in spleen and tumor from SKMEL5 tumor bearing mouse is set forth in FIG. 8. Proportions of ILT3+ and ILT11+CD11b+ myeloid cells were determined. Results showed that ILT3 (ITIM containing inhibitory receptor) and ILT11 (associates with ITAM activating receptor) are expressed on a different subsets of CD11b+ myeloid cells. These two subsets of immune cells may have distinct function based on their expression of an immune inhibitory versus activation receptors.

Figure 9:
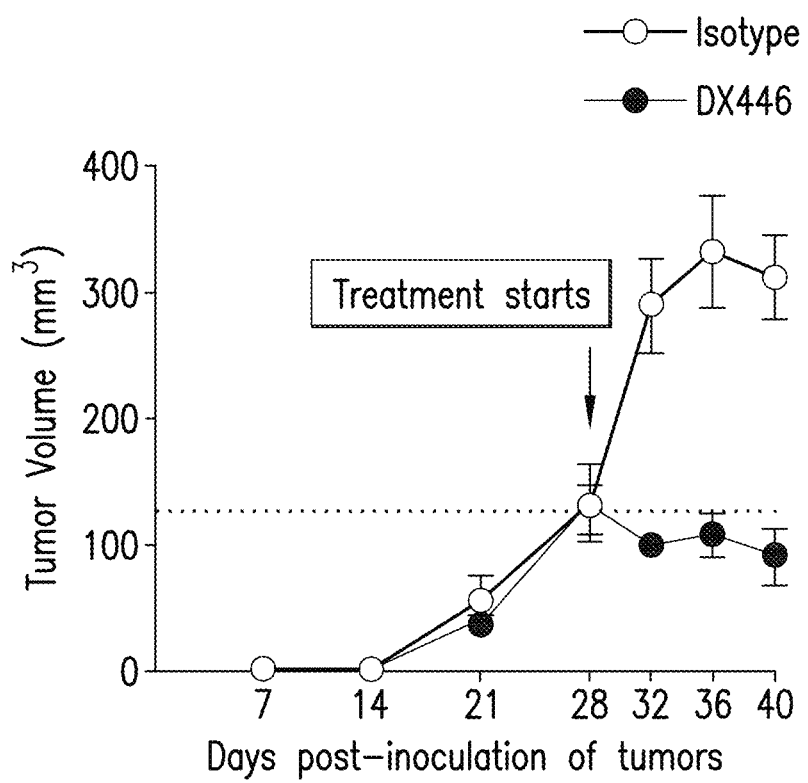
FIG. 9. Anti-ILT3 (DX446) treatment led to tumor growth inhibition. Tumor growth was measured in CD34 stem cell engrafted humanized mice transplanted with SKMEL5 and treated with either isotype (n=4, white circles), or DX446 (n=4, black circles) at 50 mg per kg (mpk). Two out of the 4 tumors in the DX446 treated groups regressed, while the other 2 tumors showed growth inhibition. Error bars represent SEM.

Anti-ILT3 (DX446) treatment led to tumor growth inhibition. Tumor growth was measured in CD34 humanized mice transplanted with SKMEL5 and treated with either isotype (n=4, white circle) or DX446 (n=4, black circle) at 50 mpk. Two out of the 4 tumors in the DX446 treated groups regressed (See FIG. 9). Results are representative of 3 separate experiments. Error bars represent SEM.

Figure 10:
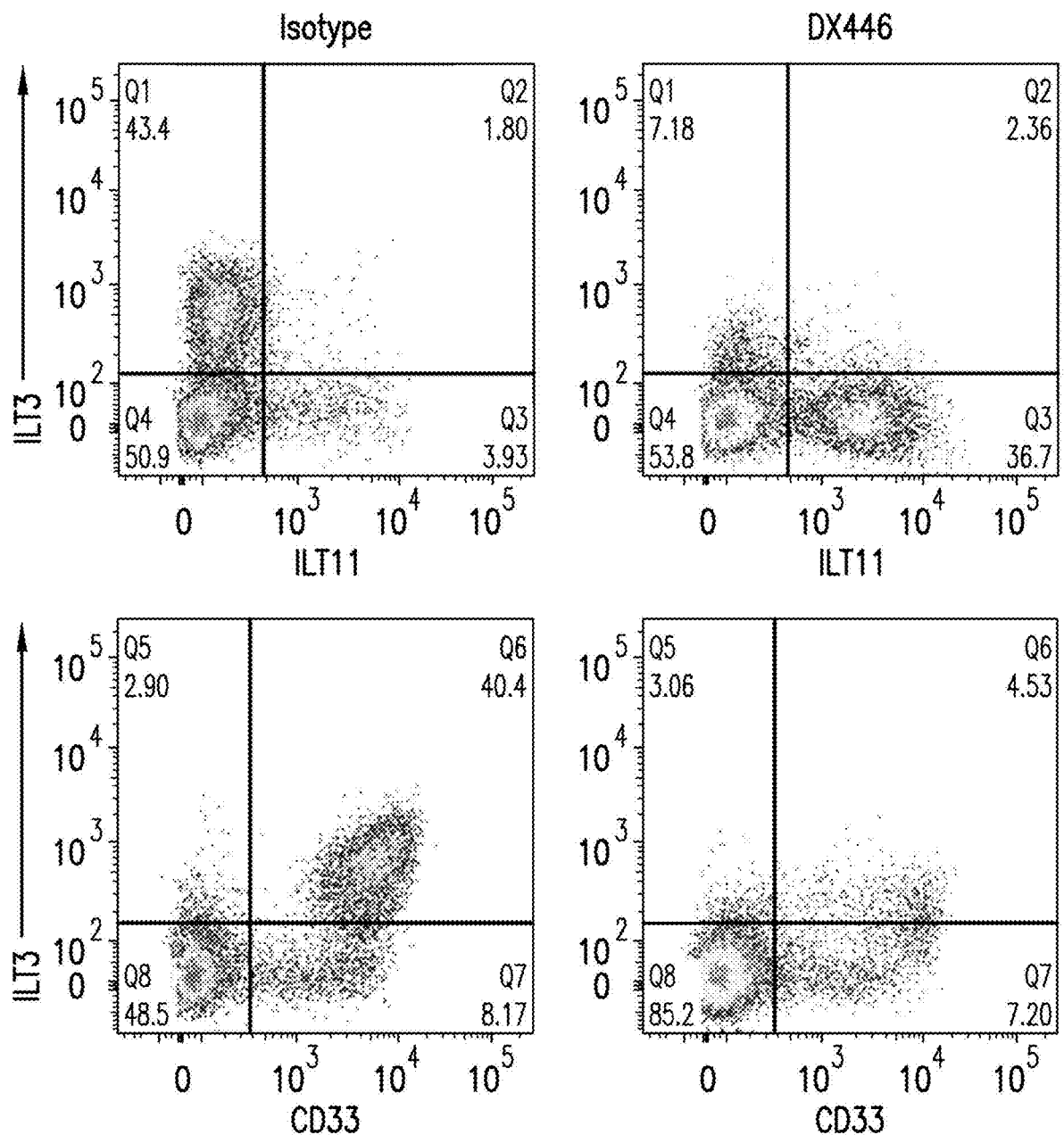
FIG. 10. Anti-ILT3 (DX446) treatment of SKMEL5 tumor bearing mice reduced the number of CD11b+, ILT3+, CD33+ myeloid cells. Splenocytes from either isotype or DX446 treated mice were isolated. Cells were stained with anti-ILT3, anti-ILT11 and anti-CD33 antibodies and analyzed by flow cytometry. Expression of ILT3, ILT11 and CD33 on myeloid cells, gated as CD11b+ cells is shown.

To determine whether the effect of tumor inhibition correlated with a switch in myeloid cell phenotype, we isolated splenocytes and compared ILT3, ILT11, and CD33 expression. After anti-ILT3 (DX446) treatment, there was a significant increase in ILT11-expressing myeloid cells along with a decrease in ILT3 and CD33-expressing cells (see FIG. 10). ILT11 is associated with immunoreceptor tyrosine-based activation motif (ITAM) and promotes activating signals to myeloid cells. In contrast, both ILT3 and CD33 contain immunoreceptor tyrosine-based inhibition motifs (ITIM) and are suppressive. Therefore after anti-ILT3 treatment, the myeloid cell compartment skewed toward a proinflammatory phenotype.

Example 5

Anti-PD1 Activated T Cells have Enhanced PI16 Expression

Figure 11:
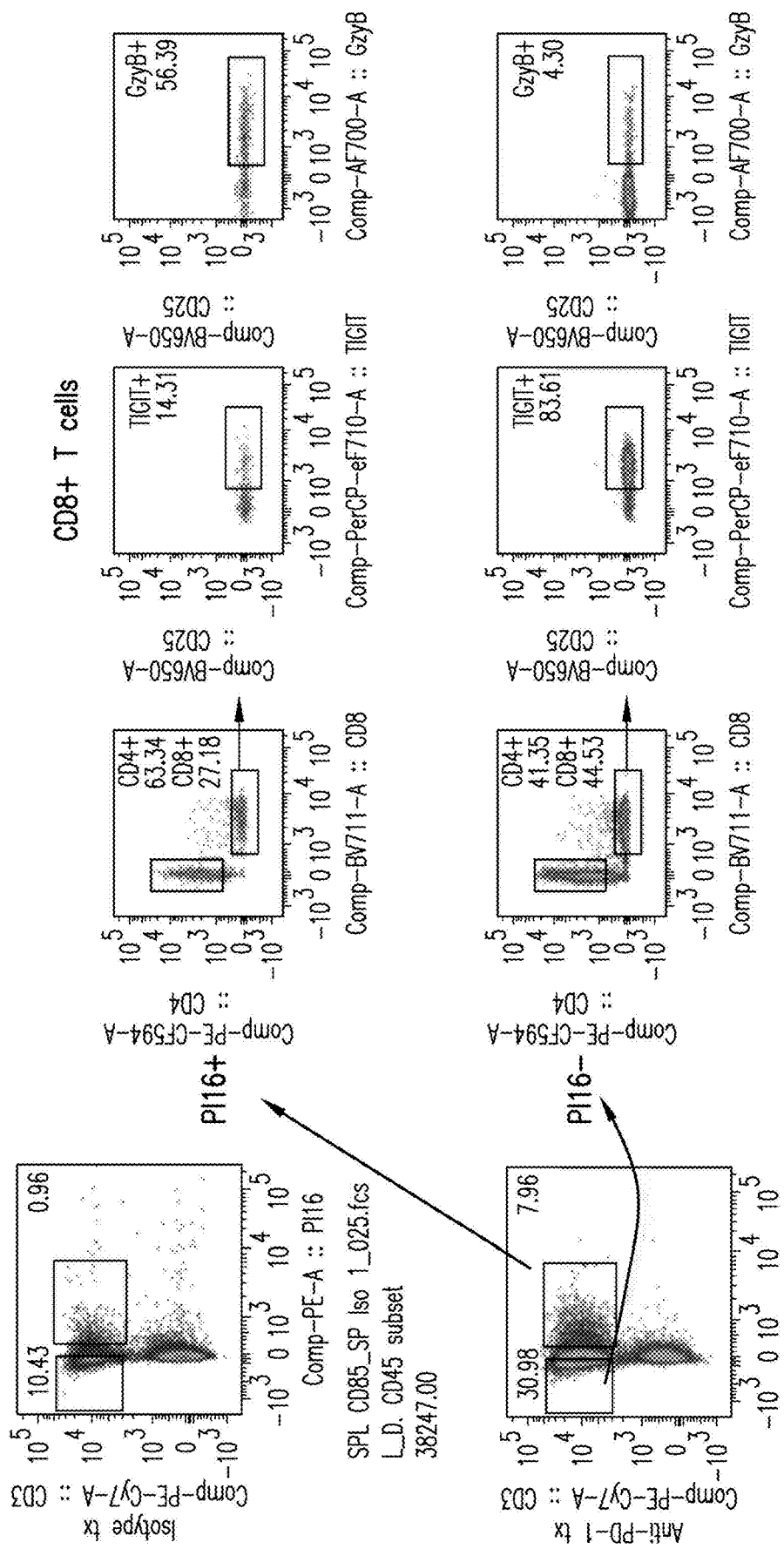
FIG. 11. Anti-PD1 activated T cells have enhanced PI16 expression. Humanized mice (CD34+ hematopoietic stem cells engrafted NSG mice) transplanted with PANC08 human pancreatic tumor cells were treated with isotype control antibody or anti-PD1 antibody, Pembrolizumab. Spleen cells were isolated, stained with CD3, CD4, CD8 and anti-PI16, and analyzed by flow cytometry. PI16+CD3+ CD8+ cells have lower level of TIGIT (a T cell exhaustion marker) and higher level of Granzyme B (cytotoxic T cell marker) compared to PI16 negative cells.

Humanized mice (CD34+ hematopoietic stem cells engrafted NSG mice) transplanted with PANC08 human pancreatic tumor cells were treated with isotype control antibody or anti-PD1 antibody, Pembrolizumab. Spleen cells were isolated, stained with CD3, CD4, CD8 and anti-PI16, and analyzed by flow cytometry. As shown in FIG. 11, PI16+CD3+CD8+ cells have lower level of TIGIT (T cell exhaustion marker) and higher level of Granzyme B (cytotoxic marker) compared to PI16 negative cells. This result indicates that PI16 is expressed on a population of activated T cells and that anti-PD1 treatment enhanced PI16 expression.

Example 6

Identification of Anti-PI16 Antibodies that Blocked ILT3Fc Binding

Figure 12:
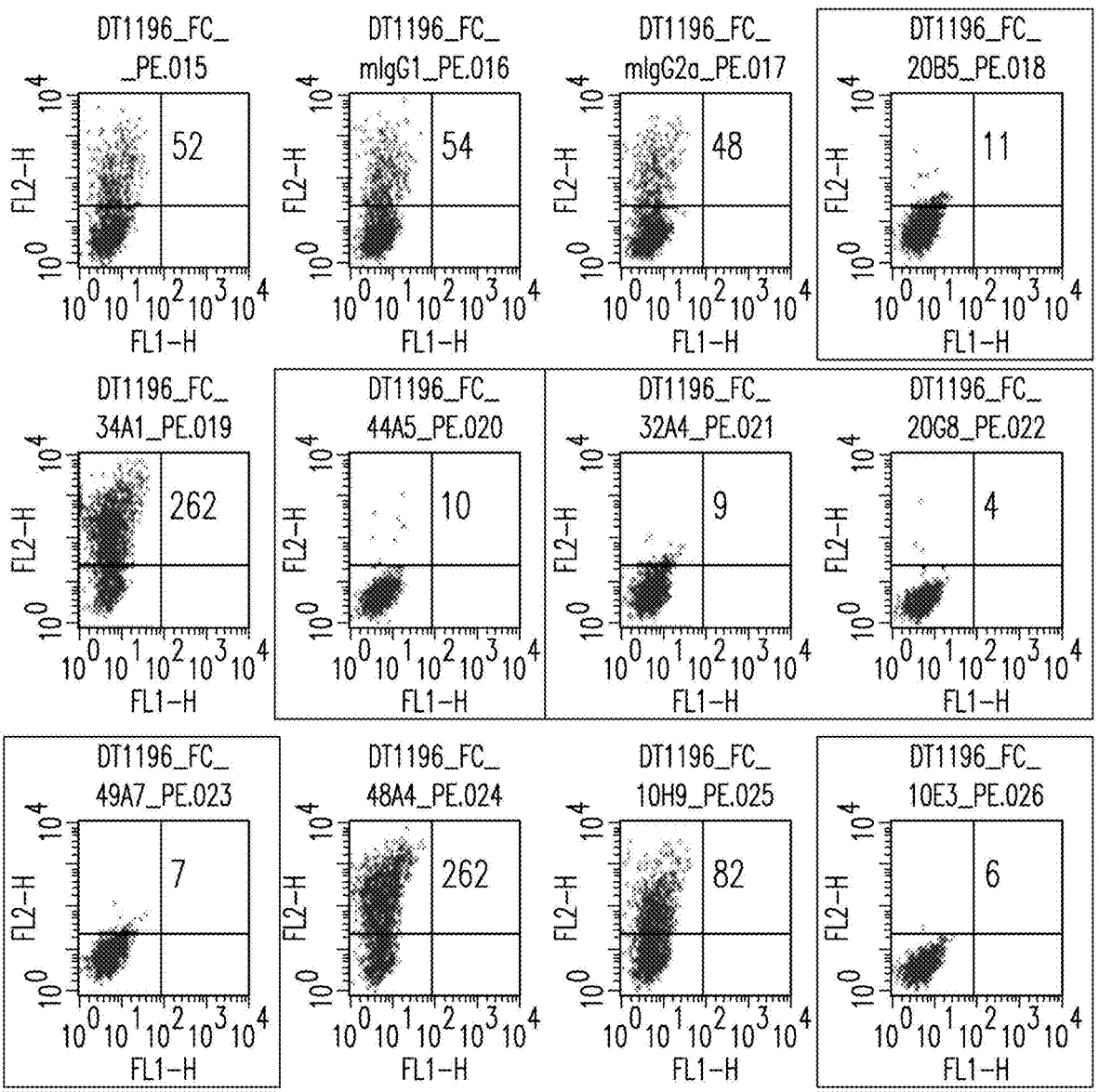
FIG. 12. Identification of anti-PI16 antibodies that blocked ILT3Fc binding to a PI16 transfected cell line: nine antibodies were shown to bind CHO cells expressing cell surface recombinant PI16 (top panel). To identify antibodies that can block ILT3Fc binding to PI16, 3A9 cells were transfected with PI16 cDNA vector and then subjected to staining with ILT3Fc to bind PI16 expressed on the cell surface. Goat anti-human Fc antibody was used as a secondary staining antibody. Five of the anti-PI16 antibodies including clone 20B5, 44A5, 10E3, 49A7, and 20G8 blocked PI16+ cell binding to ILT3Fc. These antibody clones engage critical contact residues between PI16 and ILT3. Clones 34A1, 10H9, and 48A4 did not block PI16+ cell binding to ILT3Fc, indicating that 34A1, 10H9, and 48A4 engage PI16 epitope(s) not relevant for binding to ILT3.

Nine antibodies were identified to bind CHO cells expressing cell surface recombinant PI16 (FIG. 12, top panel). The heavy chain and light chain variable domain of anti-PI16 antibodies 20B5, 49A7, 10E3, and 32A4 were sequenced.

| | SEQ ID NO: | |
|---|---|---|
| Antibody | Heavy chain variable domain | Light chain varaible domain |
| 20B5 | 48 | 49 |
| 49A7 | 50 | 51 |
| 10E3 | 52 | 53 |
| 32A4 | 54 | 55 |

Five of the anti-PI16 antibodies blocked ILT3Fc binding. 3A9 cells were transfected with a cDNA vector encoding human PI16 and were subjected to staining with ILT3Fc. Goat anti-human Fc was used as a secondary staining antibody. Anti-PI16 Clones 20B5, 44A5, 10E3, 49A7, and 20G8 blocked PI16+ cell binding to ILT3Fc. These antibody clones engage critical contact residues between PI16 and ILT3. As shown in FIG. 12, clones 34A1, 10H9, and 48A4 did not block PI16+ cell binding to ILT3Fc, indicating that 34A1, 10H9, and 48A4 engage PI16 epitope(s) not relevant for binding to ILT3.

Example 7

Plate Bound Recombinant PI16 Down-Regulates Dendritic Cell Activation which is Reversible by PI16 Antagonist Antibodies (49A7 and 10E3)

Healthy human donor CD14+ monocytes were differentiated in GMCSF and IL4 for 6 days and stimulated with IFNα and LPS 24 hours prior to the assay. PI16 bound to 96 well plate was incubated with control antibody or PI16 antibodies for 30 minutes, washed, and activated dendritic cells were added. Following 72 hours stimulation, cells were analyzed for CD86 expression and cytokine production.

Figure 13:
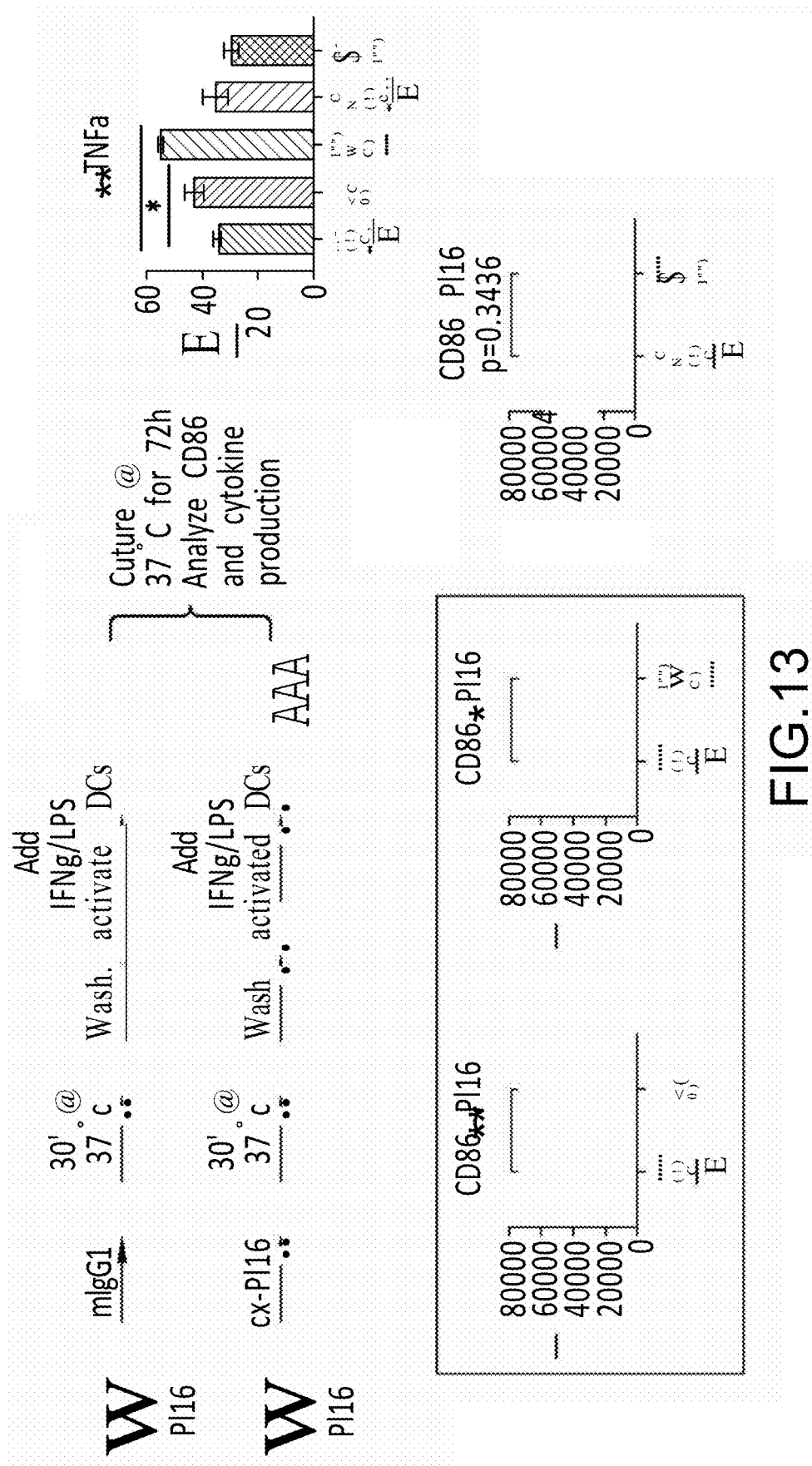
FIG. 13. PI16-mediated suppression of ILT3+ dendritic cells is reversed by PI16 antagonist antibodies. Healthy human donor CD14+ monocytes were differentiated into dendritic cells by culturing in GMCSF and IL4 for 6 days and stimulated with IFNγ and LPS 24 hours prior to the assay. Recombinant PI16 bound to wells of a 96 well plates was incubated with control antibody or anti-PI16 antibodies for 30 minutes, washed, and activated dendritic cells were added. Following 72 hour stimulation, cells were analyzed for CD86 expression and TNF production. Anti-PI16 clones 49A7 and 10E3 (ILT3 blockers) "de-repressed" PI16 suppression of human dendritic cells by enhancing TNF and CD86 expression. Clone 34A1, which is a non-ILT3-blocker (See FIG. 12) did not enhance dendritic cells activation.

As shown in FIG. 13, clones 49A7 and 10E3 blocked recombinant PI16 activation of human PBMC. Clone 34A1, which is a non-ILT3-blocker did not inhibit activation of human monocytes. This result is consistent with the concept that PI16 expressed by activated T cells serves as a feedback inhibitor to limit activation of ILT3+ myeloid cells. Therefore, by targeting this molecular pathway, the immune system can be turned-up to enhance reactivity for cancer immunotherapy.

Table of Antibody Sequences

| SEQ ID NO | DESCRIPTION | SEQUENCE |
|---|---|---|
| 1 | Human ILT3 precursor with 21 amino acid signal sequence; | MIPTFTALLCLGLSLGPRTHMQAGPLPKPTLWAE PGSVISWGNSVTIWCQGTLEAREYRLDKEESPA PWDRQNPLEPKNKARFSIPSMTEDYAGRYRCY |

Table of Antibody Sequences

| SEQ ID NO | DESCRIPTION | SEQUENCE |
|---|---|---|
| | Amino acids 22-259 extracellular domain | YRSPVGWSQPSDPLELVMTGAYSKPTLSALPSP LVTSGKSVTLLCQSRSPMDTFLLIKERAAHPLL HLRSEHGAQQHQAEFPMSPVTSVHGGTYRCFS SHGFSHYLLSHPSDPLELIVSGSLEDPRPSPTRS VSTAAGPEDQPLMPTGSVPHSGLRRHWEVLIG VLVVSILLLSLLLFLLLQHWRQGKHRTLAQRQAD FQRPPGAAEPEPKDGGLQRRSSPAADVQGENFCA AVKNTQPEDGVEMDTRQSPHDEDPQAVTYAKVK HSRPRREMASPPSPLSGEFLDTKDRQAEEDRQMD TEAAASEAPQDVTYAQLHSFTLRQKATEPPPSQE GASPAEPSVYATLAIH |
| 2 | Human PI16 long isoform precursor with 27 amino acid signal sequence | MHGSCSFLMLLLPLLLLLVATTGPVGALTDEEKR LMVELHNLYRAQVSPTASDMLHMRWDEELAAF AKAYARQCVWGHNKERGRRGENLFAITDEGMD VPLAMEEWHHEREHYNLSAATCSPGQMCGHYTQ VVWAKTERIGCGSHFCEKLQGVEETNIELLVCNY EPPGNVKGKRPYQEGTPCSQCPSGYHCKNSLCEPI GSPEDAQDLPYLVTEAPSFRATEASDSRKMGTPSS LATGIPAFLVTEVSGSLATKALPAVETQAPTSLAT KDPPSMATEAPPCVTTEVPSILAAHSLPSLDEEPVT FPKSTHVPIPKSADKVTDKTKVPSRSPENSLDPKM SLTGARELLPHAQEEAEAEAELPPSSEVLASVFPA QDKPGELQATLDHTGHTSSKSLPNFPNTSATANA TGGRALALQSSLPGAEGPDKPSVVSGLNSGPGHV WGPLLGLLLLPPLVLAGIF |
| 3 | Human PI16 short isoform precursor with 27 amino acid signal sequence (lacks | MHGSCSFLMLLLPLLLLLVATTGPVGALTDEEKR LMVELHNLYRAQVSPTASDMLHMRWDEELAAF AKAYARQCVWGHNKERGRRGENLFAITDEGMD VPLAMEEWHHEREHYNLSAATCSPGQMCGHYTQ VVWAKTERIGCGSHFCEKLQGVEETNIELLVCNY EPPGNVKGKRPYQEGTPCSQCPSGYHCKNSLCEPI GSPEDAQDLPYLVTEAPSFRATEASDSRKMGAEG PDKPSVVSGLNSGPGHVWGPLLGLLLLPPLVLAGI F |
| 4 | Human PI16 full-length secreted isoform precursor with 27 amino acid signal sequence (Retrogenix) | MHGSCSFLMLLLPLLLLLVATTGPVGALTDEEKR LMVELHNLYRAQVSPTASDMLHMRWDEELAAF AKAYARQCVWGHNKERGRRGENLFAITDEGMD VPLAMEEWHHEREHYNLSAATCSPGQMCGHYTQ VVWAKTERIGCGSHFCEKLQGVEETNIELLVCNY EPPGNVKGKRPYQEGTPCSQCPSGYHCKNSLCEPI GSPEDAQDLPYLVTEAPSFRATEASDSRKMGTPSS LATGIPAFLVTEVSGSLATKALPAVETQAPTSLAT KDPPSMATEAPPCVTTEVPSILAAHSLPSLDEEPVT FPKSTHVPIPKSADKVTDKTKVPSRSPENSLDPKM SLTGARELLPHAQEEAEAEAELPPSSEVLASVFPA QDKPGELQATLDHTGHTSSKSLPKFPQYLCHR |
| 5 | FLAG Tag | DYKDDDDK |
| 6 | Human ILT11 (also known as LILRA5) | MAPWSHPSAQLQPVGGDAVSPALMVLLCLGLSL GPRTHVQAGNLSKATLWAEPGSVISRGNSVTIRC QGTLEAQEYRLVKEGSPEPWDTQNPLEPKNKARF SIPSMTEHHAGRYRCYYYSPAGWSEPSDPLELVV TGFYNKPTLSALPSPVVTSGENVTLQCGSRLRFDR FILTEEGDHKLSWTLDSQLTPSGQFQALFPVGPVT PSHRWMLRCYGSRRHILQVWSEPSDLLEIPVSGA ADNLSPSQNKSDSGTASHLQDYAVENLIRMGMA GLILVVLGILIFQDWHSQRSPQAAAGR |
| 7 | Human ILT8 (also known as LILRA6) | MTPTLAALLCLGLSLGPRTHVQAGPFPKPTLWAE PGSVISWGSPVTIWCQGSLEAQEYRLDKEGSPEP WDRNNPLEPKNKARFSIPSITEHHAGRYRCHYSS AGWSEPSDPLELVMTGAYSKPTLSALPSPVVASG GNMTLQCGSQKGYHHFVLMKEGEHQLPRTLDSQ QLHSGGFQALFPVGPVNPSHRWRFTCYYYYMNT PRVWSHPSDPLEILPSGVSRKPSLLTLQGPVLAPG QSLTLQCGSDVGYDRFVLYKEGERDFLQRPGQQP QAGLSQANFTLGPVSPSHGGQYRCYGAHNLSSE WSAPSDPLNILMAGQIYDTVSLSAQPGPTVASGEN VTLLCQSWWQFDTFLLTKEGAAHPPLRLRSMYG |

| SEQ ID NO | DESCRIPTION | SEQUENCE |
|---|---|---|
| | | AHKYQAEFPMSPVTSAHAGTYRCYGSYSSNPHLL SFPSEPLELMVSGHSGGSSLPPTGPPSTPASHAKD YTVENLIRMGMAGLVLVFLGILLFEAQHSQRNPQ DAAGR |
| 8 | VH_DX446 | QIQLVQSGPELKKPGETVKISCKASGYTFTNYRMT WVKQAPGKGLKWMGWINTNTGDPTYAEELKGR FAFSSETSASTAYLQINNLKNEDTATYFCAREGFF NYAMDYWGQGTSVTVSS |
| 9 | VL_DX446 | DILLTQSPAILSVSPGKRVSFSCRASQSIGTSIHWY QQRTNGSPRLLIKYASESISGIPSRFSGSGSGTDFTL SINSVESEDIADYYCQQSNSWPPTFGAGTKLELK |
| 10 | VH_DX446 CDR1 | NYRMT |
| 11 | VH_DX446 CDR2 | WINTNTGDPTYAEELKG |
| 12 | VH_DX446 CDR3 | EGFFNYAMDY |
| 13 | VL_DX446 CDR1 | RASQSIGTSIH |
| 14 | VL_DX446 CDR2 | YASESIS |
| 15 | VL_DX446 CDR3 | QQSNSWPPT |
| 16 | VH_DX435 | EVQLQQSGPEMVKPGASVKISCKASGYAFTDYNI HWVKKSHGKSPEWIGHIYPYNKDTVFNQNKTKA TLTVDKSTTTAYMDLRSLTSEDSAVYYCARGAV GYFDYWGQGTTLTVSS |
| 17 | VL_DX435 | DIQMTQSPASLSASVGETVTITCRASGNIHNFLAW YQQKQGKSPQLLVYNAKTLADGVPSRFSGSGSGT QYSLKINSLQPEDFGSYYCQHFWSYPFTFGAGTK LELK |
| 18 | VH_DX435 CDR1 | DYNIH |
| 19 | VH_DX435 CDR2 | HIYPYNKDTVFNQNKT |
| 20 | VH_DX435 CDR3 | GAVGYFDY |
| 21 | VL_DX435 CDR1 | RASGNIHNFLA |
| 22 | VL_DX435 CDR2 | NAKTLAD |
| 23 | VL_DX435 CDR3 | QHFWSYPFT |
| 24 | VH_DX439 | EVQLQQPGPELVKPGASVKISCKASGYTFTDYNM HWVRQRHGKSLEWIGHIYPYNGNTVYNQRFKNK ATLNVDNFSSTAYMELRSLTSEDSAVYYCARGAV GYFDHWGQGTTLTVSS |
| 25 | VL_DX439 | DIQMTQSPASLSASVGETVTITCRASGNIHNFLAW YQQKQGRSPQLLVYNAKTLADGVPSRFSGSGSGT QYSLKINSLQPEDFGNYYCQHFWSYPFTFGAGTN LELK |
| 26 | VH_DX439 CDR1 | DYNMH |
| 27 | VH_DX439 CDR2 | HIYPYNGNTVYNQRFKN |
| 28 | VH_DX439 CDR3 | GAVGYFDH |
| 29 | VL_DX439 CDR1 | RASGNIHNFLA |
| 30 | VL_DX439 CDR2 | NAKTLAD |
| 31 | VL_DX439 CDR3 | QHFWSYPFT |

Table of Antibody Sequences

| SEQ ID NO | DESCRIPTION | SEQUENCE |
|---|---|---|
| 32 | VH_DX440 | EVQLQQSGPELVKPGASVKISCKASGYTFSDYNM HWVKQSHGKSLKWIGHIFPYIGDTVYNQKFTSKA TLTVDNSSTGYMEIRSLTSEDSAVYYCARGAVG YFDYWGQGTTLTVSS |
| 33 | VL_DX440 | DIQMTQSPASLSASVGETVTITCRASGNIHNYLAW YQQKQGKSPQFLVYNAKTLADGVPSRFSGSGSGT QYSLKINSLQPEDFGTYYCQHFWSFPFTFGAGTKL ELK |
| 34 | VH_DX440 CDR1 | DYNMH |
| 35 | VH_DX440 CDR2 | HIFPYIGDTVYNQKFTS |
| 36 | VH_DX440 CDR3 | GAVGYFDY |
| 37 | VL_DX440 CDR1 | RASGNIHNYLA |
| 38 | VL_DX440 CDR2 | NAKTLAD |
| 39 | VL_DX440 CDR3 | QHFWSFPFT |
| 41 | Human ILT3 mature protein Extracellular domain amino acids 1-238 | QAGPLPKPTLWAEPGSVISWGNSVTIWCQGTL EAREYRLDKEESPAPWDRQNPLEPKNKARFSIP SMTEDYAGRYRCYYRSPVGWSQPSDPLELVMT GAYSKPTLSALPSPLVTSGKSVTLLCQSRSPMD TFLLIKERAAHPLLHLRSEHGAQQHQAEFPMS PVTSVHGGTYRCFSSHGFSHYLLSHPSDPLELIV SGSLEDPRPSPTRSVSTAAGPEDQPLMPTGSVP HSGLRRHWEVLIGVLVVSILLLSLLLFLLLQHWR QGKHRTLAQRQADFQRPPGAAEPEPKDGGLQRR SSPAADVQGENFCAAVKNTQPEDGVEMDTRQSP HDEDPQAVTYAKVKHSRPRREMASPPSPLSGEFL DTKDRQAEEDRQMDTEAAASEAPQDVTYAQLHS FTLRQKATEPPPSQEGASPAEPSVYATLAIH |
| 42 | Human PI6 long isoform mature protein | LTDEEKRLMVELHNLYRAQVSPTASDMLHMRW DEELAAFAKAYARQCVWGHNKERGRRGENLFAI TDEGMDVPLAMEEWHHEREHYNLSAATCSPGQ MCGHYTQVVWAKTERIGCGSHFCEKLQGVEETNI ELLVCNYEPPGNVKGKRPYQEGTPCSQCPSGYHC KNSLCEPIGSPEDAQDLPYLVTEAPSFRATEASDS RKMGTPSSLATGIPAFLVTEVSGSLATKALPAVET QAPTSLATKDPPSMATEAPPCVTTEVPSILAAHSL PSLDEEPVTFPKSTHVPIPKSADKVTDKTKVPSRSP ENSLDPKMSLTGARELLPHAQEEAEAEAELPPSSE VLASVFPAQDKPGELQATLDHTGHTSSKSLPNFP NTSATANATGGRALALQSSLPGAEGPDKPSVVSG LNSGPGHVWGPLLGLLLLPPLVLAGIF |
| 43 | Human PI16 short isoform mature protein | LTDEEKRLMVELHNLYRAQVSPTASDMLHMRW DEELAAFAKAYARQCVWGHNKERGRRGENLFAI TDEGMDVPLAMEEWHHEREHYNLSAATCSPGQ MCGHYTQVVWAKTERIGCGSHFCEKLQGVEETNI ELLVCNYEPPGNVKGKRPYQEGTPCSQCPSGYHC KNSLCEPIGSPEDAQDLPYLVTEAPSFRATEASDS RKMGAEGPDKPSVVSGLNSGPGHVWGPLLGLLL LPPLVLAGIF |
| 44 | Human PI16 full-length secreted isoform protein (Retrogenix) | LTDEEKRLMVELHNLYRAQVSPTASDMLHMRW DEELAAFAKAYARQCVWGHNKERGRRGENLFAI TDEGMDVPLAMEEWHHEREHYNLSAATCSPGQ MCGHYTQVVWAKTERIGCGSHFCEKLQGVEETNI ELLVCNYEPPGNVKGKRPYQEGTPCSQCPSGYHC KNSLCEPIGSPEDAQDLPYLVTEAPSFRATEASDS RKMGTPSSLATGIPAFLVTEVSGSLATKALPAVET QAPTSLATKDPPSMATEAPPCVTTEVPSILAAHSL PSLDEEPVTFPKSTHVPIPKSADKVTDKTKVPSRSP ENSLDPKMSLTGARELLPHAQEEAEAEAELPPSSE VLASVFPAQDKPGELQATLDHTGHTSSKSLPKFP QYLCHR |

-continued

Table of Antibody Sequences

| SEQ ID NO | DESCRIPTION | SEQUENCE |
|---|---|---|
| 45 | Human ILT11 mature protein | GNLSKATLWAEPGSVISRGNSVTIRCQGTLEAQEY RLVKEGSPEPWDTQNPLEPKNKARFSIPSMTEHH AGRYRCYYYSPAGWSEPSDPLELVVTGFYNKPTL SALPSPVVTSGENVTLQCGSRLRFDRFILTEEGDH KLSWTLDSQLTPSGQFQALFPVGPVTPSHRWMLR CYGSRRHILQVWSEPSDLLEIPVSGAADNLSPSQN KSDSGTASHLQDYAVENLIRMGMAGLILVVLGILI FQDWHSQRSPQAAAGR |
| 46 | Human ILT8 mature protein | QAGPFPKPTLWAEPGSVISWGSPVTIWCQGSLEA QEYRLDKEGSPEPWDRNNPLEPKNKARFSIPSITE HHAGRYRCHYYSSAGWSEPSDPLELVMTGAYSK PTLSALPSPVVASGGNMTLQCGSQKGYHHFVLM KEGEHQLPRTLDSQQLHSGGFQALFPVGPVNPSH RWRFTCYYYYMNTPRVWSHPSDPLEILPSGVSRK PSLLTLQGPVLAPGQSLTLQCGSDVGYDRFVLYK EGERDFLQRPGQQPQAGLSQANFTLGPVSPSHGG QYRCYGAHNLSSEWSAPSDPLNILMAGQIYDTVS LSAQPGPTVASGENVTLLCQSWWQFDTFLLTKEG AAHPPLRLRSMYGAHKYQAEFPMSPVTSAHAGT YRCYGSYSSNPHLLSFPSEPLELMVSGHSGGSSLP PTGPPSTPASHAKDYTVENLIRMGMAGLVLVFLGI LLFEAQHSQRNPQDAAGR |
| 47 | ITL3Fc (extracellular domain amino acids 1-238)(Fc amino acids 239-463) | QAGPLPKPTLWAEPGSVISWGNSVTIWCQGTLEA REYRLDKEESPAPWDRQNPLEPKNKARFSIPSMTE DYAGRYRCYYRSPVGWSQPSDPLELVMTGAYSK PTLSALPSPLVTSGKSVTLLCQSRSPMDTFLLIKER AAHPLLHLRSEHGAQQHQAEFPMSPVTSVHGGTY RCFSSHGFSHYLLSHPSDPLELIVSGSLEGPRPSPT RSVSTAAGPEDQPLMPTGSVPHSGLRRHWE*THTC PPCPAPELLGGPSVFLFPPKPKDTLMISRTPEVTCVV VDVSHEDPEVKFNWYVDGVEVHNAKTKPREEQYNS TYRWSVLTVLHQDWLNGKEYKCKVSNKALPAPIEK TISKAKGQPREPQVYTLPPSRDELTKNQVSLTCLVKG FYPSDIAVEWESNGQPENNYKTTPPVLDSDGSFFLYS KLTVDKSRWQQGNVFSCSVMHEALHNHYTQKSLSLS PGK* |
| 48 | Anti-PI16 clone 20B5 heavy chain variable domain | EVQLLESGGGLVQPGGSLRVSCAASGFTFSSYAM SWVRQAPGKGLEWVSTISGSGGTTHYADSVKGR FTISRDNSKNTVYMQMSSLRAEDTAAYYCAKDL GLRAQGWFDPWGQGTLVTVSS |
| 49 | Anti-PI16 clone 20B5 light chain variable domain | QLVLTQSPSASASLGASVKLTCTLSSGHSSYAIAW HQQQPEKGPRYLMKLNSDGSHSKGDGIPDRFSGS SSGAERYLTISSLQSEDEADYYCQTWGTGIAVFGG GTQLTPL |
| 50 | Anti-PI16 clone 49A7 heavy chain variable domain | EVQLLESGGGLVQPGGSLRLSCIASGFTFSSYAMT WVRQVPGRGLEWVSAISGSGFNTYYADSVKGRF TISRDNSKNTLYLQMNSLRVEETALYFCAKDLGM RAQGWFDPWGQGTLVTVSS |
| 51 | Anti-PI16 clone 49A7 light chain variable domain | QLVLTQSPSASASLGASVKLTRTLSSGLSSYAIAR QQQQPEKGPRYLMKFNSDGSHSKGDGIPDRFSGS RSGTERYVTISSLQSEDEADYYCQTWGTGTAVFG GGTQLTAL |
| 52 | Anti-PI16 clone 10E3 heavy chain variable domain | EVLLLESGGGLVHPGGSLKLSCAASGFTFSSYAM SWVRQVPGKGLEWVSTISGGGGYTYFADSVKGR FTISRDNSKDTLYLQMNSLRAEDTAVYFCAKDLG SRAQGWFDPWGQGTLVTVSS |
| 53 | Anti-PI16 clone 10E3 light chain variable domain | QPVLTQPSSHSASSGASVRLTCMLSSGFSVGDFWI RWYQQKPGNPPRYLLYYHSDSNKGQGSGVPSRF SGSNDASANAGILRISGLQPEDEADYYCGTWHSN SKTFIFGSGTKVTVL |
| 54 | Anti-PI16 clone 32A4 heavy chain variable domain | QVKLVESGGGVVQPGRSLRLSCAASGFTFSSYGM HWVRQAPGKGLEWVAVIWYDGSNKYYIDSVKG RFTISRDNSKNTLYLQMNSLRAEDTAVYNCARDR RITMVRGVMRGMDVWGQGTTVTVSS |

Table of Antibody Sequences

| SEQ ID NO | DESCRIPTION | SEQUENCE |
|---|---|---|
| 55 | Anti-PI16 clone 32A4 light chain variable domain | EIVMTQSPATLSLSPGERATLSCRASQSVSSRYLS WYQQKPGQAPRLLIYGASTRATGIPARFSGSGSGT DFTLTISSLQPEDFAVYYCQQDYNLPWTFGQGTK VEIK |
| 56 | Human IgG4 HC Constant domain (S228P) | ASTKGPSVFPLAPCSRSTSESTAALGCLVKDYFPEPVT VSWNSGALTSGVHTFPAVLQSSGLYSLSSWTVPSSSL GTKTYTCNVDHKPSNTKVDKRVESKYGPPCPCPAP EFLGGPSVFLFPPKPKDTLMISRTPEVTCVVVDVSQE DPEVQFNWYVDGVEVHNAKTKPREEQFNSTYRWSV LTVLHQDWLNGKEYKCKVSNKGLPSSIEKTISKAKG QPREPQVYTLPPSQEEMTKNQVSLTCLVKGFYPSDIA VEWESNGQPENNYKTTPPVLDSDGSFFLYSRLTVDK SRWQEGNVFSCSVMHEALHNHYTQKSLSLSLGK |
| 57 | Human IgG1 HC Constant domain (L234A L235A D265S) | ASTKGPSVFPLAPSSKSTSGGTAALGCLVKDYFPEPV TVSWNSGALTSGVHTFPAVLQSSGLYSLSSWTVPSSS LGTQTYICNVNHKPSNTKVDKKVEPKSCDKTHTCPP CPAPEAAGGPSVFLFPPKPKDTLMISRTPEVTCVVVS VSHEDPEVKFNWYVDGVEVHNAKTKPREEQYNSTYR VVSVLTVLHQDWLNGKEYKCKVSNKALPAPIEKTISK AKGQPREPQVYTLPPSRDELTKNQVSLTCLVKGFYP SDIAVEWESNGQPENNYKTTPPVLDSDGSFFLYSKLT VDKSRWQQGNVFSCSVMHEALHNHYTQKSLSLSPG K |

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. An antibody or antigen-binding fragment thereof that binds PI16 comprising:
   (i) a heavy chain variable region comprising the amino acid sequence set forth in SEQ ID NO: 48 and a light chain variable region comprising the amino acid sequence set forth in SEQ ID NO: 49; or
   (ii) a heavy chain variable region comprising the amino acid sequence set forth in SEQ ID NO: 50 and a light chain variable region comprising the amino acid sequence set forth in SEQ ID NO: 51; or
   (iii) a heavy chain variable region comprising the amino acid sequence set forth in SEQ ID NO: 52 and a light chain variable region comprising the amino acid sequence set forth in SEQ ID NO: 53; or
   (iv) a heavy chain variable region comprising the amino acid sequence set forth in SEQ ID NO: 54 and a light chain variable region comprising the amino acid sequence set forth in SEQ ID NO: 55.

2. The antibody or antigen-binding fragment thereof of claim 1, wherein the antibody blocks binding of ILT3 to PI16.

3. The antibody or antigen-binding fragment thereof of claim 1, comprising a human IgG1, IgG2, IgG3, or IgG4 heavy chain (HC) constant domain or variant thereof comprising 1, 2, 3, 4, 5, 6, 7, 8, 9, or 10 amino acid substitutions, additions, deletions, or combinations thereof compared to the amino acid sequence of the native IgG1, IgG2, IgG3, or IgG4 isotype.

4. The antibody or antigen-binding fragment thereof of claim 3, comprising a IgG4 constant domain with a Ser228Pro mutation.

5. The antibody or antigen-binding fragment thereof of claim 3, comprising a human IgG1 constant domain modified to include one or more amino acid substitutions selected from E233P, L234A, L235A, L235E, N297A, N297D, D265S, and P331S, wherein the residues are numbered according to the EU index of Kabat, and wherein said polypeptide exhibits a reduced affinity to the human FcγRIIIA and/or FcγRIIA and/or FcγRI compared to a polypeptide comprising the wildtype IgG1 constant domain.

6. The antibody or antigen-binding fragment thereof of claim 5, wherein the one or more amino acid substitutions in the human IgG1 constant domain consist of an L234A, an L235A, and a D265S mutation.

7. The antibody or antigen-binding fragment thereof of claim 1, comprising a lambda light chain constant domain.

8. The antibody or antigen-binding fragment thereof of claim 1, comprising a kappa light chain constant domain.

9. The antibody or antigen-binding fragment thereof of claim 1, wherein the antibody or antigen-binding fragment thereof is a Fab fragment.

10. The antibody or antigen-binding fragment thereof of claim 1, wherein the antibody or antigen-binding fragment thereof is a Fab' fragment.

11. The antibody or antigen-binding fragment thereof of claim 1, wherein the antibody or antigen-binding fragment thereof is a F(ab')$_2$ fragment.

12. The antibody or antigen-binding fragment thereof of claim 1, comprising the Fv region from both the heavy and light chains but lacks the constant domain.

13. The antibody or antigen-binding fragment thereof of claim 1, wherein antibody or antigen-binding fragment thereof is a single-chain Fv.

* * * * *

SEQUENCE LISTING

```
<160> NUMBER OF SEQ ID NOS: 57

<210> SEQ ID NO 1
<211> LENGTH: 448
<212> TYPE: PRT
<213> ORGANISM: Homo sapiens

<400> SEQUENCE: 1

Met Ile Pro Thr Phe Thr Ala Leu Leu Cys Leu Gly Leu Ser Leu Gly
1               5                   10                  15

Pro Arg Thr His Met Gln Ala Gly Pro Leu Pro Lys Pro Thr Leu Trp
            20                  25                  30

Ala Glu Pro Gly Ser Val Ile Ser Trp Gly Asn Ser Val Thr Ile Trp
        35                  40                  45

Cys Gln Gly Thr Leu Glu Ala Arg Glu Tyr Arg Leu Asp Lys Glu Glu
    50                  55                  60

Ser Pro Ala Pro Trp Asp Arg Gln Asn Pro Leu Glu Pro Lys Asn Lys
65                  70                  75                  80

Ala Arg Phe Ser Ile Pro Ser Met Thr Glu Asp Tyr Ala Gly Arg Tyr
                85                  90                  95

Arg Cys Tyr Tyr Arg Ser Pro Val Gly Trp Ser Gln Pro Ser Asp Pro
            100                 105                 110
```

Leu Glu Leu Val Met Thr Gly Ala Tyr Ser Lys Pro Thr Leu Ser Ala
            115                 120                 125

Leu Pro Ser Pro Leu Val Thr Ser Gly Lys Ser Val Thr Leu Leu Cys
130                 135                 140

Gln Ser Arg Ser Pro Met Asp Thr Phe Leu Leu Ile Lys Glu Arg Ala
145                 150                 155                 160

Ala His Pro Leu Leu His Leu Arg Ser Glu His Gly Ala Gln Gln His
            165                 170                 175

Gln Ala Glu Phe Pro Met Ser Pro Val Thr Ser Val His Gly Gly Thr
            180                 185                 190

Tyr Arg Cys Phe Ser Ser His Gly Phe Ser His Tyr Leu Leu Ser His
            195                 200                 205

Pro Ser Asp Pro Leu Glu Leu Ile Val Ser Gly Ser Leu Glu Asp Pro
            210                 215                 220

Arg Pro Ser Pro Thr Arg Ser Val Ser Thr Ala Ala Gly Pro Glu Asp
225                 230                 235                 240

Gln Pro Leu Met Pro Thr Gly Ser Val Pro His Ser Gly Leu Arg Arg
            245                 250                 255

His Trp Glu Val Leu Ile Gly Val Leu Val Ser Ile Leu Leu Leu
            260                 265                 270

Ser Leu Leu Leu Phe Leu Leu Leu Gln His Trp Arg Gln Gly Lys His
            275                 280                 285

Arg Thr Leu Ala Gln Arg Gln Ala Asp Phe Gln Arg Pro Pro Gly Ala
            290                 295                 300

Ala Glu Pro Glu Pro Lys Asp Gly Gly Leu Gln Arg Arg Ser Ser Pro
305                 310                 315                 320

Ala Ala Asp Val Gln Gly Glu Asn Phe Cys Ala Ala Val Lys Asn Thr
            325                 330                 335

Gln Pro Glu Asp Gly Val Glu Met Asp Thr Arg Gln Ser Pro His Asp
            340                 345                 350

Glu Asp Pro Gln Ala Val Thr Tyr Ala Lys Val Lys His Ser Arg Pro
            355                 360                 365

Arg Arg Glu Met Ala Ser Pro Pro Ser Pro Leu Ser Gly Glu Phe Leu
            370                 375                 380

Asp Thr Lys Asp Arg Gln Ala Glu Glu Asp Arg Gln Met Asp Thr Glu
385                 390                 395                 400

Ala Ala Ala Ser Glu Ala Pro Gln Asp Val Thr Tyr Ala Gln Leu His
            405                 410                 415

Ser Phe Thr Leu Arg Gln Lys Ala Thr Glu Pro Pro Pro Ser Gln Glu
            420                 425                 430

Gly Ala Ser Pro Ala Glu Pro Ser Val Tyr Ala Thr Leu Ala Ile His
            435                 440                 445

<210> SEQ ID NO 2
<211> LENGTH: 463
<212> TYPE: PRT
<213> ORGANISM: Homo sapiens

<400> SEQUENCE: 2

Met His Gly Ser Cys Ser Phe Leu Met Leu Leu Leu Pro Leu Leu Leu
1               5                   10                  15

Leu Leu Val Ala Thr Thr Gly Pro Val Gly Ala Leu Thr Asp Glu Glu
            20                  25                  30

```
Lys Arg Leu Met Val Glu Leu His Asn Leu Tyr Arg Ala Gln Val Ser
            35                  40                  45

Pro Thr Ala Ser Asp Met Leu His Met Arg Trp Asp Glu Glu Leu Ala
        50                  55                  60

Ala Phe Ala Lys Ala Tyr Ala Arg Gln Cys Val Trp Gly His Asn Lys
65                  70                  75                  80

Glu Arg Gly Arg Gly Glu Asn Leu Phe Ala Ile Thr Asp Glu Gly
                85                  90                  95

Met Asp Val Pro Leu Ala Met Glu Glu Trp His His Glu Arg Glu His
            100                 105                 110

Tyr Asn Leu Ser Ala Ala Thr Cys Ser Pro Gly Gln Met Cys Gly His
            115                 120                 125

Tyr Thr Gln Val Val Trp Ala Lys Thr Glu Arg Ile Gly Cys Gly Ser
            130                 135                 140

His Phe Cys Glu Lys Leu Gln Gly Val Glu Glu Thr Asn Ile Glu Leu
145                 150                 155                 160

Leu Val Cys Asn Tyr Glu Pro Pro Gly Asn Val Lys Gly Lys Arg Pro
                165                 170                 175

Tyr Gln Glu Gly Thr Pro Cys Ser Gln Cys Pro Ser Tyr His Cys
            180                 185                 190

Lys Asn Ser Leu Cys Glu Pro Ile Gly Ser Pro Glu Asp Ala Gln Asp
            195                 200                 205

Leu Pro Tyr Leu Val Thr Glu Ala Pro Ser Phe Arg Ala Thr Glu Ala
            210                 215                 220

Ser Asp Ser Arg Lys Met Gly Thr Pro Ser Ser Leu Ala Thr Gly Ile
225                 230                 235                 240

Pro Ala Phe Leu Val Thr Glu Val Ser Gly Ser Leu Ala Thr Lys Ala
                245                 250                 255

Leu Pro Ala Val Glu Thr Gln Ala Pro Thr Ser Leu Ala Thr Lys Asp
            260                 265                 270

Pro Pro Ser Met Ala Thr Glu Ala Pro Pro Cys Val Thr Thr Glu Val
            275                 280                 285

Pro Ser Ile Leu Ala Ala His Ser Leu Pro Ser Leu Asp Glu Glu Pro
            290                 295                 300

Val Thr Phe Pro Lys Ser Thr His Val Pro Ile Pro Lys Ser Ala Asp
305                 310                 315                 320

Lys Val Thr Asp Lys Thr Lys Val Pro Ser Arg Ser Pro Glu Asn Ser
                325                 330                 335

Leu Asp Pro Lys Met Ser Leu Thr Gly Ala Arg Glu Leu Leu Pro His
            340                 345                 350

Ala Gln Glu Glu Ala Glu Ala Glu Ala Glu Leu Pro Pro Ser Ser Glu
            355                 360                 365

Val Leu Ala Ser Val Phe Pro Ala Gln Asp Lys Pro Gly Glu Leu Gln
            370                 375                 380

Ala Thr Leu Asp His Thr Gly His Thr Ser Ser Lys Ser Leu Pro Asn
385                 390                 395                 400

Phe Pro Asn Thr Ser Ala Thr Ala Asn Ala Thr Gly Gly Arg Ala Leu
                405                 410                 415

Ala Leu Gln Ser Ser Leu Pro Gly Ala Glu Gly Pro Asp Lys Pro Ser
            420                 425                 430

Val Val Ser Gly Leu Asn Ser Gly Pro Gly His Val Trp Gly Pro Leu
            435                 440                 445
```

Leu Gly Leu Leu Leu Leu Pro Pro Leu Val Leu Ala Gly Ile Phe
    450                 455                 460

<210> SEQ ID NO 3
<211> LENGTH: 270
<212> TYPE: PRT
<213> ORGANISM: Homo sapiens

<400> SEQUENCE: 3

Met His Gly Ser Cys Ser Phe Leu Met Leu Leu Pro Leu Leu Leu
1               5                   10                  15

Leu Leu Val Ala Thr Thr Gly Pro Val Gly Ala Leu Thr Asp Glu Glu
            20                  25                  30

Lys Arg Leu Met Val Glu Leu His Asn Leu Tyr Arg Ala Gln Val Ser
        35                  40                  45

Pro Thr Ala Ser Asp Met Leu His Met Arg Trp Asp Glu Glu Leu Ala
    50                  55                  60

Ala Phe Ala Lys Ala Tyr Ala Arg Gln Cys Val Trp Gly His Asn Lys
65                  70                  75                  80

Glu Arg Gly Arg Arg Gly Glu Asn Leu Phe Ala Ile Thr Asp Glu Gly
                85                  90                  95

Met Asp Val Pro Leu Ala Met Glu Glu Trp His His Glu Arg His
                100                 105                 110

Tyr Asn Leu Ser Ala Ala Thr Cys Ser Pro Gly Gln Met Cys Gly His
            115                 120                 125

Tyr Thr Gln Val Val Trp Ala Lys Thr Glu Arg Ile Gly Cys Gly Ser
        130                 135                 140

His Phe Cys Glu Lys Leu Gln Gly Val Glu Glu Thr Asn Ile Glu Leu
145                 150                 155                 160

Leu Val Cys Asn Tyr Glu Pro Pro Gly Asn Val Lys Gly Lys Arg Pro
                165                 170                 175

Tyr Gln Glu Gly Thr Pro Cys Ser Gln Cys Pro Ser Gly Tyr His Cys
            180                 185                 190

Lys Asn Ser Leu Cys Glu Pro Ile Gly Ser Pro Glu Asp Ala Gln Asp
        195                 200                 205

Leu Pro Tyr Leu Val Thr Glu Ala Pro Ser Phe Arg Ala Thr Glu Ala
    210                 215                 220

Ser Asp Ser Arg Lys Met Gly Ala Glu Gly Pro Asp Lys Pro Ser Val
225                 230                 235                 240

Val Ser Gly Leu Asn Ser Gly Pro Gly His Val Trp Gly Pro Leu Leu
                245                 250                 255

Gly Leu Leu Leu Leu Pro Pro Leu Val Leu Ala Gly Ile Phe
            260                 265                 270

<210> SEQ ID NO 4
<211> LENGTH: 408
<212> TYPE: PRT
<213> ORGANISM: Homo sapiens

<400> SEQUENCE: 4

Met His Gly Ser Cys Ser Phe Leu Met Leu Leu Pro Leu Leu Leu
1               5                   10                  15

Leu Leu Val Ala Thr Thr Gly Pro Val Gly Ala Leu Thr Asp Glu Glu
            20                  25                  30

Lys Arg Leu Met Val Glu Leu His Asn Leu Tyr Arg Ala Gln Val Ser
        35                  40                  45

Pro Thr Ala Ser Asp Met Leu His Met Arg Trp Asp Glu Glu Leu Ala
    50                  55                  60

Ala Phe Ala Lys Ala Tyr Ala Arg Gln Cys Val Trp Gly His Asn Lys
 65                  70                  75                  80

Glu Arg Gly Arg Arg Gly Glu Asn Leu Phe Ala Ile Thr Asp Glu Gly
                 85                  90                  95

Met Asp Val Pro Leu Ala Met Glu Glu Trp His His Glu Arg Glu His
            100                 105                 110

Tyr Asn Leu Ser Ala Ala Thr Cys Ser Pro Gly Gln Met Cys Gly His
            115                 120                 125

Tyr Thr Gln Val Val Trp Ala Lys Thr Glu Arg Ile Gly Cys Gly Ser
130                 135                 140

His Phe Cys Glu Lys Leu Gln Gly Val Glu Glu Thr Asn Ile Glu Leu
145                 150                 155                 160

Leu Val Cys Asn Tyr Glu Pro Pro Gly Asn Val Lys Gly Lys Arg Pro
                165                 170                 175

Tyr Gln Glu Gly Thr Pro Cys Ser Gln Cys Pro Ser Gly Tyr His Cys
            180                 185                 190

Lys Asn Ser Leu Cys Glu Pro Ile Gly Ser Pro Glu Asp Ala Gln Asp
            195                 200                 205

Leu Pro Tyr Leu Val Thr Glu Ala Pro Ser Phe Arg Ala Thr Glu Ala
210                 215                 220

Ser Asp Ser Arg Lys Met Gly Thr Pro Ser Ser Leu Ala Thr Gly Ile
225                 230                 235                 240

Pro Ala Phe Leu Val Thr Glu Val Ser Gly Ser Leu Ala Thr Lys Ala
                245                 250                 255

Leu Pro Ala Val Glu Thr Gln Ala Pro Thr Ser Leu Ala Thr Lys Asp
            260                 265                 270

Pro Pro Ser Met Ala Thr Glu Ala Pro Cys Val Thr Thr Glu Val
            275                 280                 285

Pro Ser Ile Leu Ala Ala His Ser Leu Pro Ser Leu Asp Glu Glu Pro
290                 295                 300

Val Thr Phe Pro Lys Ser Thr His Val Pro Ile Pro Lys Ser Ala Asp
305                 310                 315                 320

Lys Val Thr Asp Lys Thr Lys Val Pro Ser Arg Ser Pro Glu Asn Ser
                325                 330                 335

Leu Asp Pro Lys Met Ser Leu Thr Gly Ala Arg Glu Leu Leu Pro His
            340                 345                 350

Ala Gln Glu Glu Ala Glu Ala Glu Ala Glu Leu Pro Pro Ser Ser Glu
            355                 360                 365

Val Leu Ala Ser Val Phe Pro Ala Gln Asp Lys Pro Gly Glu Leu Gln
370                 375                 380

Ala Thr Leu Asp His Thr Gly His Thr Ser Ser Lys Ser Leu Pro Lys
385                 390                 395                 400

Phe Pro Gln Tyr Leu Cys His Arg
                405

<210> SEQ ID NO 5
<211> LENGTH: 8
<212> TYPE: PRT
<213> ORGANISM: Artificial Sequence
<220> FEATURE:
<223> OTHER INFORMATION: FLAG tag

<400> SEQUENCE: 5

Asp Tyr Lys Asp Asp Asp Lys
1               5

<210> SEQ ID NO 6
<211> LENGTH: 299
<212> TYPE: PRT
<213> ORGANISM: Homo sapiens

<400> SEQUENCE: 6

Met Ala Pro Trp Ser His Pro Ser Ala Gln Leu Gln Pro Val Gly Gly
1               5                   10                  15

Asp Ala Val Ser Pro Ala Leu Met Val Leu Leu Cys Leu Gly Leu Ser
                20                  25                  30

Leu Gly Pro Arg Thr His Val Gln Ala Gly Asn Leu Ser Lys Ala Thr
            35                  40                  45

Leu Trp Ala Glu Pro Gly Ser Val Ile Ser Arg Gly Asn Ser Val Thr
        50                  55                  60

Ile Arg Cys Gln Gly Thr Leu Glu Ala Gln Glu Tyr Arg Leu Val Lys
65                  70                  75                  80

Glu Gly Ser Pro Glu Pro Trp Asp Thr Gln Asn Pro Leu Glu Pro Lys
                85                  90                  95

Asn Lys Ala Arg Phe Ser Ile Pro Ser Met Thr Glu His His Ala Gly
            100                 105                 110

Arg Tyr Arg Cys Tyr Tyr Tyr Ser Pro Ala Gly Trp Ser Glu Pro Ser
        115                 120                 125

Asp Pro Leu Glu Leu Val Val Thr Gly Phe Tyr Asn Lys Pro Thr Leu
    130                 135                 140

Ser Ala Leu Pro Ser Pro Val Val Thr Ser Gly Glu Asn Val Thr Leu
145                 150                 155                 160

Gln Cys Gly Ser Arg Leu Arg Phe Asp Arg Phe Ile Leu Thr Glu Glu
                165                 170                 175

Gly Asp His Lys Leu Ser Trp Thr Leu Asp Ser Gln Leu Thr Pro Ser
            180                 185                 190

Gly Gln Phe Gln Ala Leu Phe Pro Val Gly Pro Val Thr Pro Ser His
        195                 200                 205

Arg Trp Met Leu Arg Cys Tyr Gly Ser Arg Arg His Ile Leu Gln Val
    210                 215                 220

Trp Ser Glu Pro Ser Asp Leu Leu Glu Ile Pro Val Ser Gly Ala Ala
225                 230                 235                 240

Asp Asn Leu Ser Pro Ser Gln Asn Lys Ser Asp Ser Gly Thr Ala Ser
                245                 250                 255

His Leu Gln Asp Tyr Ala Val Glu Asn Leu Ile Arg Met Gly Met Ala
            260                 265                 270

Gly Leu Ile Leu Val Val Leu Gly Ile Leu Ile Phe Gln Asp Trp His
        275                 280                 285

Ser Gln Arg Ser Pro Gln Ala Ala Ala Gly Arg
    290                 295

<210> SEQ ID NO 7
<211> LENGTH: 481
<212> TYPE: PRT
<213> ORGANISM: Homo sapiens

<400> SEQUENCE: 7

| | | | | | | | | | | | | | | |
|---|---|---|---|---|---|---|---|---|---|---|---|---|---|---|
|Met|Thr|Pro|Thr|Leu|Ala|Ala|Leu|Leu|Cys|Leu|Gly|Leu|Ser|Leu|Gly|
|1| | | |5| | | | |10| | | | |15| |

| | | | | | | | | | | | | | | |
|---|---|---|---|---|---|---|---|---|---|---|---|---|---|---|
|Pro|Arg|Thr|His|Val|Gln|Ala|Gly|Pro|Phe|Pro|Lys|Pro|Thr|Leu|Trp|
| | | |20| | | | |25| | | | |30| | |

|Ala|Glu|Pro|Gly|Ser|Val|Ile|Ser|Trp|Gly|Ser|Pro|Val|Thr|Ile|Trp|
|---|---|---|---|---|---|---|---|---|---|---|---|---|---|---|---|
| | | |35| | | | |40| | | | |45| | |

|Cys|Gln|Gly|Ser|Leu|Glu|Ala|Gln|Glu|Tyr|Arg|Leu|Asp|Lys|Glu|Gly|
|---|---|---|---|---|---|---|---|---|---|---|---|---|---|---|---|
| |50| | | | |55| | | | |60| | | | |

|Ser|Pro|Glu|Pro|Trp|Asp|Arg|Asn|Asn|Pro|Leu|Glu|Pro|Lys|Asn|Lys|
|---|---|---|---|---|---|---|---|---|---|---|---|---|---|---|---|
|65| | | | |70| | | | |75| | | | |80|

|Ala|Arg|Phe|Ser|Ile|Pro|Ser|Ile|Thr|Glu|His|His|Ala|Gly|Arg|Tyr|
|---|---|---|---|---|---|---|---|---|---|---|---|---|---|---|---|
| | | | |85| | | | |90| | | | |95| |

|Arg|Cys|His|Tyr|Tyr|Ser|Ser|Ala|Gly|Trp|Ser|Glu|Pro|Ser|Asp|Pro|
|---|---|---|---|---|---|---|---|---|---|---|---|---|---|---|---|
| | | |100| | | | |105| | | | |110| | |

|Leu|Glu|Leu|Val|Met|Thr|Gly|Ala|Tyr|Ser|Lys|Pro|Thr|Leu|Ser|Ala|
|---|---|---|---|---|---|---|---|---|---|---|---|---|---|---|---|
| | | |115| | | | |120| | | | |125| | |

|Leu|Pro|Ser|Pro|Val|Val|Ala|Ser|Gly|Gly|Asn|Met|Thr|Leu|Gln|Cys|
|---|---|---|---|---|---|---|---|---|---|---|---|---|---|---|---|
| |130| | | | |135| | | | |140| | | | |

|Gly|Ser|Gln|Lys|Gly|Tyr|His|His|Phe|Val|Leu|Met|Lys|Glu|Gly|Glu|
|---|---|---|---|---|---|---|---|---|---|---|---|---|---|---|---|
|145| | | | |150| | | | |155| | | | |160|

|His|Gln|Leu|Pro|Arg|Thr|Leu|Asp|Ser|Gln|Leu|His|Ser|Gly|Gly|
|---|---|---|---|---|---|---|---|---|---|---|---|---|---|---|
| | | |165| | | | |170| | | | |175| | |

|Phe|Gln|Ala|Leu|Phe|Pro|Val|Gly|Pro|Val|Asn|Pro|Ser|His|Arg|Trp|
|---|---|---|---|---|---|---|---|---|---|---|---|---|---|---|---|
| | | |180| | | | |185| | | | |190| | |

|Arg|Phe|Thr|Cys|Tyr|Tyr|Tyr|Met|Asn|Thr|Pro|Arg|Val|Trp|Ser|
|---|---|---|---|---|---|---|---|---|---|---|---|---|---|---|
| | | |195| | | | |200| | | | |205| | |

|His|Pro|Ser|Asp|Pro|Leu|Glu|Ile|Leu|Pro|Ser|Gly|Val|Ser|Arg|Lys|
|---|---|---|---|---|---|---|---|---|---|---|---|---|---|---|---|
| |210| | | | |215| | | | |220| | | | |

|Pro|Ser|Leu|Leu|Thr|Leu|Gln|Gly|Pro|Val|Leu|Ala|Pro|Gly|Gln|Ser|
|---|---|---|---|---|---|---|---|---|---|---|---|---|---|---|---|
|225| | | | |230| | | | |235| | | | |240|

|Leu|Thr|Leu|Gln|Cys|Gly|Ser|Asp|Val|Gly|Tyr|Asp|Arg|Phe|Val|Leu|
|---|---|---|---|---|---|---|---|---|---|---|---|---|---|---|---|
| | | | |245| | | | |250| | | | |255| |

|Tyr|Lys|Glu|Gly|Glu|Arg|Asp|Phe|Leu|Gln|Arg|Pro|Gly|Gln|Gln|Pro|
|---|---|---|---|---|---|---|---|---|---|---|---|---|---|---|---|
| | | |260| | | | |265| | | | |270| | |

|Gln|Ala|Gly|Leu|Ser|Gln|Ala|Asn|Phe|Thr|Leu|Gly|Pro|Val|Ser|Pro|
|---|---|---|---|---|---|---|---|---|---|---|---|---|---|---|---|
| | |275| | | | |280| | | | |285| | | |

|Ser|His|Gly|Gly|Gln|Tyr|Arg|Cys|Tyr|Gly|Ala|His|Asn|Leu|Ser|Ser|
|---|---|---|---|---|---|---|---|---|---|---|---|---|---|---|---|
| |290| | | | |295| | | | |300| | | | |

|Glu|Trp|Ser|Ala|Pro|Ser|Asp|Pro|Leu|Asn|Ile|Leu|Met|Ala|Gly|Gln|
|---|---|---|---|---|---|---|---|---|---|---|---|---|---|---|---|
|305| | | | |310| | | | |315| | | | |320|

|Ile|Tyr|Asp|Thr|Val|Ser|Leu|Ser|Ala|Gln|Pro|Gly|Pro|Thr|Val|Ala|
|---|---|---|---|---|---|---|---|---|---|---|---|---|---|---|---|
| | | |325| | | | |330| | | | |335| | |

|Ser|Gly|Glu|Asn|Val|Thr|Leu|Leu|Cys|Gln|Ser|Trp|Trp|Gln|Phe|Asp|
|---|---|---|---|---|---|---|---|---|---|---|---|---|---|---|---|
| | | |340| | | | |345| | | | |350| | |

|Thr|Phe|Leu|Leu|Thr|Lys|Glu|Gly|Ala|Ala|His|Pro|Pro|Leu|Arg|Leu|
|---|---|---|---|---|---|---|---|---|---|---|---|---|---|---|---|
| | | |355| | | | |360| | | | |365| | |

|Arg|Ser|Met|Tyr|Gly|Ala|His|Lys|Tyr|Gln|Ala|Glu|Phe|Pro|Met|Ser|
|---|---|---|---|---|---|---|---|---|---|---|---|---|---|---|---|
| |370| | | | |375| | | | |380| | | | |

|Pro|Val|Thr|Ser|Ala|His|Ala|Gly|Thr|Tyr|Arg|Cys|Tyr|Gly|Ser|Tyr|
|---|---|---|---|---|---|---|---|---|---|---|---|---|---|---|---|
|385| | | | |390| | | | |395| | | | |400|

```
Ser Ser Asn Pro His Leu Leu Ser Phe Pro Ser Glu Pro Leu Glu Leu
            405                 410                 415

Met Val Ser Gly His Ser Gly Gly Ser Ser Leu Pro Pro Thr Gly Pro
            420                 425                 430

Pro Ser Thr Pro Ala Ser His Ala Lys Asp Tyr Thr Val Glu Asn Leu
            435                 440                 445

Ile Arg Met Gly Met Ala Gly Leu Val Leu Val Phe Leu Gly Ile Leu
            450                 455                 460

Leu Phe Glu Ala Gln His Ser Gln Arg Asn Pro Gln Asp Ala Ala Gly
465                 470                 475                 480

Arg

<210> SEQ ID NO 8
<211> LENGTH: 119
<212> TYPE: PRT
<213> ORGANISM: Artificial Sequence
<220> FEATURE:
<223> OTHER INFORMATION: DX446 heavy chain

<400> SEQUENCE: 8

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Arg Met Thr Trp Val Lys Gln Ala Pro Gly Lys Gly Leu Lys Trp Met
        35                  40                  45

Gly Trp Ile Asn Thr Asn Thr Gly Asp Pro Thr Tyr Ala Glu Glu Leu
50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Thr Ala Thr Tyr Phe Cys
            85                  90                  95

Ala Arg Glu Gly Phe Phe Asn Tyr Ala Met Asp Tyr Trp Gly Gln Gly
            100                 105                 110

Thr Ser Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: DX446 light chain

<400> SEQUENCE: 9

Asp Ile Leu Leu Thr Gln Ser Pro Ala Ile Leu Ser Val Ser Pro Gly
1               5                   10                  15

Lys Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Pro
            85                  90                  95
```

Thr Phe Gly Ala Gly Thr Lys Leu Glu Leu Lys
            100                 105

<210> SEQ ID NO 10
<211> LENGTH: 5
<212> TYPE: PRT
<213> ORGANISM: Artificial Sequence
<220> FEATURE:
<223> OTHER INFORMATION: VH_DX446-CDR1

<400> SEQUENCE: 10

Asn Tyr Arg Met Thr
1               5

<210> SEQ ID NO 11
<211> LENGTH: 17
<212> TYPE: PRT
<213> ORGANISM: Artificial Sequence
<220> FEATURE:
<223> OTHER INFORMATION: VH_DX446-CDR2

<400> SEQUENCE: 11

Trp Ile Asn Thr Asn Thr Gly Asp Pro Thr Tyr Ala Glu Glu Leu Lys
1               5                   10                  15

Gly

<210> SEQ ID NO 12
<211> LENGTH: 10
<212> TYPE: PRT
<213> ORGANISM: Artificial Sequence
<220> FEATURE:
<223> OTHER INFORMATION: VH_DX446-CDR3

<400> SEQUENCE: 12

Glu Gly Phe Phe Asn Tyr Ala Met Asp Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: VL_DX446-CDR1

<400> SEQUENCE: 13

Arg Ala Ser Gln Ser Ile Gly Thr Ser Ile His
1               5                   10

<210> SEQ ID NO 14
<211> LENGTH: 7
<212> TYPE: PRT
<213> ORGANISM: Artificial Sequence
<220> FEATURE:
<223> OTHER INFORMATION: VL_DX446-CDR2

<400> SEQUENCE: 14

Tyr Ala Ser Glu Ser Ile Ser
1               5

<210> SEQ ID NO 15
<211> LENGTH: 9
<212> TYPE: PRT
<213> ORGANISM: Artificial Sequence
<220> FEATURE:
<223> OTHER INFORMATION: VL_DX446 -CDR3

```
<400> SEQUENCE: 15

Gln Gln Ser Asn Ser Trp Pro Pro Thr
1               5

<210> SEQ ID NO 16
<211> LENGTH: 116
<212> TYPE: PRT
<213> ORGANISM: Artificial Sequence
<220> FEATURE:
<223> OTHER INFORMATION: DX435 heavy chain

<400> SEQUENCE: 16

Glu Val Gln Leu Gln Gln Ser Gly Pro Glu Met Val Lys Pro Gly Ala
1               5                   10                  15

Ser Val Lys Ile Ser Cys Lys Ala Ser Gly Tyr Ala Phe Thr Asp Tyr
                20                  25                  30

Asn Ile His Trp Val Lys Lys Ser His Gly Lys Ser Pro Glu Trp Ile
            35                  40                  45

Gly His Ile Tyr Pro Tyr Asn Lys Asp Thr Val Phe Asn Gln Asn Lys
        50                  55                  60

Thr Lys Ala Thr Leu Thr Val Asp Lys Ser Thr Thr Thr Ala Tyr Met
65                  70                  75                  80

Asp Leu Arg Ser Leu Thr Ser Glu Asp Ser Ala Val Tyr Tyr Cys Ala
                85                  90                  95

Arg Gly Ala Val Gly Tyr Phe Asp Tyr Trp Gly Gln Gly Thr Thr Leu
            100                 105                 110

Thr Val Ser Ser
        115

<210> SEQ ID NO 17
<211> LENGTH: 107
<212> TYPE: PRT
<213> ORGANISM: Artificial Sequence
<220> FEATURE:
<223> OTHER INFORMATION: DX435 light chain

<400> SEQUENCE: 17

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Phe
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Tyr Pro Phe
                85                  90                  95

Thr Phe Gly Ala Gly Thr Lys Leu Glu Leu Lys
            100                 105

<210> SEQ ID NO 18
<211> LENGTH: 5
<212> TYPE: PRT
<213> ORGANISM: Artificial Sequence
<220> FEATURE:
<223> OTHER INFORMATION: VH_DX435-CDR1
```

```
<400> SEQUENCE: 18

Asp Tyr Asn Ile His
1               5

<210> SEQ ID NO 19
<211> LENGTH: 16
<212> TYPE: PRT
<213> ORGANISM: Artificial Sequence
<220> FEATURE:
<223> OTHER INFORMATION: VH_DX435-CDR2

<400> SEQUENCE: 19

His Ile Tyr Pro Tyr Asn Lys Asp Thr Val Phe Asn Gln Asn Lys Thr
1               5                   10                  15

<210> SEQ ID NO 20
<211> LENGTH: 8
<212> TYPE: PRT
<213> ORGANISM: Artificial Sequence
<220> FEATURE:
<223> OTHER INFORMATION: VH_DX435-CDR3

<400> SEQUENCE: 20

Gly Ala Val Gly Tyr Phe Asp Tyr
1               5

<210> SEQ ID NO 21
<211> LENGTH: 11
<212> TYPE: PRT
<213> ORGANISM: Artificial Sequence
<220> FEATURE:
<223> OTHER INFORMATION: VL_DX435-CDR1

<400> SEQUENCE: 21

Arg Ala Ser Gly Asn Ile His Asn Phe Leu Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: VL_DX435-CDR2

<400> SEQUENCE: 22

Asn Ala Lys Thr Leu Ala Asp
1               5

<210> SEQ ID NO 23
<211> LENGTH: 9
<212> TYPE: PRT
<213> ORGANISM: Artificial Sequence
<220> FEATURE:
<223> OTHER INFORMATION: VL_DX435-CDR3

<400> SEQUENCE: 23

Gln His Phe Trp Ser Tyr Pro Phe Thr
1               5

<210> SEQ ID NO 24
<211> LENGTH: 117
<212> TYPE: PRT
<213> ORGANISM: Artificial Sequence
<220> FEATURE:
<223> OTHER INFORMATION: DX439 heavy chain
```

<400> SEQUENCE: 24

Glu Val Gln Leu Gln Gln Pro Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Arg Gln Arg His Gly Lys Ser Leu Glu Trp Ile
        35                  40                  45

Gly His Ile Tyr Pro Tyr Asn Gly Asn Thr Val Tyr Asn Gln Arg Phe
    50                  55                  60

Lys Asn Lys Ala Thr Leu Asn Val Asp Asn Phe Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Ala Val Gly Tyr Phe Asp His Trp Gly Gln Gly Thr Thr
            100                 105                 110

Leu Thr Val Ser Ser
        115

<210> SEQ ID NO 25
<211> LENGTH: 107
<212> TYPE: PRT
<213> ORGANISM: Artificial Sequence
<220> FEATURE:
<223> OTHER INFORMATION: DX439 heavy chain

<400> SEQUENCE: 25

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Phe
            20                  25                  30

Leu Ala Trp Tyr Gln Gln Lys Gln Gly Arg Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Asn Tyr Tyr Cys Gln His Phe Trp Ser Tyr Pro Phe
                85                  90                  95

Thr Phe Gly Ala Gly Thr Asn Leu Glu Leu Lys
            100                 105

<210> SEQ ID NO 26
<211> LENGTH: 5
<212> TYPE: PRT
<213> ORGANISM: Artificial Sequence
<220> FEATURE:
<223> OTHER INFORMATION: VH_DX439-CDR1

<400> SEQUENCE: 26

Asp Tyr Asn Met His
1               5

<210> SEQ ID NO 27
<211> LENGTH: 17
<212> TYPE: PRT
<213> ORGANISM: Artificial Sequence
<220> FEATURE:
<223> OTHER INFORMATION: VH_DX439-CDR2

-continued

<400> SEQUENCE: 27

His Ile Tyr Pro Tyr Asn Gly Asn Thr Val Tyr Asn Gln Arg Phe Lys
1               5                   10                  15

Asn

<210> SEQ ID NO 28
<211> LENGTH: 8
<212> TYPE: PRT
<213> ORGANISM: Artificial Sequence
<220> FEATURE:
<223> OTHER INFORMATION: VH_DX439-CDR3

<400> SEQUENCE: 28

Gly Ala Val Gly Tyr Phe Asp His
1               5

<210> SEQ ID NO 29
<211> LENGTH: 11
<212> TYPE: PRT
<213> ORGANISM: Artificial Sequence
<220> FEATURE:
<223> OTHER INFORMATION: VL_DX439-CDR1

<400> SEQUENCE: 29

Arg Ala Ser Gly Asn Ile His Asn Phe Leu Ala
1               5                   10

<210> SEQ ID NO 30
<211> LENGTH: 7
<212> TYPE: PRT
<213> ORGANISM: Artificial Sequence
<220> FEATURE:
<223> OTHER INFORMATION: VL_DX439-CDR2

<400> SEQUENCE: 30

Asn Ala Lys Thr Leu Ala Asp
1               5

<210> SEQ ID NO 31
<211> LENGTH: 9
<212> TYPE: PRT
<213> ORGANISM: Artificial Sequence
<220> FEATURE:
<223> OTHER INFORMATION: VL_DX439-CDR3

<400> SEQUENCE: 31

Gln His Phe Trp Ser Tyr Pro Phe Thr
1               5

<210> SEQ ID NO 32
<211> LENGTH: 117
<212> TYPE: PRT
<213> ORGANISM: Artificial Sequence
<220> FEATURE:
<223> OTHER INFORMATION: DX440 heavy chain

<400> SEQUENCE: 32

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Ser Asp Tyr
                20                  25                  30

Asn Met His Trp Val Lys Gln Ser His Gly Lys Ser Leu Lys Trp Ile
            35                  40                  45

Gly His Ile Phe Pro Tyr Ile Gly Asp Thr Val Tyr Asn Gln Lys Phe
            50                  55                  60

Thr Ser Lys Ala Thr Leu Thr Val Asp Asn Ser Ser Thr Gly Tyr
65                  70                  75                  80

Met Glu Ile Arg Ser Leu Thr Ser Glu Asp Ser Ala Val Tyr Tyr Cys
                85                  90                  95

Ala Arg Gly Ala Val Gly Tyr Phe Asp Tyr Trp Gly Gln Gly Thr Thr
                100                 105                 110

Leu Thr Val Ser Ser
        115

<210> SEQ ID NO 33
<211> LENGTH: 107
<212> TYPE: PRT
<213> ORGANISM: Artificial Sequence
<220> FEATURE:
<223> OTHER INFORMATION: DX440 light chain

<400> SEQUENCE: 33

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro Gln Phe Leu Val
            35                  40                  45

Tyr Asn Ala Lys Thr Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Ser Phe Pro Phe
                85                  90                  95

Thr Phe Gly Ala Gly Thr Lys Leu Glu Leu Lys
            100                 105

<210> SEQ ID NO 34
<211> LENGTH: 5
<212> TYPE: PRT
<213> ORGANISM: Artificial Sequence
<220> FEATURE:
<223> OTHER INFORMATION: VH_DX440-CDR1

<400> SEQUENCE: 34

Asp Tyr Asn Met His
1               5

<210> SEQ ID NO 35
<211> LENGTH: 17
<212> TYPE: PRT
<213> ORGANISM: Artificial Sequence
<220> FEATURE:
<223> OTHER INFORMATION: VH_DX440-CDR2

<400> SEQUENCE: 35

His Ile Phe Pro Tyr Ile Gly Asp Thr Val Tyr Asn Gln Lys Phe Thr
1               5                   10                  15

Ser

<210> SEQ ID NO 36
<211> LENGTH: 8
<212> TYPE: PRT
<213> ORGANISM: Artificial Sequence

```
<220> FEATURE:
<223> OTHER INFORMATION: VH_DX440-CDR3

<400> SEQUENCE: 36

Gly Ala Val Gly Tyr Phe Asp Tyr
1               5

<210> SEQ ID NO 37
<211> LENGTH: 11
<212> TYPE: PRT
<213> ORGANISM: Artificial Sequence
<220> FEATURE:
<223> OTHER INFORMATION: VL_DX440-CDR1

<400> SEQUENCE: 37

Arg Ala Ser Gly Asn Ile His Asn Tyr Leu Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: VL_DX440-CDR2

<400> SEQUENCE: 38

Asn Ala Lys Thr Leu Ala Asp
1               5

<210> SEQ ID NO 39
<211> LENGTH: 9
<212> TYPE: PRT
<213> ORGANISM: Artificial Sequence
<220> FEATURE:
<223> OTHER INFORMATION: VL_DX440-CDR3

<400> SEQUENCE: 39

Gln His Phe Trp Ser Phe Pro Phe Thr
1               5

<210> SEQ ID NO 40
<211> LENGTH: 427
<212> TYPE: PRT
<213> ORGANISM: Homo sapiens

<400> SEQUENCE: 40

Gln Ala Gly Pro Leu Pro Lys Pro Thr Leu Trp Ala Glu Pro Gly Ser
1               5                   10                  15

Val Ile Ser Trp Gly Asn Ser Val Thr Ile Trp Cys Gln Gly Thr Leu
                20                  25                  30

Glu Ala Arg Glu Tyr Arg Leu Asp Lys Glu Glu Ser Pro Ala Pro Trp
            35                  40                  45

Asp Arg Gln Asn Pro Leu Glu Pro Lys Asn Lys Ala Arg Phe Ser Ile
        50                  55                  60

Pro Ser Met Thr Glu Asp Tyr Ala Gly Arg Tyr Arg Cys Tyr Tyr Arg
65                  70                  75                  80

Ser Pro Val Gly Trp Ser Gln Pro Ser Asp Pro Leu Glu Leu Val Met
                85                  90                  95

Thr Gly Ala Tyr Ser Lys Pro Thr Leu Ser Ala Leu Pro Ser Pro Leu
                100                 105                 110

Val Thr Ser Gly Lys Ser Val Thr Leu Leu Cys Gln Ser Arg Ser Pro
            115                 120                 125
```

Met Asp Thr Phe Leu Leu Ile Lys Glu Arg Ala Ala His Pro Leu Leu
130                 135                 140

His Leu Arg Ser Glu His Gly Ala Gln Gln His Gln Ala Glu Phe Pro
145                 150                 155                 160

Met Ser Pro Val Thr Ser Val His Gly Thr Tyr Arg Cys Phe Ser
                165                 170                 175

Ser His Gly Phe Ser His Tyr Leu Leu Ser His Pro Ser Asp Pro Leu
                180                 185                 190

Glu Leu Ile Val Ser Gly Ser Leu Glu Asp Pro Arg Pro Ser Pro Thr
                195                 200                 205

Arg Ser Val Ser Thr Ala Ala Gly Pro Glu Asp Gln Pro Leu Met Pro
210                 215                 220

Thr Gly Ser Val Pro His Ser Gly Leu Arg Arg His Trp Glu Val Leu
225                 230                 235                 240

Ile Gly Val Leu Val Val Ser Ile Leu Leu Leu Ser Leu Leu Leu Phe
                245                 250                 255

Leu Leu Leu Gln His Trp Arg Gln Gly Lys His Arg Thr Leu Ala Gln
                260                 265                 270

Arg Gln Ala Asp Phe Gln Arg Pro Gly Ala Ala Glu Pro Glu Pro
275                 280                 285

Lys Asp Gly Gly Leu Gln Arg Arg Ser Ser Pro Ala Ala Asp Val Gln
290                 295                 300

Gly Glu Asn Phe Cys Ala Ala Val Lys Asn Thr Gln Pro Glu Asp Gly
305                 310                 315                 320

Val Glu Met Asp Thr Arg Gln Ser Pro His Asp Glu Asp Pro Gln Ala
                325                 330                 335

Val Thr Tyr Ala Lys Val Lys His Ser Arg Pro Arg Arg Glu Met Ala
                340                 345                 350

Ser Pro Pro Ser Pro Leu Ser Gly Glu Phe Leu Asp Thr Lys Asp Arg
            355                 360                 365

Gln Ala Glu Glu Asp Arg Gln Met Asp Thr Glu Ala Ala Ala Ser Glu
370                 375                 380

Ala Pro Gln Asp Val Thr Tyr Ala Gln Leu His Ser Phe Thr Leu Arg
385                 390                 395                 400

Gln Lys Ala Thr Glu Pro Pro Ser Gln Glu Gly Ala Ser Pro Ala
                405                 410                 415

Glu Pro Ser Val Tyr Ala Thr Leu Ala Ile His
                420                 425

<210> SEQ ID NO 41
<211> LENGTH: 427
<212> TYPE: PRT
<213> ORGANISM: Homo sapiens

<400> SEQUENCE: 41

Gln Ala Gly Pro Leu Pro Lys Pro Thr Leu Trp Ala Glu Pro Gly Ser
1               5                   10                  15

Val Ile Ser Trp Gly Asn Ser Val Thr Ile Trp Cys Gln Gly Thr Leu
                20                  25                  30

Glu Ala Arg Glu Tyr Arg Leu Asp Lys Glu Glu Ser Pro Ala Pro Trp
            35                  40                  45

Asp Arg Gln Asn Pro Leu Glu Pro Lys Asn Lys Ala Arg Phe Ser Ile
        50                  55                  60

Pro Ser Met Thr Glu Asp Tyr Ala Gly Arg Tyr Arg Cys Tyr Tyr Arg
65                  70                  75                  80

Ser Pro Val Gly Trp Ser Gln Pro Ser Asp Pro Leu Glu Leu Val Met
            85                  90                  95

Thr Gly Ala Tyr Ser Lys Pro Thr Leu Ser Ala Leu Pro Ser Pro Leu
        100                 105                 110

Val Thr Ser Gly Lys Ser Val Thr Leu Leu Cys Gln Ser Arg Ser Pro
    115                 120                 125

Met Asp Thr Phe Leu Leu Ile Lys Glu Arg Ala Ala His Pro Leu Leu
130                 135                 140

His Leu Arg Ser Glu His Gly Ala Gln Gln His Gln Ala Glu Phe Pro
145                 150                 155                 160

Met Ser Pro Val Thr Ser Val His Gly Gly Thr Tyr Arg Cys Phe Ser
                165                 170                 175

Ser His Gly Phe Ser His Tyr Leu Leu Ser His Pro Ser Asp Pro Leu
            180                 185                 190

Glu Leu Ile Val Ser Gly Ser Leu Glu Asp Pro Arg Pro Ser Pro Thr
        195                 200                 205

Arg Ser Val Ser Thr Ala Ala Gly Pro Glu Asp Gln Pro Leu Met Pro
    210                 215                 220

Thr Gly Ser Val Pro His Ser Gly Leu Arg Arg His Trp Glu Val Leu
225                 230                 235                 240

Ile Gly Val Leu Val Val Ser Ile Leu Leu Leu Ser Leu Leu Leu Phe
                245                 250                 255

Leu Leu Leu Gln His Trp Arg Gln Gly Lys His Arg Thr Leu Ala Gln
            260                 265                 270

Arg Gln Ala Asp Phe Gln Arg Pro Pro Gly Ala Ala Glu Pro Glu Pro
        275                 280                 285

Lys Asp Gly Gly Leu Gln Arg Arg Ser Ser Pro Ala Ala Asp Val Gln
    290                 295                 300

Gly Glu Asn Phe Cys Ala Ala Val Lys Asn Thr Gln Pro Glu Asp Gly
305                 310                 315                 320

Val Glu Met Asp Thr Arg Gln Ser Pro His Asp Glu Asp Pro Gln Ala
                325                 330                 335

Val Thr Tyr Ala Lys Val Lys His Ser Arg Pro Arg Arg Glu Met Ala
            340                 345                 350

Ser Pro Pro Ser Pro Leu Ser Gly Glu Phe Leu Asp Thr Lys Asp Arg
        355                 360                 365

Gln Ala Glu Glu Asp Arg Gln Met Asp Thr Glu Ala Ala Ala Ser Glu
    370                 375                 380

Ala Pro Gln Asp Val Thr Tyr Ala Gln Leu His Ser Phe Thr Leu Arg
385                 390                 395                 400

Gln Lys Ala Thr Glu Pro Pro Ser Gln Glu Gly Ala Ser Pro Ala
                405                 410                 415

Glu Pro Ser Val Tyr Ala Thr Leu Ala Ile His
            420                 425

<210> SEQ ID NO 42
<211> LENGTH: 436
<212> TYPE: PRT
<213> ORGANISM: Homo sapiens

<400> SEQUENCE: 42

Leu Thr Asp Glu Glu Lys Arg Leu Met Val Glu Leu His Asn Leu Tyr
1               5                   10                  15

Arg Ala Gln Val Ser Pro Thr Ala Ser Asp Met Leu His Met Arg Trp
                20                  25                  30

Asp Glu Glu Leu Ala Ala Phe Ala Lys Ala Tyr Ala Arg Gln Cys Val
                35                  40                  45

Trp Gly His Asn Lys Glu Arg Gly Arg Gly Glu Asn Leu Phe Ala
    50                  55                  60

Ile Thr Asp Glu Gly Met Asp Val Pro Leu Ala Met Glu Glu Trp His
65                  70                  75                  80

His Glu Arg Glu His Tyr Asn Leu Ser Ala Ala Thr Cys Ser Pro Gly
                85                  90                  95

Gln Met Cys Gly His Tyr Thr Gln Val Val Trp Ala Lys Thr Glu Arg
                100                 105                 110

Ile Gly Cys Gly Ser His Phe Cys Glu Lys Leu Gln Gly Val Glu Glu
                115                 120                 125

Thr Asn Ile Glu Leu Leu Val Cys Asn Tyr Glu Pro Pro Gly Asn Val
                130                 135                 140

Lys Gly Lys Arg Pro Tyr Gln Glu Gly Thr Pro Cys Ser Gln Cys Pro
145                 150                 155                 160

Ser Gly Tyr His Cys Lys Asn Ser Leu Cys Glu Pro Ile Gly Ser Pro
                165                 170                 175

Glu Asp Ala Gln Asp Leu Pro Tyr Leu Val Thr Glu Ala Pro Ser Phe
                180                 185                 190

Arg Ala Thr Glu Ala Ser Asp Ser Arg Lys Met Gly Thr Pro Ser Ser
                195                 200                 205

Leu Ala Thr Gly Ile Pro Ala Phe Leu Val Thr Glu Val Ser Gly Ser
                210                 215                 220

Leu Ala Thr Lys Ala Leu Pro Ala Val Glu Thr Gln Ala Pro Thr Ser
225                 230                 235                 240

Leu Ala Thr Lys Asp Pro Pro Ser Met Ala Thr Glu Ala Pro Pro Cys
                245                 250                 255

Val Thr Thr Glu Val Pro Ser Ile Leu Ala Ala His Ser Leu Pro Ser
                260                 265                 270

Leu Asp Glu Glu Pro Val Thr Phe Pro Lys Ser Thr His Val Pro Ile
                275                 280                 285

Pro Lys Ser Ala Asp Lys Val Thr Asp Lys Thr Lys Val Pro Ser Arg
                290                 295                 300

Ser Pro Glu Asn Ser Leu Asp Pro Lys Met Ser Leu Thr Gly Ala Arg
305                 310                 315                 320

Glu Leu Leu Pro His Ala Gln Glu Ala Glu Ala Glu Ala Glu Leu
                325                 330                 335

Pro Pro Ser Ser Glu Val Leu Ala Ser Val Phe Pro Ala Gln Asp Lys
                340                 345                 350

Pro Gly Glu Leu Gln Ala Thr Leu Asp His Thr Gly His Thr Ser Ser
                355                 360                 365

Lys Ser Leu Pro Asn Phe Pro Asn Thr Ser Ala Thr Ala Asn Ala Thr
                370                 375                 380

Gly Gly Arg Ala Leu Ala Leu Gln Ser Ser Leu Pro Gly Ala Glu Gly
385                 390                 395                 400

Pro Asp Lys Pro Ser Val Val Ser Gly Leu Asn Ser Gly Pro Gly His
                405                 410                 415

Val Trp Gly Pro Leu Leu Gly Leu Leu Leu Pro Pro Leu Val Leu
                420                 425                 430

```
<210> SEQ ID NO 43
<211> LENGTH: 243
<212> TYPE: PRT
<213> ORGANISM: Homo sapiens

<400> SEQUENCE: 43
```

Ala Gly Ile Phe
            435

Leu Thr Asp Glu Glu Lys Arg Leu Met Val Glu Leu His Asn Leu Tyr
1               5                   10                  15

Arg Ala Gln Val Ser Pro Thr Ala Ser Asp Met Leu His Met Arg Trp
                20                  25                  30

Asp Glu Glu Leu Ala Ala Phe Ala Lys Ala Tyr Ala Arg Gln Cys Val
            35                  40                  45

Trp Gly His Asn Lys Glu Arg Gly Arg Arg Gly Glu Asn Leu Phe Ala
        50                  55                  60

Ile Thr Asp Glu Gly Met Asp Val Pro Leu Ala Met Glu Glu Trp His
65                  70                  75                  80

His Glu Arg Glu His Tyr Asn Leu Ser Ala Ala Thr Cys Ser Pro Gly
                85                  90                  95

Gln Met Cys Gly His Tyr Thr Gln Val Val Trp Ala Lys Thr Glu Arg
            100                 105                 110

Ile Gly Cys Gly Ser His Phe Cys Glu Lys Leu Gln Gly Val Glu Glu
        115                 120                 125

Thr Asn Ile Glu Leu Leu Val Cys Asn Tyr Glu Pro Pro Gly Asn Val
130                 135                 140

Lys Gly Lys Arg Pro Tyr Gln Glu Gly Thr Pro Cys Ser Gln Cys Pro
145                 150                 155                 160

Ser Gly Tyr His Cys Lys Asn Ser Leu Cys Glu Pro Ile Gly Ser Pro
                165                 170                 175

Glu Asp Ala Gln Asp Leu Pro Tyr Leu Val Thr Glu Ala Pro Ser Phe
            180                 185                 190

Arg Ala Thr Glu Ala Ser Asp Ser Arg Lys Met Gly Ala Glu Gly Pro
        195                 200                 205

Asp Lys Pro Ser Val Val Ser Gly Leu Asn Ser Gly Pro Gly His Val
    210                 215                 220

Trp Gly Pro Leu Leu Gly Leu Leu Leu Pro Pro Leu Val Leu Ala
225                 230                 235                 240

Gly Ile Phe

```
<210> SEQ ID NO 44
<211> LENGTH: 381
<212> TYPE: PRT
<213> ORGANISM: Homo sapiens

<400> SEQUENCE: 44
```

Leu Thr Asp Glu Glu Lys Arg Leu Met Val Glu Leu His Asn Leu Tyr
1               5                   10                  15

Arg Ala Gln Val Ser Pro Thr Ala Ser Asp Met Leu His Met Arg Trp
                20                  25                  30

Asp Glu Glu Leu Ala Ala Phe Ala Lys Ala Tyr Ala Arg Gln Cys Val
            35                  40                  45

Trp Gly His Asn Lys Glu Arg Gly Arg Arg Gly Glu Asn Leu Phe Ala
        50                  55                  60

```
Ile Thr Asp Glu Gly Met Asp Val Pro Leu Ala Met Glu Glu Trp His
 65                  70                  75                  80

His Glu Arg Glu His Tyr Asn Leu Ser Ala Thr Cys Ser Pro Gly
                 85                  90                  95

Gln Met Cys Gly His Tyr Thr Gln Val Val Trp Ala Lys Thr Glu Arg
            100                 105                 110

Ile Gly Cys Gly Ser His Phe Cys Glu Lys Leu Gln Gly Val Glu Glu
            115                 120                 125

Thr Asn Ile Glu Leu Leu Val Cys Asn Tyr Glu Pro Pro Gly Asn Val
130                 135                 140

Lys Gly Lys Arg Pro Tyr Gln Glu Gly Thr Pro Cys Ser Gln Cys Pro
145                 150                 155                 160

Ser Gly Tyr His Cys Lys Asn Ser Leu Cys Glu Pro Ile Gly Ser Pro
                165                 170                 175

Glu Asp Ala Gln Asp Leu Pro Tyr Leu Val Thr Glu Ala Pro Ser Phe
            180                 185                 190

Arg Ala Thr Glu Ala Ser Asp Ser Arg Lys Met Gly Thr Pro Ser Ser
            195                 200                 205

Leu Ala Thr Gly Ile Pro Ala Phe Leu Val Thr Glu Val Ser Gly Ser
210                 215                 220

Leu Ala Thr Lys Ala Leu Pro Ala Val Glu Thr Gln Ala Pro Thr Ser
225                 230                 235                 240

Leu Ala Thr Lys Asp Pro Pro Ser Met Ala Thr Glu Ala Pro Pro Cys
                245                 250                 255

Val Thr Thr Glu Val Pro Ser Ile Leu Ala Ala His Ser Leu Pro Ser
            260                 265                 270

Leu Asp Glu Glu Pro Val Thr Phe Pro Lys Ser Thr His Val Pro Ile
            275                 280                 285

Pro Lys Ser Ala Asp Lys Val Thr Asp Lys Thr Lys Val Pro Ser Arg
            290                 295                 300

Ser Pro Glu Asn Ser Leu Asp Pro Lys Met Ser Leu Thr Gly Ala Arg
305                 310                 315                 320

Glu Leu Leu Pro His Ala Gln Glu Ala Ala Glu Ala Glu Leu
                325                 330                 335

Pro Pro Ser Ser Glu Val Leu Ala Ser Val Phe Pro Ala Gln Asp Lys
                340                 345                 350

Pro Gly Glu Leu Gln Ala Thr Leu Asp His Thr Gly His Thr Ser Ser
            355                 360                 365

Lys Ser Leu Pro Lys Phe Pro Gln Tyr Leu Cys His Arg
370                 375                 380

<210> SEQ ID NO 45
<211> LENGTH: 258
<212> TYPE: PRT
<213> ORGANISM: Homo sapiens

<400> SEQUENCE: 45

Gly Asn Leu Ser Lys Ala Thr Leu Trp Ala Glu Pro Gly Ser Val Ile
 1               5                  10                  15

Ser Arg Gly Asn Ser Val Thr Ile Arg Cys Gln Gly Thr Leu Glu Ala
             20                  25                  30

Gln Glu Tyr Arg Leu Val Lys Glu Gly Ser Pro Glu Pro Trp Asp Thr
         35                  40                  45
```

```
Gln Asn Pro Leu Glu Pro Lys Asn Lys Ala Arg Phe Ser Ile Pro Ser
     50                  55                  60

Met Thr Glu His His Ala Gly Arg Tyr Arg Cys Tyr Tyr Tyr Ser Pro
 65                  70                  75                  80

Ala Gly Trp Ser Glu Pro Ser Asp Pro Leu Glu Leu Val Val Thr Gly
                 85                  90                  95

Phe Tyr Asn Lys Pro Thr Leu Ser Ala Leu Pro Ser Pro Val Val Thr
                100                 105                 110

Ser Gly Glu Asn Val Thr Leu Gln Cys Gly Ser Arg Leu Arg Phe Asp
            115                 120                 125

Arg Phe Ile Leu Thr Glu Glu Gly Asp His Lys Leu Ser Trp Thr Leu
130                 135                 140

Asp Ser Gln Leu Thr Pro Ser Gly Gln Phe Gln Ala Leu Phe Pro Val
145                 150                 155                 160

Gly Pro Val Thr Pro Ser His Arg Trp Met Leu Arg Cys Tyr Gly Ser
                165                 170                 175

Arg Arg His Ile Leu Gln Val Trp Ser Glu Pro Ser Asp Leu Leu Glu
            180                 185                 190

Ile Pro Val Ser Gly Ala Ala Asp Asn Leu Ser Pro Ser Gln Asn Lys
        195                 200                 205

Ser Asp Ser Gly Thr Ala Ser His Leu Gln Asp Tyr Ala Val Glu Asn
210                 215                 220

Leu Ile Arg Met Gly Met Ala Gly Leu Ile Leu Val Val Leu Gly Ile
225                 230                 235                 240

Leu Ile Phe Gln Asp Trp His Ser Gln Arg Ser Pro Gln Ala Ala Ala
                245                 250                 255

Gly Arg

<210> SEQ ID NO 46
<211> LENGTH: 460
<212> TYPE: PRT
<213> ORGANISM: Homo sapiens

<400> SEQUENCE: 46

Gln Ala Gly Pro Phe Pro Lys Pro Thr Leu Trp Ala Glu Pro Gly Ser
 1               5                  10                  15

Val Ile Ser Trp Gly Ser Pro Val Thr Ile Trp Cys Gln Gly Ser Leu
             20                  25                  30

Glu Ala Gln Glu Tyr Arg Leu Asp Lys Glu Gly Ser Pro Glu Pro Trp
         35                  40                  45

Asp Arg Asn Asn Pro Leu Glu Pro Lys Asn Lys Ala Arg Phe Ser Ile
     50                  55                  60

Pro Ser Ile Thr Glu His His Ala Gly Arg Tyr Arg Cys His Tyr Tyr
 65                  70                  75                  80

Ser Ser Ala Gly Trp Ser Glu Pro Ser Asp Pro Leu Glu Leu Val Met
                 85                  90                  95

Thr Gly Ala Tyr Ser Lys Pro Thr Leu Ser Ala Leu Pro Ser Pro Val
                100                 105                 110

Val Ala Ser Gly Gly Asn Met Thr Leu Gln Cys Gly Ser Gln Lys Gly
            115                 120                 125

Tyr His His Phe Val Leu Met Lys Glu Gly Glu His Gln Leu Pro Arg
130                 135                 140

Thr Leu Asp Ser Gln Gln Leu His Ser Gly Gly Phe Gln Ala Leu Phe
145                 150                 155                 160
```

```
Pro Val Gly Pro Val Asn Pro Ser His Arg Trp Arg Phe Thr Cys Tyr
            165                 170                 175

Tyr Tyr Tyr Met Asn Thr Pro Arg Val Trp Ser His Pro Ser Asp Pro
            180                 185                 190

Leu Glu Ile Leu Pro Ser Gly Val Ser Arg Lys Pro Ser Leu Leu Thr
            195                 200                 205

Leu Gln Gly Pro Val Leu Ala Pro Gly Gln Ser Leu Thr Leu Gln Cys
            210                 215                 220

Gly Ser Asp Val Gly Tyr Asp Arg Phe Val Leu Tyr Lys Glu Gly Glu
225                 230                 235                 240

Arg Asp Phe Leu Gln Arg Pro Gly Gln Gln Pro Gln Ala Gly Leu Ser
            245                 250                 255

Gln Ala Asn Phe Thr Leu Gly Pro Val Ser Pro Ser His Gly Gly Gln
            260                 265                 270

Tyr Arg Cys Tyr Gly Ala His Asn Leu Ser Ser Glu Trp Ser Ala Pro
            275                 280                 285

Ser Asp Pro Leu Asn Ile Leu Met Ala Gly Gln Ile Tyr Asp Thr Val
            290                 295                 300

Ser Leu Ser Ala Gln Pro Gly Pro Thr Val Ala Ser Gly Glu Asn Val
305                 310                 315                 320

Thr Leu Leu Cys Gln Ser Trp Trp Gln Phe Asp Thr Phe Leu Leu Thr
            325                 330                 335

Lys Glu Gly Ala Ala His Pro Pro Leu Arg Leu Arg Ser Met Tyr Gly
            340                 345                 350

Ala His Lys Tyr Gln Ala Glu Phe Pro Met Ser Pro Val Thr Ser Ala
            355                 360                 365

His Ala Gly Thr Tyr Arg Cys Tyr Gly Ser Tyr Ser Ser Asn Pro His
            370                 375                 380

Leu Leu Ser Phe Pro Ser Glu Pro Leu Glu Leu Met Val Ser Gly His
385                 390                 395                 400

Ser Gly Gly Ser Ser Leu Pro Pro Thr Gly Pro Ser Thr Pro Ala
            405                 410                 415

Ser His Ala Lys Asp Tyr Thr Val Glu Asn Leu Ile Arg Met Gly Met
            420                 425                 430

Ala Gly Leu Val Leu Val Phe Leu Gly Ile Leu Leu Phe Glu Ala Gln
            435                 440                 445

His Ser Gln Arg Asn Pro Gln Asp Ala Ala Gly Arg
            450                 455                 460

<210> SEQ ID NO 47
<211> LENGTH: 463
<212> TYPE: PRT
<213> ORGANISM: Artificial   Sequence
<220> FEATURE:
<223> OTHER INFORMATION: ILT3Fc

<400> SEQUENCE: 47

Gln Ala Gly Pro Leu Pro Lys Pro Thr Leu Trp Ala Glu Pro Gly Ser
1               5                   10                  15

Val Ile Ser Trp Gly Asn Ser Val Thr Ile Trp Cys Gln Gly Thr Leu
            20                  25                  30

Glu Ala Arg Glu Tyr Arg Leu Asp Lys Glu Glu Ser Pro Ala Pro Trp
            35                  40                  45

Asp Arg Gln Asn Pro Leu Glu Pro Lys Asn Lys Ala Arg Phe Ser Ile
            50                  55                  60
```

-continued

```
Pro Ser Met Thr Glu Asp Tyr Ala Gly Arg Tyr Arg Cys Tyr Tyr Arg
 65                  70                  75                  80

Ser Pro Val Gly Trp Ser Gln Pro Ser Asp Pro Leu Glu Leu Val Met
                 85                  90                  95

Thr Gly Ala Tyr Ser Lys Pro Thr Leu Ser Ala Leu Pro Ser Pro Leu
            100                 105                 110

Val Thr Ser Gly Lys Ser Val Thr Leu Leu Cys Gln Ser Arg Ser Pro
        115                 120                 125

Met Asp Thr Phe Leu Leu Ile Lys Glu Arg Ala Ala His Pro Leu Leu
    130                 135                 140

His Leu Arg Ser Glu His Gly Ala Gln Gln His Gln Ala Glu Phe Pro
145                 150                 155                 160

Met Ser Pro Val Thr Ser Val His Gly Gly Thr Tyr Arg Cys Phe Ser
                165                 170                 175

Ser His Gly Phe Ser His Tyr Leu Leu Ser His Pro Ser Asp Pro Leu
            180                 185                 190

Glu Leu Ile Val Ser Gly Ser Leu Glu Gly Pro Arg Pro Ser Pro Thr
        195                 200                 205

Arg Ser Val Ser Thr Ala Ala Gly Pro Glu Asp Gln Pro Leu Met Pro
210                 215                 220

Thr Gly Ser Val Pro His Ser Gly Leu Arg Arg His Trp Glu Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 48
<211> LENGTH: 121
```

```
<212> TYPE: PRT
<213> ORGANISM: Artificial Sequence
<220> FEATURE:
<223> OTHER INFORMATION: Anti-PI16 clone 20B5 heavy chain variable
      domain

<400> SEQUENCE: 48

Glu Val Gln Leu Leu Glu Ser Gly Gly Gly Leu Val Gln Pro Gly Gly
1               5                   10                  15

Ser Leu Arg Val Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Thr Thr His Tyr Ala Asp Ser Val
    50                  55                  60

Lys Gly Arg Phe Thr Ile Ser Arg Asp Asn Ser Lys Asn Thr Val Tyr
65                  70                  75                  80

Met Gln Met Ser Ser Leu Arg Ala Glu Asp Thr Ala Ala Tyr Tyr Cys
                85                  90                  95

Ala Lys Asp Leu Gly Leu Arg Ala Gln Gly Trp Phe Asp Pro Trp Gly
            100                 105                 110

Gln Gly Thr Leu Val Thr Val Ser Ser
            115                 120

<210> SEQ ID NO 49
<211> LENGTH: 111
<212> TYPE: PRT
<213> ORGANISM: Artificial Sequence
<220> FEATURE:
<223> OTHER INFORMATION: Anti-PI16 clone 20B5 light chain variable
      domain

<400> SEQUENCE: 49

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Ser Tyr Ala
            20                  25                  30

Ile Ala Trp His Gln Gln Pro Glu Lys Gly Pro Arg Tyr Leu Met
        35                  40                  45

Lys Leu Asn Ser Asp Gly Ser His Ser Lys Gly Asp Gly Ile Pro Asp
    50                  55                  60

Arg Phe Ser Gly Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95

Thr Gly Ile Ala Val Phe Gly Gly Thr Gln Leu Thr Pro Leu
            100                 105                 110

<210> SEQ ID NO 50
<211> LENGTH: 121
<212> TYPE: PRT
<213> ORGANISM: Artificial Sequence
<220> FEATURE:
<223> OTHER INFORMATION: Anti-PI16 clone 49A7 heavy chain variable
      domain

<400> SEQUENCE: 50

Glu Val Gln Leu Leu Glu Ser Gly Gly Gly Leu Val Gln Pro Gly Gly
1               5                   10                  15
```

```
Ser Leu Arg Leu Ser Cys Ile Ala Ser Gly Phe Thr Phe Ser Ser Tyr
            20                  25                  30

Ala Met Thr Trp Val Arg Gln Val Pro Gly Arg Gly Leu Glu Trp Val
            35                  40                  45

Ser Ala Ile Ser Gly Ser Gly Phe Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Glu Thr Ala Leu Tyr Phe Cys
                85                  90                  95

Ala Lys Asp Leu Gly Met Arg Ala Gln Gly Trp Phe Pro Trp Gly
                100                 105                 110

Gln Gly Thr Leu Val Thr Val Ser Ser
            115                 120
```

<210> SEQ ID NO 51
<211> LENGTH: 111
<212> TYPE: PRT
<213> ORGANISM: Artificial Sequence
<220> FEATURE:
<223> OTHER INFORMATION: Anti-PI16 clone 49A7 light chain variable
    domain

<400> SEQUENCE: 51

```
Gln Leu Val Leu Thr Gln Ser Pro Ser Ala Ser Leu Gly Ala
 1               5                  10                  15

Ser Val Lys Leu Thr Arg Thr Leu Ser Ser Gly Leu Ser Tyr Ala
            20                  25                  30

Ile Ala Arg Gln Gln Gln Gln Pro Glu Lys Gly Pro Arg Tyr Leu Met
            35                  40                  45

Lys Phe Asn Ser Asp Gly Ser His Ser Lys Gly Asp Gly Ile Pro Asp
 50                  55                  60

Arg Phe Ser Gly Ser Arg Ser Gly Thr Glu Arg Tyr Val Thr Ile Ser
 65                  70                  75                  80

Ser Leu Gln Ser Glu Asp Glu Ala Asp Tyr Tyr Cys Gln Thr Trp Gly
                85                  90                  95

Thr Gly Thr Ala Val Phe Gly Gly Gly Thr Gln Leu Thr Ala Leu
                100                 105                 110
```

<210> SEQ ID NO 52
<211> LENGTH: 121
<212> TYPE: PRT
<213> ORGANISM: Artificial Sequence
<220> FEATURE:
<223> OTHER INFORMATION: Anti-PI16 clone 10E3 heavy chain variable
    domain

<400> SEQUENCE: 52

```
Glu Val Leu Leu Leu Glu Ser Gly Gly Gly Leu Val His Pro Gly Gly
 1               5                  10                  15

Ser Leu Lys Leu Ser Cys Ala Ala Ser Gly Phe Thr Phe Ser Ser Tyr
            20                  25                  30

Ala Met Ser Trp Val Arg Gln Val Pro Gly Lys Gly Leu Glu Trp Val
            35                  40                  45

Ser Thr Ile Ser Gly Gly Gly Tyr Thr Tyr Phe Ala Asp Ser Val
 50                  55                  60

Lys Gly Arg Phe Thr Ile Ser Arg Asp Asn Ser Lys Asp Thr Leu Tyr
 65                  70                  75                  80
```

```
Leu Gln Met Asn Ser Leu Arg Ala Glu Asp Thr Ala Val Tyr Phe Cys
                85                  90                  95

Ala Lys Asp Leu Gly Ser Arg Ala Gln Gly Trp Phe Asp Pro Trp Gly
            100                 105                 110

Gln Gly Thr Leu Val Thr Val Ser Ser
        115                 120

<210> SEQ ID NO 53
<211> LENGTH: 117
<212> TYPE: PRT
<213> ORGANISM: Artificial Sequence
<220> FEATURE:
<223> OTHER INFORMATION: Anti-PI16 clone 10E3 light chain variable
      domain

<400> SEQUENCE: 53

Gln Pro Val Leu Thr Gln Pro Ser Ser His Ser Ala Ser Ser Gly Ala
1               5                   10                  15

Ser Val Arg Leu Thr Cys Met Leu Ser Ser Gly Phe Ser Val Gly Asp
            20                  25                  30

Phe Trp Ile Arg Trp Tyr Gln Gln Lys Pro Gly Asn Pro Pro Arg Tyr
        35                  40                  45

Leu Leu Tyr Tyr His Ser Asp Ser Asn Lys Gly Gln Gly Ser Gly Val
    50                  55                  60

Pro Ser Arg Phe Ser Gly Ser Asn Asp Ala Ser Ala Asn Ala Gly Ile
65                  70                  75                  80

Leu Arg Ile Ser Gly Leu Gln Pro Glu Asp Glu Ala Asp Tyr Tyr Cys
                85                  90                  95

Gly Thr Trp His Ser Asn Ser Lys Thr Phe Ile Phe Gly Ser Gly Thr
            100                 105                 110

Lys Val Thr Val Leu
        115

<210> SEQ ID NO 54
<211> LENGTH: 125
<212> TYPE: PRT
<213> ORGANISM: Artificial Sequence
<220> FEATURE:
<223> OTHER INFORMATION: Anti-PI16 clone 32A4 heavy chain variable
      domain

<400> SEQUENCE: 54

Gln Val Lys Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ile Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Asn Cys
                85                  90                  95

Ala Arg Asp Arg Arg Ile Thr Met Val Arg Gly Val Met Arg Gly Met
            100                 105                 110

Asp Val Trp Gly Gln Gly Thr Thr Val Thr Val Ser Ser
        115                 120                 125
```

<210> SEQ ID NO 55
<211> LENGTH: 108
<212> TYPE: PRT
<213> ORGANISM: Artificial Sequence
<220> FEATURE:
<223> OTHER INFORMATION: Anti-PI16 clone 32A4 light chain variable domain

<400> SEQUENCE: 55

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Trp Thr Phe Gly Gln Gly Thr Lys Val Glu Ile Lys
            100                 105

<210> SEQ ID NO 56
<211> LENGTH: 327
<212> TYPE: PRT
<213> ORGANISM: Artificial Sequence
<220> FEATURE:
<223> OTHER INFORMATION: Human IgG4 HC Constant domain (S228P)

<400> SEQUENCE: 56

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 57
<211> LENGTH: 330
<212> TYPE: PRT
<213> ORGANISM: Artificial Sequence
<220> FEATURE:
<223> OTHER INFORMATION: Human IgG1 HC Constant domain (L234A L235A
      D265S)

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

UNITED STATES PATENT AND TRADEMARK OFFICE
CERTIFICATE OF CORRECTION

| | | |
|---|---|---|
| PATENT NO. | : 12,037,393 B2 | Page 1 of 1 |
| APPLICATION NO. | : 17/663558 | |
| DATED | : July 16, 2024 | |
| INVENTOR(S) | : Daniel Cua et al. | |

It is certified that error appears in the above-identified patent and that said Letters Patent is hereby corrected as shown below:

On the Title Page

Item (54) and in the Specification, Column 1, Line 1:
Please delete "P116 ANTIBODIES"
And replace with "PI16 ANTIBODIES"

Signed and Sealed this
Nineteenth Day of November, 2024

Katherine Kelly Vidal
*Director of the United States Patent and Trademark Office*